United States Patent [19]

Fitzjohn et al.

[11] Patent Number: 5,451,594
[45] Date of Patent: Sep. 19, 1995

[54] HETEROCYCLIC COMPOUNDS

[75] Inventors: Steven Fitzjohn, Bracknell; Michael P. Robinson, Henley on Thames; Michael D. Turnbull, Reading; Alison M. Smith, Richmond; Roger Salmon, Bracknell; Robin Taylor, Wokingham, all of United Kingdom

[73] Assignee: Zeneca Limited, London, United Kingdom

[21] Appl. No.: 119,917

[22] Filed: Sep. 10, 1993

[30] Foreign Application Priority Data

Sep. 16, 1992 [GB] United Kingdom ............... 9219634

[51] Int. Cl.$^6$ ............... A61K 31/425; A61K 31/42; C07D 277/76; C07D 263/58; C07D 277/74
[52] U.S. Cl. ............... 514/367; 514/375; 548/151; 548/166; 548/170; 548/173; 548/221
[58] Field of Search ............... 548/173, 221, 151, 166, 548/170; 514/367, 375

[56] References Cited

U.S. PATENT DOCUMENTS

| | | | |
|---|---|---|---|
| 3,153,653 | 10/1964 | Raasch | 514/372 |
| 3,780,050 | 12/1973 | Brokke | 514/367 |
| 3,849,431 | 11/1974 | Gallay et al. | 514/367 |
| 3,933,819 | 1/1976 | Toukan et al. | 548/173 |
| 3,934,017 | 1/1976 | Gallay et al. | 514/367 |
| 4,059,635 | 11/1977 | Sugiyama et al. | 548/151 |
| 4,328,219 | 5/1982 | Mues et al. | 548/152 |
| 4,448,399 | 5/1984 | D'Amico | 548/173 |
| 5,162,351 | 11/1992 | Hubl et al. | 514/372 |

FOREIGN PATENT DOCUMENTS 507464 10/1992 European Pat. Off.
1413519 11/1975 United Kingdom.

*Primary Examiner*—Robert W. Ramsuer
*Assistant Examiner*—Michael G. Ambrose
*Attorney, Agent, or Firm*—Marian T. Thomson

[57] ABSTRACT

The invention provides compounds of formula (I) having nematicidal, insecticidal, acaricidal and fungicidal properties, compositions comprising them and processes and intermediates for their preparation:

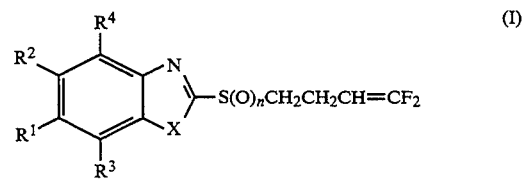

wherein:
X is oxygen or sulphur;
n is 0, 1 or 2;
$R^1$, $R^2$, $R^3$, and $R^4$ are as described in the specification.

13 Claims, No Drawings

HETEROCYCLIC COMPOUNDS

The present invention relates to novel benzoxazole and benzthiazole derivatives having nematicidal, insecticidal, acaricidal and fungicidal activity, to processes for their preparation, to compositions containing them, to methods for killing or controlling nematode, insect and acarid pests using them, and to methods of combating fungi using them.

UK Patent No 1413519 generically discloses 2-substituted benzoxazoles and benzthiazoles carrying the very specific isothiocyano substituent on the benzo-fused ring. No specific 2-haloalkenylthio examples are disclosed and the compounds are not mentioned in the context of agrochemical nematicidal activity. U.S. Pat. No. 4,328,219 discloses 2-substituted benzoxazoles and benzthiazoles as synergists for various conventional insecticides. Again, no specific 2-haloalkenylthio examples are disclosed and there is no disclosure of nematicidal activity. U.S. Pat. No 3,780,050 discloses activity against *Meloidogyne spp.* for the two specific compounds 2-(3,4,4-trifluorobut-3-enylthio)benzoxazole and 2-(3,4,4-trifluorobut3-enylthio)benzthiazole. The present invention relates to novel 2-(4,4-difluorobut-3-enylthio)-substituted benzoxazoles and benzthiazoles and oxidised derivatives thereof which exhibit significantly improved levels of nematicidal activity across a wide spectrum of nematode pests, as well as insecticidal activity (including systemic activity) and fungicidal activity.

According to the present invention there is provided a compound of formula (I) wherein X is oxygen or sulphur;

n is 0, 1 or 2;

$R^1$, $R^2$, $R^3$, and $R^4$ are independently selected from hydrogen alkyl alkenyl, alkynyl, cycloalkyl, alkylcycloalkyl, optionally substituted aryl, optionally substituted arylalkyl, optionally substituted aryloxy, optionally substituted arylalkoxy, alkoxy, alkenyloxy, alkynyloxy, hydroxyalkyl, alkoxyalkyl, alkylthio, alkenylthio, alkynylthio, haloalkyl, haloalkenyl, haloalkynyl, haloalkoxy, haloalkenyloxy, haloalkynyloxy, haloalkylthio, haloalkenylthio, haloalkynylthio, halogen, hydroxy, cyano, nitro —$NR^5R^6$, —$NR^7COR^8$, —$NR^9SO_2R^{10}$, —$N(SO_2$—$R^{11})(SO_2$—$R^{12})$, —$COR^{13}$, —$CONR^{14}R^{15}$, —$COOR^{16}$, —$OCOR^{17}$, —$OSO_2R^{18}$, —$SO_2NR^{19}R^{20}$, —$SO_2R^{21}$, —$SOR^{22}$, —$CSNR^{23}R^{24}$, —$SiR^{25}R^{26}R^{27}$, —$OCH_2CO_2R^{28}$, —$OCH_2CH_2CO_2R^{29}$, —$CONR^{30}SO_2R^{31}$ and —$SO_2Z$; or an adjacent of $R^1$, $R^2$, $R^3$ and $R^4$ when taken together form a fused 5- or 6-membered carbocyclic or heterocyclic ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently selected from hydrogen, alkyl, alkenyl, alkynyl, haloalkyl, haloalkenyl, haloalkynyl, optionally substituted aryl and optionally substituted arylalkyl; and Z is halogen.

When any one of $R^1$ to $R^{31}$ is an alkyl group it may be straight or branched chain and is preferably $C_{1-6}$ alkyl, and in particular $C_{1-4}$ alkyl, for example methyl, ethyl, propyl, iso-propyl, n-butyl, iso-butyl, sec-butyl or t-butyl.

When any one of $R^1$ to $R^{31}$ is an alkenyl or alkynyl group it may be straight or branched chain and is preferably $C_{2-6}$ alkenyl or $C_{2-6}$ alkynyl, for example vinyl, allyl, but-3-enyl, 3-methyl-but-3-enyl, ethynyl or propargyl.

When any one of $R^1$ to $R^4$ is a cycloalkyl or alkylcycloalkyl group, it is preferably C3-6 cycloalkyl or C4-7 alkylcycloalkyl, for example, cyclopropyl, cyclopentyl, cyclohexyl or methylcyclopropyl.

When any one of $R^1$ to $R^{31}$ is an optionally substituted aryl or an optionally substituted arylalkyl group, it is preferably an optionally substituted phenyl group or an optionally substituted phenyl-$C_{1-2}$-alkyl group, wherein the preferred optional substitution is one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example phenyl, benzyl, 4-methylphenyl, 4-chlorophenyl, 4-fluorophenyl, 4-nitrophenyl, 3-trifluoromethylphenyl, 4-trifluoromethylphenyl, 4-chlorobenzyl, 4-fluorobenzyl, 3-trifluoromethylbenzyl, 4-trifluoromethylbenzyl, 4-nitrobenzyl or 4-methylbenzyl.

When any one of $R^1$ to $R^4$ is an optionally substituted aryloxy or an optionally substituted arylalkoxy group, it is preferably optionally substituted phenoxy or optionally substituted phenyl-$C_{1-2}$-alkoxy, group, wherein the preferred optional substitution is one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example phenoxy, benzoxy, 4-methylphenoxy, 4-chlorophenoxy, 4-fluorophenoxy, 4-nitrophenoxy, 3-trifluoromethylphenoxy, 4-trifluoromethylphenoxy 4-chlorobenzoxy, 4-fluorobenzoxy, 3-trifluoromethylbenzoxy, 4-trifluoromethylbenzoxy, 4-nitrobenzoxy or 4-methylbenzoxy.

When any one of $R^1$ to $R^{31}$ is a haloalkyl, haloalkenyl or haloalkynyl group, it may contain one or more halogen atoms selected from chlorine, fluorine or bromine, and the alkyl, alkenyl or alkynyl moiety may be straight or branched chain and is preferably $C_{1-6}$ alkyl, especially $C_{1-4}$ alkyl, $C_{2-6}$ alkenyl or $C_{2-6}$ alkynyl, for example, fluoromethyl, difluoromethyl, trifluoromethyl, chloromethyl, dichloromethyl, trichloromethyl, 2-fluoroethyl, 2,2,2-trifluoroethyl, pentafluoroethyl, 2,2-difluoroethenyl, 3,3-dichloroprop-2-enyl, 2-chloroprop-2-enyl, 3,4,4-trifluorobut-3-enyl, 4-fluorobut-3-enyl, 4,4-difluorobut-3-enyl or 3-methyl-4,4-difluorobut-3-enyl.

When any one of $R^1$ to $R^4$ is an alkoxy, alkenyloxy, alkynyloxy, hydroxyalkyl or alkoxyalkyl group it may be straight or branched chain and is preferably $C_{1-6}$ alkoxy, for example methoxy, ethoxy, n-propoxy, iso-propoxy, n-butoxy, iso-butoxy, sec-butoxy or t-butoxy, $C_{2-6}$ alkenyloxy, for example vinyloxy, allyloxy, but-3-enyloxy or 3-methylbut-3-enyloxy, $C_{2-6}$ alkynyloxy, for example propargyloxy, hydroxy-$C_{1-6}$-alkyl, for example hydroxymethyl, 2-hydroxyethyl or 3-hydroxypropyl, $C_{2-6}$ alkoxyalkyl, for example methoxymethyl, methoxyethyl or ethoxymethyl, or $C_{3-6}$ dialkoxyalkyl, for example dimethoxymethyl or diethoxymethyl.

When any one of $R^1$ to $R^4$ is a haloalkoxy group, a haloalkenyloxy group or a haloalkynyloxy group, it may contain one or more halogen atoms selected from chlorine, fluorine or bromine, and the alkoxy, alkenyloxy or alkynyloxy moiety may be straight or branched chain and is preferably $C_{1-6}$ alkoxy, $C_{2-6}$ alkenyloxy or $C_{2-6}$ alkynyloxy, for example, trichloromethoxy, fluoromethoxy, difluoromethoxy, trifluoromethoxy, 2-fluoroethoxy, 2,2,2-trifluoroethoxy, pentafluoroethoxy, 1,1,2,2-tetrafluoroethoxy, 2,2-difluoroethenyloxy, 3,4,4-trifluorobut-3-enyloxy, 4-fluorobut-3-enyloxy, 4,4-difluorobut-3-enyloxy, 3-methyl-4,4-difluorobut-3-enyloxy, 2-chloroprop-2-enyloxy or 3,3-dichloroprop-2-enyloxy.

When any one of $R^1$ to $R^4$ is an alkylthio group, an alkenylthio group or an alkynylthio group, the alkyl, alkenyl or alkynyl moiety is preferably $C_{1-6}$ alkyl, especially $C_{1-4}$ alkyl, $C_{2-6}$ alkenyl or $C_{2-6}$ alkynyl, for example methylthio, ethylthio, n-propylthio, iso-propylthio, n-butylthio, iso-butylthio, sec-butylthio, t-butylthio, allylthio, but-3-enylthio, 3-methylbut-3-enylthio or propargylthio.

When any one of $R^1$ to $R^4$ is a haloalkylthio group, a haloalkenylthio group or a haloalkynylthio group, it may contain one or more halogen atoms selected from chlorine, fluorine or bromine, and the alkyl, alkenyl or alkynyl moiety is preferably $C_{1-6}$ alkyl, especially $C_{1-4}$ alkyl, $C_{2-6}$ alkenyl or $C_{2-6}$ alkynyl, for example fluoromethylthio, difluoromethylthio, trifluoromethylthio, trichloromethylthio, 2-fluoroethylthio, 2,2,2-trifluoroethylthio, 3-fluoro-n-propylthio, pentafluoroethylthio, 2-chloroprop-2-enylthio, 3,3-dichloroprop-2-enylthio, 3,4,4-trifluorobut-3-enylthio, 4-fluorobut-3-enylthio, 4,4-difluorobut-3-enylthio or 3-methyl-4,4-difluorobut-3-enylthio.

When any one of $R^1$ to $R^4$ is halogen, it is preferably fluorine, chlorine, bromine or iodine.

When any one of $R^1$ to $R^4$ is the group $-NR^5R^6$ it is preferably $-NH_2$, a $C_{1-6}$ alkylamino group, for example methylamino or ethylamino, or a di-($C_{1-6}$ alkyl)-amino group, for example dimethylamino or diethylamino.

When any one of $R^1$ to $R^4$ is the group $-NR^7COR^8$ it is preferably, $-NHCHO$, a $C_{2-6}$ acylamino group or an optionally substituted benzamido group, for example $-NHCOCH_3$, $-NHCOC_2H_5$, benzamido or benzamido optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro.

When any one of $R^1$ to $R^4$ is the group $-NR^9SO_2R^{10}$ it is preferably a $C_{1-6}$ alkanesulphonamido group, for example $-NHSO_2CH_3$ or $-NHSO_2C_2H_5$.

When any one of $R^1$ to $R^4$ is the group $-N(SO_2R^{11})(SO_2R^{12})$ it is preferably a di-($C_{1-6}$ alkanesulphonyl)amino group, for example $-N(SO_2CH_3)_2$ or $-N(SO_2C_2H_5)_2$.

When any one of $R^1$ to $R^4$ is the group $-COR^{13}$, it is preferably formyl, a $C_{2-6}$ acyl group or an optionally substituted benzoyl group, for example acetyl, propionyl, n-butanoyl, benzoyl or benzoyl optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-chlorobenzoyl, 4-fluorobenzoyl, 4-bromobenzoyl, 4-methylbenzoyl or 4-trifluoromethylbenzoyl.

When any one of $R^1$ to $R^4$ is the group $-CONR^{14}R^{15}$ it is preferably $-CONH_2$, an N-($C_{1-6}$ alkyl)-carboxamido group, for example $-CONHCH_3$, $-CONHC_2H_5$ or $-CONHCH_2CH_2CH_3$, or an N,N-di-($C_{1-6}$ alkyl)-carboxamido group, for example $-CON(CH_3)_2$, $-CON(CH_3)(C_2H_5)$ or $-CON(C_2H_5)_2$.

When any one of $R^1$ to $R^4$ is the group $-COOR^{16}$ it is preferably $-COOH$, a $C_{1-6}$ alkoxycarbonyl group, for example methoxycarbonyl or ethoxycarbonyl, a $C_{1-6}$ haloalkoxycarbonyl group, for example 2-fluoroethoxycarbonyl, or a $C_{2-6}$ haloalkenyloxycarbonyl group, for example 3,4,4-trifluorobut-3-enyloxycarbonyl, 4-fluorobut-3-enyloxycarbonyl, 4,4-difluorobut-3-enyloxycarbonyl or 3-methyl-4,4-difluorobut-3-enyloxycarbonyl, When any one of $R^1$ to $R^4$ is the group $-OCOR^{17}$, it is preferably a $C_{2-6}$ acyloxy group or an optionally substituted benzoyloxy, for example $-OCOCH_3$, $-OCOC_2H_5$, benzoyloxy or benzoyloxy optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro.

When any one of $R^1$ to $R^4$ is the group $-OSO_2R^{18}$, it is preferably a $C_{1-6}$ alkanesulphonyloxy group or an optionally substituted benzenesulphonyloxy group, for example methanesulphonyloxy, ethanesulphonyloxy, benzenesulphonyloxy or benzenesulphonyloxy optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-methylbenzenesulphonyloxy.

When any one of $R^1$ to $R^4$ is the group $-SO_2NR^{19}R^{20}$, it is preferably $-SO_2NH_2$, a $C_{1-6}$ alkylaminosulphonyl group, for example $-SO_2NHCH_3$ or $-SO_2NHC_2H_5$, or a di-($C_{1-6}$ alkyl)-aminosulphonyl group, for example $-SO_2N(CH_3)_2$ or $-SO_2N(C_2H_5)_2$.

When any one of $R^1$ to $R^4$ is the group $-SO_2R^{21}$, it is preferably a $C_{1-6}$ alkanesulphonyl group, a $C_{1-6}$ haloalkanesulphonyl group or an optionally substituted benzenesulphonyl group, for example methanesulphonyl, ethanesulphonyl, trifluoromethanesulphonyl, benzenesulphonyl or benzenesulphonyl optionally substituted with one or more substituents selected from halogen such as chlorine, fluorine or bromine, $C_{1-4}$ alkyl such as methyl or ethyl, $C_{1-4}$ alkoxy such as methoxy or ethoxy, $C_{1-4}$ haloalkyl such as chloromethyl, fluoromethyl, trifluoromethyl or 2,2,2-trifluoroethyl, $C_{1-4}$ haloalkoxy such as trifluoromethoxy or 2,2,2-trifluoroethoxy, hydroxy, cyano and nitro, for example 4-methylbenzenesulphonyl.

When any one of $R^1$ to $R^4$ is the group $-SOR^{22}$, it is preferably a $C_{1-6}$ alkanesulphinyl group, for example methanesulphinyl or ethanesulphinyl, or a $C_{1-6}$ haloalkanesulphinyl group, for example trifluoromethanesulphinyl.

When any one of $R^1$ to $R^4$ is the group —$CSNR^{23}R^{24}$ it is preferably —$CSNH_2$, —$CSNHCH_3$ or —$CSN(CH_3)_2$.

When any one of $R^1$ to $R^4$ is the group —$SiR^{25}R^{26}R^{27}$, it is preferably a tri-($C_{1-6}$ alkyl)silyl group, for example, trimethylsilyl or triethylsilyl.

When any one of $R^1$ to $R^4$ is the group —$OCH_2CO_2R^{28}$, it is preferably a $C_{1-6}$ alkoxycarbonylmethoxy group, for example methoxycarbonylmethoxy or ethoxycarbonylmethoxy.

When any one of $R^1$ to $R^4$ is the group —$OCH_2CH_2CO_2R^{29}$, it is preferably a $C_{1-6}$ alkoxycarbonylethoxy group, for example methoxycarbonylethoxy or ethoxycarbonylethoxy.

When any one of $R^1$ to $R^4$ is the group —$CONR^{30}SO_2R^{31}$, it is preferably an N-($C_{1-6}$ alkanesulphonyl)-carboxamido group or an N-($C_{1-6}$ alkyl)-N-($C_{1-6}$ alkanesulphonyl)carboxamido group, for example N-(methanesulphonyl)carboxamido or N-methyl-N-(methanesulphonyl)carboxamido.

When any one of $R^1$ to $R^4$ is the group —$SO_2Z$, it is preferably —$SO_2F$, —$SO_2Cl$ or —$SO_2Br$.

When an adjacent pair of $R^1$, $R^2$, $R^3$ and $R^4$ taken together form a fused 5- or 6-membered carbocyclic or heterocyclic ring, the pair of substituents taken together is preferably —$(CH_2)_3$—, —$(CH_2)_4$—, —CH=CH—CH=CH—, —O—$CH_2$—O— optionally substituted with one or two halogen atoms, for example —O—CHF—)— or —O—$CF_2$—O—, —O—CH($CH_3$)—O—, —O—C($CH_3$)$_2$—O— or —O—$(CH_2)_2$—O—, and the fused ring formed thereby is preferably a 5- or 6-membered heterocyclic ring containing two oxygen atoms and optionally substituted with one or more halogen or methyl groups, or a 5- or 6-membered carbocyclic ring.

Accordingly, the invention provides, in a further aspect, a compound of formula (I) wherein X is oxygen or sulphur;

n is 0, 1 or 2;

$R^1$, $R^2$, $R^3$, and $R^4$ are independently selected from hydrogen, $C_{1-6}$ alkyl $C_{2-6}$ alkenyl, $C_{2-6}$ alkynyl, $C_{3-6}$ cycloalkyl, $C_{4-7}$ alkylcycloalkyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenyl-$C_{1-2}$-alkyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenyl-$C_{1-2}$-alkoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, $C_{1-6}$ alkoxy, $C_{2-6}$ alkenyloxy, $C_{2-6}$ alkynyloxy, hydroxy-$C_{1-6}$-alkyl, $C_{2-6}$ alkoxyalkyl, $C_{3-6}$ dialkoxyalkyl, $C_{1-6}$ alkylthio, $C_{2-6}$ alkenylthio, $C_{2-6}$ alkynylthio, $C_{1-6}$ haloalkyl, $C_{2-6}$ haloalkenyl, $C_{2-6}$ haloalkynyl, $C_{1-6}$ haloalkoxy, $C_{2-6}$ haloalkenyloxy, $C_{2-6}$ haloalkynyloxy, $C_{1-6}$ haloalkylthio, $C_{2-6}$ haloalkenylthio, $C_{1-6}$ haloalkynylthio, halogen, hydroxy, cyano, nitro, —$NR^5R^6$, —$NR^7COR^8$, —$NR^9SO_2R^{10}$, —$N(SO_2—R^{11})(SO_2—R^{12})$, —$COR^{13}$, $CONR^{14}R^{15}$, —$COOR^{16}$, —O—$COR^{17}$, —$OSO_2R^{18}$, —$SO_2NR^{19}R^{20}$, —$SO_2R^{21}$, —$SOR^{22}$, —$CSNR^{23}R^{24}$, $SiR^{25}R^{26}R^{27}$, —$OCH_2CO_2R^{28}$, —$OCH_2CH_2CO_2R^{29}$, —$CONR^{30}SO_2R^{31}$ and —$SO_2Z$; or an adjacent pair of $R^1$, $R^2$, $R^3$ and $R^4$ when taken together form a fused 5- or 6-membered heterocyclic ring containing two oxygen atoms and optionally substituted with one or more halogen or methyl groups, or a 5- or 6-membered carbocyclic ring;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently selected from hydrogen, $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, and benzyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro; and Z is fluoro, chloro or bromo.

A further group of compounds according to the invention which are of particular interest are those of Formula (I) wherein:

X is oxygen or sulphur;

n is 0, 1 or 2;

$R^1$, $R^2$, $R^3$, and $R^4$ are independently selected from hydrogen $C_{1-4}$ alkyl such as methyl or ethyl, $C_{2-6}$ alkenyl such as allyl, but-3-enyl or 3-methylbut-3-enyl, $C_{2-6}$ alkynyl such as ethynyl or propargyl, $C_{3-6}$ cycloalkyl such as cyclopropyl, $C_{4-7}$ alkylcycloalkyl such as 1-methylcyclopropyl, phenyl optionally substituted by chloro, fluoro, methyl, ethyl, methoxy, trifluoromethoxy, trifluoromethyl or nitro, such as phenyl, 4-chlorophenyl, 4-fluorophenyl, 3-trifluoromethylphenyl, 4-trifluoromethylphenyl, 4-methylphenyl or 4-nitrophenyl, benzyl optionally substituted by chloro, fluoro, methyl, ethyl, methoxy, trifluoromethoxy, trifluoromethyl or nitro, such as benzyl, 4-chlorobenzyl, 4-fluorobenzyl, 3-trifluoromethylbenzyl, 4-trifluoromethylbenzyl, 4-methylbenzyl or 4-nitrobenzyl, phenoxy optionally substituted by chloro, fluoro, methyl, trifluoromethyl or nitro, such as phenoxy, 4-chlorophenoxy, 4-fluorophenoxy, 3-trifluoromethylphenoxy, 4-trifluoromethylphenoxy, 4-methylphenoxy or 4-nitrophenoxy, benzoxy optionally substituted by chloro, fluoro, methyl, trifluoromethyl or nitro, such as benzoxy, 4-chlorobenzoxy, 4-fluorobenzoxy, 3-trifluoromethylbenzoxy, 4-trifluoromethylbenzoxy, 4-methylbenzoxy or 4-nitrobenzoxy, $C_{1-4}$ alkoxy such as methoxy, ethoxy, iso-propoxy, n-propoxy or sec-butoxy, $C_{2-6}$ alkenyloxy such as allyloxy, but-3-enyloxy or 3-methylbut-3-enyloxy, $C_{2-4}$ alkynyloxy such as propargyloxy, hydroxy-$C_{1-4}$-alkyl such as hydroxymethyl, 2-hydroxyethyl or 3-hydroxypropyl, $C_{2-4}$ alkoxyalkyl such as methoxymethyl, ethoxymethyl, methoxyethyl, $C_{3-6}$ dialkoxyalkyl such as dimethoxymethyl, $C_{1-4}$ alkylthio such as methylthio or ethylthio, $C_{2-6}$ alkenylthio such as allylthio, but-3-enylthio or 3-methylbut-3-enylthio, $C_{2-4}$ alkynylthio such as propargylthio, $C_{1-4}$ fluoroalkyl such as fluoromethyl, difluoromethyl, trifluoromethyl or 2-fluoroethyl, $C_{1-4}$ chloroalkyl such as chloromethyl, dichloromethyl or trichloromethyl, $C_{2-6}$ fluoroalkenyl such as 2,2-difluoroethenyl, 3,4,4-trifluorobut-3-enyl, 4,4-difluorobut-3-enyl or 4,4-difluoro-3-methylbut-3-enyl, $C_{2-4}$ chloroalkenyl such as 3,3-dichloroprop-2-enyl or 2-chloroprop-2-enyl, $C_{1-4}$ fluoroalkoxy such as fluoromethoxy, difluoromethoxy, trifluoromethoxy, 2-fluoroethoxy or 1,1,2,2-tetrafluoroethoxy, $C_{1-4}$ chloroalkoxy such as trichloromethoxy, $C_{2-6}$ fluoroalkenyloxy such as 3,4,4-trifluorobut-3-enyloxy, 4,4-difluorobut-3-enyloxy or 4,4-difluoro-3-methylbut-3-enyloxy, $C_{2-4}$ chloroalkenyloxy such as 2-chloroprop-2-enyloxy or 3,3-dichloroprop-2-enyloxy, $C_{1-4}$ fluoroalkylthio such as fluoromethylthio, difluoromethylthio, trifluoromethylthio or 2-fluoroethylthio, $C_{1-4}$ chloroalkylthio such as trichloromethylthio, $C_{2-6}$ fluoroalkenylthio such as 3,4,4-trifluorobut-3-enylthio, 4,4- difluorobut-3-enylthio or 4,4-difluoro-3-methylbut-3-enylthio, $C_{2-4}$ chloroalkenylthio such as 2-chloroprop-2-enylthio or 3,3-dichloroprop-2-enylthio, chloro, fluoro, bromo, iodo, hydroxy, cyano, nitro, amino, —$NHR^5$ where $R^5$ where is $C_{1-4}$ alkyl, such as methylamino or ethylamino, —$NR^5R^6$ where $R^5$ and $R^6$ are $C_{1-4}$ alkyl such as dimethylamino or diethylamino, —$NR^7COR^8$ where $R^7$ is hydrogen and $R^8$ is hydrogen or $C_{1-4}$ alkyl, such as formamido, acetamido, propionamido or benzamide, —$NR^9SO_2R^{10}$ where $R^9$ is hydrogen and $R^{10}$ is $C_{1-4}$ alkyl, such as methanesulphonamido or ethanesulphonamido, —$N(SO_2—R^{11})(SO_2—R^{12})$ where $R^{11}$ and $R^{12}$ are $C_{1-4}$ alkyl such as N,N-di-(methanesulphonyl)amino or N,N-di-(ethanesulphonyl)amino, —$COR^{13}$ where $R^{13}$ is hydrogen or $C_{1-4}$ alkyl such as formyl, acetyl or propionyl, —$CONR_{14}R^{15}$ where $R^{14}$ and $R^{15}$ are hydrogen or $C_{1-4}$ alkyl, such as carboxamido, N-methylcarboxamido, N-ethylcarboxamido, N,N-dimethylcarboxamido, N-methyl-N-ethylcarboxamido, N,N-diethylcarboxamido or N-(n-propyl)carboxamido, —$COOR^{16}$ where $R^{16}$ is hydrogen, $C_{1-4}$ alkyl, $C_{1-4}$ haloalkyl or $C_{2-6}$ fluoroalkenyl, such as —COOH, methoxycarbonyl, ethoxycarbonyl, 2-fluoroethoxycarbonyl, 3,4,4-trifluorobut-3-enyloxycarbonyl, 3-methyl-4,4-difluorobut-3-enyloxycarbonyl or 4,4-difluorobut-3-enyloxycarbonyl, —$OCOR^{17}$ where $R^{17}$ is $C_{1-4}$ alkyl such as methoxycarbonyloxy or ethoxycarbonyloxy, —$OSO_2R^{18}$ where $R^{18}$ is $C_{1-4}$ alkyl such as methanesulphonyloxy or ethanesulphonyloxy, —$SO_2NR^{19}R^{20}$ where $R^{19}$ and $R^{20}$ are hydrogen or $C_{1-4}$ alkyl such as —$SO_2NH_2$, N,N-dimethylaminosulphonyl or N,N-diethylaminosulphonyl, —$SO_2R^{21}$ where $R^{21}$ is $C_{1-4}$ alkyl or $C_{1-4}$ haloalkyl such as methanesulphonyl, ethanesulphonyl or trifluoromethanesulphonyl, —$SOR^{22}$ where $R^{22}$ is $C_{1-4}$ alkyl or $C_{1-4}$ haloalkyl such as methanesulphinyl, ethanesulphinyl or trifluoromethanesulphinyl, —$CSNR^{23}R^{24}$ where $R^{23}$ and $R^{24}$ are hydrogen or $C_{1-4}$ alkyl such as —$CSNH_2$, —$CSNH(CH_3)$ or —$CSN(CH_3)_2$, —$SiR^{25}R^{26}R^{27}$ where $R^{25}$, $R^{26}$ and $R^{27}$ are $C_{1-4}$ alkyl such as trimethylsilyl, —$OCH_2CO_2R^{28}$ where $R^{28}$ is $C_{1-4}$ alkyl such as —$OCH_2CO_2CH_3$ or —$OCH$—$CO_2CH_2CH_3$, —$CONR^{30}SO_2R^{31}$ where $R^{30}$ is hydrogen and $R^{31}$ is $C_{1-4}$ alkyl such as N-(methanesulphonyl)carboxamido and —$SO_2F$; or where $R^1$ and $R^2$ taken together, $R^1$ and $R^3$ taken together or $R^2$ and $R^4$ taken together are —$(CH_2)_3$—, —$(CH_2)_4$—, —CH=CH—CH=CH—, —O—$CH_2$—O— optionally substituted with one or two halogen atoms, for example —O—CHF—O— or —O—$CF_2$—O—, —O—$CH(CH_3)$—O—, —O—$C(CH_3)_2$—O— or —O—$(CH_2)_2$—O—.

A further group of compounds according to the invention which are of particular interest are those of Formula (I) wherein:

X is oxygen or sulphur;

n is 0, 1 or 2;

$R^1$, $R^2$, $R^3$, and $R^4$ are independently selected from hydrogen, $C_{1-4}$ alkyl such as methyl or ethyl, $C_{1-4}$ alkoxy such as methoxy, ethoxy, iso-propoxy or sec-butoxy, $C_{1-4}$ alkylthio such as methylthio or ethylthio, $C_{1-4}$ fluoroalkyl such as fluoromethyl, difluoromethyl or trifluoromethyl, $C_{1-4}$ fluoroalkoxy such as fluoromethoxy, difluoromethoxy, trifluoromethoxy, 2-fluoroethoxy or 1,1,2,2-tetrafluoroethoxy, $C_{2-6}$ fluoroalkenyloxy such as 3,4,4-trifluorobut-3-enyloxy, 4,4-difluorobut-3-enyloxy or 4,4-difluoro-3-methylbut-3-enyloxy, $C_{1-4}$ fluoroalkylthio such as trifluoromethylthio, $C_{2-6}$ fluoroalkenylthio such as 3,4,4-trifluorobut-3-enylthio, 4,4-difluorobut-3-enylthio or 4,4-difluoro-3-methylbut-3-enylthio, chloro, fluoro, bromo, iodo, hydroxy, cyano, nitro, —$COOR^{16}$ where $R^{16}$ is hydrogen, $C_{1-4}$ alkyl, $C_{1-4}$ haloalkyl or $C_{2-6}$ fluoroalkenyl such as —COOH, methoxycarbonyl, ethoxycarbonyl, 2-fluoroethoxycarbonyl, 3,4,4-trifluorobut-3-enyloxycarbonyl, 3-methyl-4,4-difluorobut-3-enyloxycarbonyl or 4,4-difluorobut-3-enyloxycarbonyl, —$SO_2R^{21}$ where $R^{21}$ is $C_{1-4}$ alkyl or $C_{1-4}$ haloalkyl such as methanesulphonyl or trifluoromethanesulphonyl, —$SOR^{22}$ where $R^{22}$ is $C_{1-4}$ alkyl or $C_{1-4}$ haloalkyl such as methanesulphinyl trifluoromethanesulphinyl and —$CSNH_2$; or where $R^1$ and $R^2$ taken together are —O—$(CH_2)_2$—O—.

A further group of compounds according to the invention which are of particular interest are those of Formula (I) wherein $R^1$, $R^2$, $R^3$, $R^4$, Z, X and n have any of the meanings given in claim 1, with the proviso that at least two of the groups $R^1$, $R^2$, $R^3$, and $R^4$ are hydrogen.

A further group of compounds according to the invention which are of particular interest are those of Formula (I) wherein X and n have any of the meanings given in claim 1 and each of the groups $R^1$, $R^2$, $R^3$ and $R^4$ is hydrogen.

Compounds according to the invention which are of particular interest are those of Formula (I) wherein X, $R^1$—$R^4$ and Z have any of the meanings given above and n is 0.

Those compounds of Formula (I) in which n is 1 exhibit stereoisomerism at the oxidised sulphur atom. The scope of the invention is to be understood to include all individual isomers of any compound according to the invention, and all isomer mixtures, including racemic mixtures.

Examples of compounds of formula (I) according to the invention are set out in Table I.

TABLE I

| NO. | $R^1$ | $R^2$ | $R^3$ | $R^4$ | X | n |
|---|---|---|---|---|---|---|
| 1 | H | H | H | H | S | 0 |
| 2 | H | H | H | H | O | 0 |
| 3 | H | F | H | H | O | 0 |
| 4 | H | H | F | H | S | 2 |
| 5 | $NO_2$ | H | H | H | O | 0 |
| 6 | $NH_2$ | H | H | H | O | 0 |
| 7 | $CH_3$ | H | H | H | S | 0 |
| 8 | H | F | F | H | O | 0 |
| 9 | H | H | H | H | O | 1 |
| 10 | $CO_2CH_3$ | H | H | H | O | 0 |
| 11 | $NHCOCH_3$ | H | H | H | S | 0 |
| 12 | H | H | H | H | S | 1 |
| 13 | COOH | H | H | H | S | 0 |
| 14 | H | H | H | H | O | 2 |
| 15 | F | H | H | H | S | 0 |

TABLE I-continued

| NO. | R¹ | R² | R³ | R⁴ | X | n |
|---|---|---|---|---|---|---|
| 16 | H | H | H | CH₃ | S | 0 |
| 17 | H | H | CH₃ | H | O | 0 |
| 18 | H | H | CH₂CH=CH₂ | H | O | 0 |
| 19 | H | H | cC₃H₅ | H | O | 0 |
| 20 | H | H | Cl | H | O | 0 |
| 21 | H | H | CN | H | S | 0 |
| 22 | H | CH₃ | H | H | S | 0 |
| 23 | H | CH₂CH=CH₂ | H | H | O | 0 |
| 24 | H | cC₃H₅ | H | H | O | 0 |
| 25 | H | Cl | H | H | S | 1 |
| 26 | H | C₆H₅ | H | H | O | 0 |
| 27 | CH₃ | CH₃ | H | H | O | 0 |
| 28 | Cl | Cl | H | H | S | 0 |
| 29 | F | Cl | H | H | O | 0 |
| 30 | OCH₃ | H | NHCOCH₃ | H | O | 0 |
| 31 | OCH₃ | H | OCH₃ | H | O | 0 |
| 32 | OCH₃ | OCH₃ | H | H | O | 0 |
| 33 | 1-CH₃-cC₃H₅ | H | H | H | S | 0 |
| 34 | OH | F | H | H | O | 0 |
| 35 | OH | H | Cl | H | S | 0 |
| 36 | H | H | CO₂CH₃ | H | O | 0 |
| 37 | OCH₂CF₃ | H | H | H | S | 0 |
| 38 | OCH₂CF₃ | H | H | H | O | 2 |
| 39 | OCH₂CH₃ | H | H | H | S | 1 |
| 40 | H | H | CH₂OCH₃ | H | S | 0 |
| 41 | H | CH₃ | H | H | O | 0 |
| 42 | H | H | CN | H | O | 0 |
| 43 | —CG=CH—CH=CH— | | H | H | S | 0 |
| 44 | —CH=CH—CH=CH— | | H | H | O | 0 |
| 45 | Cl | H | H | H | O | 0 |
| 46 | Cl | H | H | H | S | 0 |
| 47 | F | H | H | H | O | 0 |
| 48 | CH₃ | H | H | H | O | 0 |
| 49 | NHCOCH₃ | H | H | H | O | 0 |
| 50 | NHCOC₂H₅ | H | H | H | S | 0 |
| 51 | NHSO₂CH₃ | H | H | H | S | 0 |
| 52 | NO₂ | H | H | H | S | 0 |
| 53 | N(SO₂CH₃)₂ | H | H | H | O | 0 |
| 54 | OH | H | H | H | O | 0 |
| 55 | OCOCH₃ | H | H | H | O | 0 |
| 56 | OCH₂CH₃ | H | H | H | S | 0 |
| 57 | OCH₃ | H | H | H | O | 0 |
| 58 | OCH₃ | H | H | H | S | 0 |
| 59 | OCH₃ | H | H | Cl | S | 0 |
| 60 | OSO₂CH₃ | H | H | H | O | 0 |
| 61 | H | Br | H | H | S | 0 |
| 62 | H | CF₃ | H | H | S | 0 |
| 63 | H | Cl | H | H | S | 0 |
| 64 | H | CO₂CH₂CH₂CH=CF₂ | H | H | S | 0 |
| 65 | H | CONH₂ | H | H | S | 0 |
| 66 | H | CONHCH₂CH₂CH₃ | H | H | S | 0 |
| 67 | H | CON(CH₃)₂ | H | H | S | 0 |
| 68 | H | COOH | H | H | S | 0 |
| 69 | H | F | H | H | S | 0 |
| 70 | H | NHCOC₆H₅ | H | H | S | 0 |
| 71 | H | OCH₃ | H | H | S | 0 |
| 72 | H | SCH₃ | H | H | S | 0 |
| 73 | H | SO₂C₂H₅ | H | H | O | 0 |
| 74 | H | SO₂CH₃ | H | H | S | 0 |
| 75 | H | SO₂N(C₂H₅)₂ | H | H | O | 0 |
| 76 | H | SO₂N(CH₃)₂ | H | H | S | 0 |
| 77 | H | H | Cl | H | S | 0 |
| 78 | H | H | F | H | O | 0 |
| 79 | H | H | H | CH₃ | O | 0 |
| 80 | H | H | H | NH₂ | O | 0 |
| 81 | H | H | H | NO₂ | O | 0 |
| 82 | H | H | H | OH | O | 0 |
| 83 | H | H | H | OCH₂CH₂F | O | 0 |
| 84 | COOH | H | H | H | O | 0 |
| 85 | NHCHO | H | H | H | O | 0 |
| 86 | SCH₃ | H | H | H | S | 0 |
| 87 | H | Br | H | H | S | 1 |
| 88 | H | Br | H | H | S | 2 |
| 89 | H | Cl | H | H | O | 0 |
| 90 | H | CN | H | H | O | 0 |
| 91 | H | CN | H | H | S | 0 |
| 92 | H | CO₂CH₂CH₂CH=CF₂ | H | H | S | 1 |
| 93 | H | CO₂CH₂CH₂CH=CF₂ | H | H | S | 2 |
| 94 | H | COOH | H | H | O | 0 |
| 95 | H | F | H | H | S | 1 |
| 96 | H | OCF₃ | H | H | S | 0 |

TABLE I-continued

| NO. | $R^1$ | $R^2$ | $R^3$ | $R^4$ | X | n |
|---|---|---|---|---|---|---|
| 97 | H | H | H | COOH | O | 0 |
| 98 | H | H | H | $NHCOC_2H_5$ | O | 0 |
| 99 | H | H | H | $NHSO_2CH_3$ | O | 0 |
| 100 | H | H | H | $OCOC_2H_5$ | O | 0 |
| 101 | H | H | H | $OCH_2CH_2CH=CF_2$ | O | 0 |
| 102 | H | H | H | $OCH_3$ | O | 0 |
| 103 | H | $NH_2$ | H | H | O | 0 |
| 104 | $OCH_2CCl=CH_2$ | H | H | H | O | 0 |
| 105 | $OCH_2CH=CCl_2$ | H | H | H | O | 0 |
| 106 | $OCH_2CO_2C_2H_5$ | H | H | H | O | 0 |
| 107 | CN | H | H | H | O | 0 |
| 108 | $CONH_2$ | H | H | H | O | 0 |
| 109 | $CON(CH_3)C_2H_5$ | H | H | H | O | 0 |
| 110 | $OCH_2CH_2F$ | H | H | H | O | 0 |
| 111 | $OCH_2CH_2CH_3$ | H | H | H | O | 0 |
| 112 | $OCH(CH_3)C_2H_5$ | H | H | H | O | 0 |
| 113 | H | $SCH_3$ | H | H | O | 0 |
| 114 | H | H | $NO_2$ | H | O | 0 |
| 115 | H | $NO_2$ | $NO_2$ | H | O | 0 |
| 116 | H | $CF_3$ | H | H | O | 0 |
| 117 | H | $NO_2$ | H | H | S | 1 |
| 118 | H | $CO_2CH_2CH_2CH=CF_2$ | H | H | O | 0 |
| 119 | H | H | H | $NHCOCF_3$ | O | 0 |
| 120 | $SO_2NH_2$ | H | H | H | S | 0 |
| 121 | H | $SOCH_3$ | H | H | S | 0 |
| 122 | H | $CONHCH_3$ | H | H | S | 0 |
| 123 | H | $SO_2NHCH_3$ | H | H | S | 0 |
| 124 | H | $SO_2C_2H_5$ | H | H | S | 0 |
| 125 | H | $CSNH_2$ | H | H | S | 0 |
| 126 | H | $NO_2$ | H | H | S | 0 |
| 127 | H | H | $NO_2$ | H | S | 0 |
| 128 | —O—$CH_2$—O— | | H | H | S | 0 |
| 129 | $SO_2F$ | H | H | H | S | 0 |
| 130 | H | H | H | $OCH_3$ | S | 0 |
| 131 | $OCH_3$ | $OCH_3$ | H | H | S | 0 |
| 164 | —CH=CH—CH=CH— | | H | H | S | 1 |
| 165 | 1-$CH_3$-$^cC_3H_5$ | H | H | H | O | 0 |
| 166 | Br | H | H | H | O | 0 |
| 167 | Br | H | H | H | S | 0 |
| 168 | C≡CH | H | H | H | O | 0 |
| 169 | $C_6H_5$ | H | H | H | O | 0 |
| 170 | $C_6H_5$ | H | H | H | S | 0 |
| 171 | $^cC_3H_5$ | H | H | H | O | 0 |
| 172 | $^cC_3H_5$ | H | H | H | S | 0 |
| 173 | $CF_2H$ | H | H | H | O | 0 |
| 174 | $CF_2H$ | H | H | H | S | 0 |
| 175 | $CF_3$ | H | H | H | O | 0 |
| 176 | $CF_3$ | H | H | H | S | 0 |
| 177 | $CH_2CH=CH_2$ | H | H | H | O | 0 |
| 178 | $CH_2CH=CH_2$ | H | H | H | S | 0 |
| 179 | $CH_2CH_2F$ | H | H | H | O | 0 |
| 180 | $CH_2CH_2F$ | H | H | H | S | 0 |
| 181 | $CH_2CH_2$ | H | H | H | O | 0 |
| 182 | $CH_2CH_3$ | H | H | H | S | 0 |
| 183 | $CH_2OH$ | H | H | H | O | 0 |
| 184 | $CH_2OH$ | H | H | H | S | 0 |
| 185 | $CH_3$ | $CH_3$ | H | H | S | 0 |
| 186 | $CH_3$ | H | H | H | O | 1 |
| 187 | $CH_3$ | H | H | H | O | 2 |
| 188 | $CH_3$ | H | H | H | S | 1 |
| 189 | $CH_3$ | H | H | H | S | 2 |
| 190 | Cl | Cl | H | H | O | 0 |
| 191 | Cl | H | H | H | O | 1 |
| 192 | Cl | H | H | H | S | 1 |
| 193 | CN | H | H | H | S | 0 |
| 194 | $CO_2CH_2CH_2CH=CF_2$ | H | H | H | O | 0 |
| 195 | $CO_2CH_2CH_2CH=CF_2$ | H | H | H | O | 1 |
| 196 | $CO_2CH_2CH_2CH=CF_2$ | H | H | H | O | 2 |
| 197 | $CO_2CH_2CH_2CH=CF_2$ | H | H | H | S | 0 |
| 198 | $CO_2CH_2CH_2CH=CF_2$ | H | H | H | S | 1 |
| 199 | $CO_2CH_2CH_2CH=CF_2$ | H | H | H | S | 2 |
| 200 | $CO_2CH_2CH_2F$ | H | H | H | O | 0 |
| 201 | $CO_2CH_2CH_2F$ | H | H | H | S | 0 |
| 202 | $CO_2CH_3$ | H | H | H | O | 1 |
| 203 | $CO_2CH_3$ | H | H | H | O | 2 |
| 204 | $CO_2CH_3$ | H | H | H | S | 0 |
| 205 | $CO_2CH_3$ | H | H | H | S | 1 |
| 206 | $CO_2CH_3$ | H | H | H | S | 2 |
| 207 | $COCH_3$ | H | H | H | O | 0 |
| 208 | $COCH_3$ | H | H | H | S | 0 |
| 209 | $CON(CH_3)_2$ | H | H | H | O | 0 |

TABLE I-continued

| NO. | R¹ | R² | R³ | R⁴ | X | n |
|---|---|---|---|---|---|---|
| 210 | CON(CH₃)₂ | H | H | H | S | 0 |
| 211 | CON(CH₃)C₂H₅ | H | H | H | S | 0 |
| 212 | CONH₂ | H | H | H | S | 0 |
| 213 | CONHCH₂C₆H₅ | H | H | H | O | 0 |
| 214 | CONHCH₂C₆H₅ | H | H | H | S | 0 |
| 215 | CONHCH₂CH₂CF=CF₂ | H | H | H | O | 0 |
| 216 | CONHCH₂CH₂CF=CF₂ | H | H | H | S | 0 |
| 217 | CONHCH₂CH₂CH₃ | H | H | H | O | 0 |
| 218 | CONHCH₂CH₂CH₃ | H | H | H | S | 0 |
| 219 | CONHCH₃ | H | H | H | O | 0 |
| 220 | CONHCH₃ | H | H | H | S | 0 |
| 221 | CONHSO₂CH₃ | H | H | H | O | 0 |
| 222 | CONHSO₃CH₃ | H | H | H | S | 0 |
| 223 | COSCH₂CH₂CH=CF₂ | H | H | H | O | 0 |
| 224 | COSCH₂CH₂CH=CF₂ | H | H | H | S | 0 |
| 225 | CSNH₂ | H | H | H | O | 0 |
| 226 | CSNH₂ | H | H | H | S | 0 |
| 227 | F | Cl | H | H | S | 0 |
| 228 | I | H | H | H | O | 0 |
| 229 | I | H | H | H | O | 0 |
| 230 | I | H | H | H | S | 0 |
| 231 | N(SO₂CH₃)₂ | H | H | H | S | 0 |
| 232 | NHCHO | H | H | H | S | 0 |
| 233 | NHCOC₂H₅ | H | H | H | O | 0 |
| 234 | NHCOC₆H₅ | H | H | H | O | 0 |
| 235 | NHSO₂CH₃ | H | H | H | O | 0 |
| 236 | NO₂ | H | H | H | O | 1 |
| 237 | NO₂ | H | H | H | O | 2 |
| 238 | OCF₂CF₂H | H | H | H | O | 0 |
| 239 | OCF₂CF₂H | H | H | H | S | 0 |
| 240 | OCF₂H | H | H | H | O | 0 |
| 241 | OCF₂H | H | H | H | O | 1 |
| 242 | OCF₂H | H | H | H | O | 2 |
| 243 | OCF₂H | H | H | H | S | 0 |
| 244 | OCF₂H | H | H | H | S | 1 |
| 245 | OCF₂H | H | H | H | S | 2 |
| 246 | OCF₃ | H | H | H | O | 0 |
| 247 | OCF₃ | H | H | H | S | 0 |
| 248 | OCH(CH₃)C₂H₅ | H | H | H | S | 0 |
| 249 | OCH₂CCl=CH₂ | H | H | H | S | 0 |
| 250 | OCH₂CF₃ | H | H | H | O | 0 |
| 251 | OCH₂CF₃ | H | H | H | S | 2 |
| 252 | OCH₂CH=CCl₂ | H | H | H | S | 0 |
| 253 | OCH₂CH=CH₂ | H | H | H | S | 0 |
| 254 | OCH₂CH₂CH=CF₂ | H | H | H | S | 0 |
| 255 | OCH₂CH₂CH₃ | H | H | H | S | 0 |
| 256 | OCH₂CH₂F | H | H | H | S | 0 |
| 257 | OCH₂CH₃ | H | H | H | O | 0 |
| 258 | OCH₂CH₃ | H | H | H | O | 1 |
| 259 | OCH₂CO₂C₂H₅ | H | H | H | S | 0 |
| 260 | OCH₃ | H | H | Cl | O | 0 |
| 261 | OCH₃ | H | NHCOCH₃ | H | S | 0 |
| 262 | OCH₃ | H | OCH₃ | H | S | 0 |
| 263 | OCOCH₃ | H | H | H | S | 0 |
| 264 | OH | F | H | H | S | 0 |
| 265 | OH | H | Cl | H | O | 0 |
| 266 | OH | H | H | H | S | 0 |
| 267 | OSO₂CH₃ | H | H | H | S | 0 |
| 268 | SCF₃ | H | H | H | O | 0 |
| 269 | SCF₃ | H | H | H | S | 0 |
| 270 | SCH₂CH₂CH₃ | H | H | H | O | 0 |
| 271 | SCH₂CH₂CH₃ | H | H | H | S | 0 |
| 272 | SCH₃ | H | H | H | O | 0 |
| 273 | SO₂C₂H₅ | H | H | H | O | 0 |
| 274 | SO₂C₂H₅ | H | H | H | S | 0 |
| 275 | SO₂CF₃ | H | H | H | O | 0 |
| 276 | SO₂CF₃ | H | H | H | S | 0 |
| 277 | SO₂CH₃ | H | H | H | O | 0 |
| 278 | SO₂CH₃ | H | H | H | S | 0 |
| 279 | SO₂F | H | H | H | O | 0 |
| 280 | SO₂N(C₂H₅)₂ | H | H | H | O | 0 |
| 281 | SO₂N(C₂H₅)₂ | H | H | H | S | 0 |
| 282 | SO₂N(CH₃)₂ | H | H | H | O | 0 |
| 283 | SO₂N(CH₃)₂ | H | H | H | S | 0 |
| 284 | SO₂NH₂ | H | H | H | O | 0 |
| 285 | SO₂NHCH₃ | H | H | H | O | 0 |
| 286 | SO₂NHCH₃ | H | H | H | S | 0 |
| 287 | SOCF₃ | H | H | H | O | 0 |
| 288 | SOCF₃ | H | H | H | S | 0 |
| 289 | SOCH₃ | H | H | H | O | 0 |
| 290 | SOCH₃ | H | H | H | S | 0 |

TABLE I-continued

| NO. | R¹ | R² | R³ | R⁴ | X | n |
|---|---|---|---|---|---|---|
| 291 | H | * | H | * | S | 0 |
| | | ** indicates a fused —CH=CH—CH=CH— link | | | | |
| 292 | H | 1-CH₃-ᶜC₃H₅ | H | H | O | 0 |
| 293 | H | 1-CH₃-ᶜC₃H₅ | H | H | S | 0 |
| 294 | H | Br | H | H | O | 0 |
| 295 | H | Br | H | H | O | 1 |
| 296 | H | Br | H | H | O | 2 |
| 297 | H | C≡CH | H | H | O | 0 |
| 298 | H | C₆H₅ | H | H | S | 0 |
| 299 | H | ᶜC₃H₅ | H | H | S | 0 |
| 300 | H | CF₂H₂ | H | H | O | 0 |
| 301 | H | CF₂H₂ | H | H | S | 0 |
| 302 | H | CH₂CH=CH₂ | H | H | O | 0 |
| 303 | H | CH₂CH₂F | H | H | O | 0 |
| 304 | H | CH₂CH₂F | H | H | S | 0 |
| 305 | H | CH₂CH₃ | H | H | O | 0 |
| 306 | H | CH₂CH₃ | H | H | S | 0 |
| 307 | H | CH₂OH | H | H | O | 0 |
| 308 | H | CH₂OH | H | H | S | 0 |
| 309 | H | CHO | H | H | O | 0 |
| 310 | H | CHO | H | H | S | 0 |
| 311 | H | Cl | H | H | O | 1 |
| 312 | H | CO₂CH₂CH₂CH=CF₂ | H | H | O | 1 |
| 313 | H | CO₂CH₂CH₂CH=CF₂ | H | H | O | 2 |
| 314 | H | CO₂CH₂CH₂F | H | H | S | 0 |
| 315 | H | CO₂CH₂CH₃ | H | H | O | 0 |
| 316 | H | CO₂CH₂CH₃ | H | H | S | 0 |
| 317 | H | CO₂CH₃ | H | H | S | 0 |
| 318 | H | COCH₃ | H | H | O | 0 |
| 319 | H | CON(CH₃)₂ | H | H | O | 0 |
| 320 | H | CON(CH₃)C₂H₅ | H | H | O | 0 |
| 321 | H | CON(CH₃)C₂H₅ | H | H | S | 0 |
| 322 | H | CONHCH₂C₆H₅ | H | H | S | 0 |
| 323 | H | CONHCH₂CH₂CH=CF₂ | H | H | O | 0 |
| 324 | H | CONHCH₂CH₂CH=CF₂ | H | H | S | 0 |
| 325 | H | CONHCH₂CH₂CH₃ | H | H | O | 0 |
| 326 | H | CONHCH₃ | H | H | O | 0 |
| 327 | H | CONHSO₂CH₃ | H | H | O | 0 |
| 328 | H | CONHSO₂CH₃ | H | H | S | 0 |
| 329 | H | COSCH₂CH₂CH=CF₂ | H | H | O | 0 |
| 330 | H | COSCH₂CH₂CH=CF₂ | H | H | S | 0 |
| 331 | H | CSNH₂ | H | H | O | 0 |
| 332 | H | F | H | H | O | 1 |
| 333 | H | F | H | H | O | 2 |
| 334 | H | F | F | H | S | 0 |
| 335 | H | I | H | H | O | 0 |
| 336 | H | N(SO₂CH₃)₂ | H | H | O | 0 |
| 337 | H | N(SO₂CH₃)₂ | H | H | S | 0 |
| 338 | H | NH₂ | H | H | S | 0 |
| 339 | H | NHCHO | H | H | O | 0 |
| 340 | H | NHCHO | H | H | S | 0 |
| 341 | H | NHCOC₂H₅ | H | H | O | 0 |
| 342 | H | NHCOC₂H₅ | H | H | S | 0 |
| 343 | H | NHCOC₆H₅ | H | H | O | 0 |
| 344 | H | NHCOCH₃ | H | H | O | 0 |
| 345 | H | NHCOCH₃ | H | H | S | 0 |
| 346 | H | NHSO₂CH₃ | H | H | O | 0 |
| 347 | H | NHSO₂CH₃ | H | H | S | 0 |
| 348 | H | NO₂ | H | H | O | 1 |
| 349 | H | NO₂ | NO₂ | H | S | 0 |
| 350 | H | OCF₂CF₂H | H | H | O | 0 |
| 351 | H | OCF₂CF₂H | H | H | S | 0 |
| 352 | H | OCF₂H | H | H | O | 0 |
| 353 | H | OCF₂H | H | H | O | 1 |
| 354 | H | OCF₂H | H | H | O | 2 |
| 355 | H | OCF₂H | H | H | S | 0 |
| 356 | H | OCF₂H | H | H | S | 1 |
| 357 | H | OCF₂H | H | H | S | 2 |
| 358 | H | OCF₃ | H | H | O | 0 |
| 359 | H | OCH(CH₃)C₂H₅ | H | H | O | 0 |
| 360 | H | OCH(CH₃)C₂H₅ | H | H | S | 0 |
| 361 | H | OCH₂CCl=CH₂ | H | H | O | 0 |
| 362 | H | OCH₂CCl=CH₂ | H | H | S | 0 |
| 363 | H | OCH₂CF₃ | H | H | O | 0 |
| 364 | H | OCH₂CF₃ | H | H | S | 0 |
| 365 | H | OCH₂CH=CCl₂ | H | H | O | 0 |
| 366 | H | OCH₂CH=CCl₂ | H | H | S | 0 |
| 367 | H | OCH₂CH=CH₂ | H | H | O | 0 |
| 368 | H | OCH₂CH=CH₂ | H | H | S | 0 |
| 369 | H | OCH₂CH₂CH=CF₂ | H | H | O | 0 |
| 370 | H | OCH₂CH₂CH=CF₂ | H | H | S | 0 |

TABLE I-continued

| NO. | R$^1$ | R$^2$ | R$^3$ | R$^4$ | X | n |
|---|---|---|---|---|---|---|
| 371 | H | OCH$_2$CH$_2$CH$_3$ | H | H | O | 0 |
| 372 | H | OCH$_2$CH$_2$CH$_3$ | H | H | S | 0 |
| 373 | H | OCH$_2$CH$_2$F | H | H | O | 0 |
| 374 | H | OCH$_2$CH$_2$F | H | H | S | 0 |
| 375 | H | OCH$_2$CH$_3$ | H | H | O | 0 |
| 376 | H | OCH$_2$CH$_3$ | H | H | O | 0 |
| 377 | H | OCH$_2$CH$_3$ | H | H | S | 0 |
| 378 | H | OCH$_2$CH$_3$ | H | H | S | 0 |
| 379 | H | OCH$_2$CO$_2$C$_2$H$_5$ | H | H | O | 0 |
| 380 | H | OCH$_2$CO$_2$C$_2$H$_5$ | H | H | S | 0 |
| 381 | H | OCH$_3$ | H | H | O | 1 |
| 382 | H | OCH$_3$ | H | H | O | 2 |
| 383 | H | OCH$_3$ | H | H | S | 1 |
| 384 | H | OCH$_3$ | H | H | S | 2 |
| 385 | H | OCOCH$_3$ | H | H | O | 0 |
| 386 | H | OCOCH$_3$ | H | H | S | 0 |
| 387 | H | OH | H | H | S | 0 |
| 388 | H | OSO$_2$CH$_3$ | H | H | O | 0 |
| 389 | H | OSO$_2$CH$_3$ | H | H | S | 0 |
| 390 | H | SCF$_3$ | H | H | O | 0 |
| 391 | H | SCF$_3$ | H | H | O | 1 |
| 392 | H | SCF$_3$ | H | H | O | 2 |
| 393 | H | SCH$_2$CH$_2$CH$_3$ | H | H | O | 0 |
| 394 | H | SO$_2$CF$_3$ | H | H | O | 0 |
| 395 | H | SO$_2$CH$_3$ | H | H | O | 0 |
| 396 | H | SO$_2$F | H | H | O | 0 |
| 397 | H | SO$_2$F | H | H | S | 0 |
| 398 | H | SO$_2$N(C$_2$H$_5$)$_2$ | H | H | S | 0 |
| 399 | H | SO$_2$N(CH$_3$)$_2$ | H | H | O | 0 |
| 400 | H | SO$_2$NH$_2$ | H | H | O | 0 |
| 401 | H | SO$_2$NH$_2$ | H | H | S | 0 |
| 402 | H | SO$_2$NHCH$_3$ | H | H | O | 0 |
| 403 | H | SOCF$_3$ | H | H | O | 0 |
| 404 | H | SOCH$_3$ | H | H | O | 0 |
| 405 | H | H | H | Cl | O | 0 |
| 406 | H | H | H | CO$_2$CH$_3$ | S | 0 |
| 407 | H | H | H | CONHCH$_2$C$_6$H$_5$ | S | 0 |
| 408 | H | H | H | COOH | S | 0 |
| 409 | H | H | H | NH$_2$ | S | 0 |
| 410 | H | H | H | NHCOC$_2$H$_5$ | S | 0 |
| 411 | H | H | H | NHCOCF$_3$ | S | 0 |
| 412 | H | H | H | NHSO$_2$CH$_3$ | S | 0 |
| 413 | H | H | H | NO$_2$ | S | 0 |
| 414 | H | H | H | OCH$_2$CH$_2$CH=CF$_2$ | S | 0 |
| 415 | H | H | H | OCH$_2$CH$_2$F | S | 0 |
| 416 | H | H | H | OCOC$_2$H$_5$ | S | 0 |
| 417 | H | H | H | OH | S | 0 |
| 418 | H | H | Br | H | O | 0 |
| 419 | H | H | CH$_2$OCH$_3$ | H | O | 0 |
| 420 | H | H | COOH | H | O | 0 |
| 421 | H | H | OCH$_3$ | H | O | 0 |
| 422 | H | H | OH | H | O | 0 |
| 423 | H | H | CN | H | O | 1 |
| 424 | H | H | OCH$_3$ | H | O | 1 |
| 425 | H | H | F | H | O | 2 |
| 426 | H | H | OCH$_3$ | H | O | 2 |
| 427 | H | H | $^c$C$_3$H$_5$ | H | S | 0 |
| 428 | H | H | CH$_2$CH=CH$_2$ | H | S | 0 |
| 429 | H | H | CH$_3$ | H | S | 0 |
| 430 | H | H | CO$_2$CH$_3$ | H | S | 0 |
| 431 | H | H | COOH | H | S | 0 |
| 432 | H | H | F | H | S | 0 |
| 433 | H | H | OCH$_3$ | H | S | 0 |
| 434 | H | H | OH | H | S | 0 |
| 435 | H | H | CN | H | S | 1 |
| 436 | H | H | OCH$_3$ | H | S | 1 |
| 437 | H | H | H | H | S | 2 |
| 438 | H | H | OCG$_3$ | H | S | 2 |
| 439 | CH=CH$_2$ | H | H | H | S | 0 |
| 440 | CH=CH$_2$ | H | H | H | O | 0 |
| 441 | H | CH=CH$_2$ | H | H | O | 0 |
| 442 | H | CH=CH$_2$ | H | H | S | 0 |

$^c$indicates a cyclic substituent.

Compounds of Formula (I) wherein R$^1$, R$^2$, R$^3$, R$^4$, X and Z have any of the meanings given above and n is 0, may be prepared by dehydrobromination of the corresponding compound of Formula (III), for example by treatment of the compound of Formula (III) with a base such as an alkali metal hydroxide, for example potassium or sodium hydroxide, or a tertiary amine, for example 1,8-diazabicyclo[5.4.0]undec-7-ene, in the presence of an inert solvent, for example dimethylformamide. Compounds of Formula (III) may be prepared from the corresponding mercapto (thiol) compound of Formula (II) by reaction of the compound of Formula (II) with a compound of Formula (IV), wherein L is a readily displaceable leaving group such as iodo, methanesulphonyloxy and especially para-toluenesulphonyloxy, under conditions well known in the art for such displacement reactions, for example in the presence of a mild base such as an alkali metal carbonate, for example potassium or sodium carbonate, in an inert solvent, at a temperature in the range from 40° C. to 100° C., and most conveniently at the reflux temperature of a suitable inert solvent such as acetone which has a boiling point within this range. Compounds of Formula (IV) may be prepared by the following sequence of reactions. Acrylic acid ($CH_2$=$CHCO_2H$, commercially available) is reacted with dibromodifluoromethane ($CF_2Br_2$) under the conditions described by Rong and Keese in Tetrahedon Letters, 1990, page 5615, in the presence of acetonitrile, water, sodium dithionite ($Na_2S_2O_4$) and sodium bicarbonate, to give the compound of Formula (V). The compound of Formula (VI) is then prepared by reduction of the compound of Formula (V) under conditions well known in the art for the reduction of an acid group to a primary alcohol, for example using lithium aluminium hydride in the presence of an inert solvent such as tetrahydrofuran. Compounds of Formula (IV) may then be prepared from the compound of Formula (VI) by standard methods for the conversion of a primary hydroxyl group to a displaceable leaving group. In the case of compounds of Formula (IV) where L is methanesulphonyloxy or para-toluenesulphonyloxy, the compound of Formula (VI) may be reacted with methanesulphonyl chloride or para-toluenesulphonyl chloride. In the case of the compound of Formula (IV) where L is iodo, the compound of Formula (VI) may be reacted with an alkali metal iodide, for example sodium or potassium iodide, under acidic conditions.

A preferred method for the preparation of compounds of Formula (I) wherein $R^1$, $R^2$, $R^3$, $R^4$, X and Z have any of the meanings given above and n is 0, is by reaction of a compound of Formula (II) with a compound of Formula (VII) wherein $R^a$ is a $C_{1-4}$ alkyl group, especially methyl, or a phenyl group optionally substituted with a $C_{1-4}$ alkyl group, especially para-tolyl, under conditions well known in the art for such displacement reactions, for example in the presence of a mild base such as an alkali metal carbonate, for example potassium or sodium carbonate, in an inert solvent, at a temperature in the range from 40° C. to 100° C., and most conveniently at the reflux temperature of a suitable inert solvent such as acetone which has a boiling point within this range. Compounds of Formula (VII) may be prepared by the following sequence of reactions. Hydrogen bromide is reacted with the commercially available compound of Formula (VIII) under standard conditions for an addition reaction, for example by passing hydrogen bromide gas through a solution of the compound of Formula (VIII) in an inert solvent to give the compound of Formula (IX). The compound of Formula (IX) is then reacted with the silver salt of a sulphonic acid of Formula $R^aSO_3H$, wherein $R^a$ has the meaning given above, for example the silver salt of para-toluenesulphonic acid (silver rosylate), preferably in an inert solvent in the absence of light, to give the corresponding compound of Formula (X). Debromofluorination of the compound of Formula (X), for example by reaction with zinc, preferably in the presence of a suitable catalyst such as iodine, gives the compound (VII), wherein $R^a$ has the meanings given above.

A further method for the preparation of compounds of Formula (I) wherein $R^1$, $R^2$, $R^3$, $R^4$, X and Z have any of the meanings given above and n is 0, is provided by reaction of a compound of Formula (II) with the compound of Formula (IX), for example in the presence of a base such as an alkali metal carbonate, for example sodium or potassium carbonate, in an inert solvent, to give the corresponding compound of Formula (XI), wherein $R^1$, $R^2$, $R^3$, $R^4$, X and Z have any of the meanings given above. The compound of Formula (XI) may then be converted to the corresponding compound of Formula (I) by a debromofluorination reaction as described above for the preparation of a compound of formula (VII) from the corresponding compound of Formula (X). A further method of preparation of compounds of formula (I) where $R^1$, $R^2$, $R^3$, $R^4$, X and Z have the meanings given above and n is 0 is analogous to that of Hayashi et al, Chemistry Letters, 1979, p983–986 which discloses the reaction of an aldehyde with the appropriately halogenated methane in the presence of zinc dust and triphenylphosphine in dimethylacetamide to give vinyl halides. Thus, the first step comprises reacting a correspondingly substituted benzoxazole or benzthiazole of formula (II) with 2-(2-bromoethyl)-1,3-dioxolane to form the corresponding dioxolane in the presence of a base such as a carbonate, for example, potassium carbonate, and an inert solvent, for example acetone. The second step comprises treating the dioxolane with aqueous acid, for example hydrochloric acid in the presence or absence of an inert co-solvent, for example, tetrahydrofuran, to form the corresponding oxopropylthiobenzoxazole or benzthiazole. Lastly, the oxopropylthiobenzoxazole or benzthiazole is then reacted with dibromodifluoromethane in an inert solvent, for example, dimethylacetamide, in the presence of a phosphine agent, for example, triphenylphosphine and zinc dust. Both the compounds of formula (II), 2-(2-bromoethyl)-1,3-dioxolane and dibromodifluoromethane can be obtained by conventional methods as described herein or from commercial sources.

In a further aspect therefore, the invention provides a process for the preparation of a compound of Formula (I) wherein $R^1$, $R^2$, $R^3$, $R^4$, X and Z have any of the meanings given hereinbefore and n is 0, which comprises the step of reaction of the corresponding compound of Formula (II) with a compound of Formula (IV) wherein L is a readily displaceable leaving group, to give a compound of Formula (III) followed by the step of dehydrobromination of the compound of Formula (III) in the presence of a base.

In a further aspect the invention provides a process for the preparation of a compound of Formula (I) wherein $R^1$, $R^2$, $R^3$, $R^4$, X and Z have any of the meanings given hereinbefore and n is 0, which comprises reaction of a compound of Formula (II) with a compound of Formula (VII) wherein $R^a$ is a $C_{1-4}$ alkyl group or a phenyl group optionally substituted with a $C_{1-4}$ alkyl group.

In a further aspect the invention provides a process for the preparation of a compound of Formula (I) wherein $R^1$, $R^2$, $R^3$, $R^4$, X and Z have any of the meanings given hereinbefore and n is 0, which comprises the step of reaction of a compound of Formula (II) with the compound of Formula (IX) to give a compound of Formula (XI), followed by the step of debromofluorination of the compound of Formula (XI).

Many compounds of Formula (I) as described herein may also be prepared from other compounds of Formula (I) by transformation of the appropriate $R^1$, $R^2$, $R^3$ and $R^4$ substituents using standard chemical procedures. Many such procedures are described in the experimental examples, and are often generally applicable to similar transformations, thereby providing by analogy yet further procedures for the preparation of the appropriate compounds of Formula (I).

It will be appreciated by those skilled in the art that compounds of Formula (II) exist in tautomeric equilibrium between the equivalent 2-mercapto and 2-thione forms. For the sake of convenience, the compounds are referred to herein in their 2-mercapto form unless otherwise stated. Compounds of Formulas (III), (IV), (VII), (X) and (XI) have not been previously reported. In five further aspects, therefore, the invention provides: a compound of Formula (III) wherein $R^1$, $R^2$, $R^3$, $R^4$, X and Z have any of the meanings given hereinbefore; a compound of Formula (IV) wherein L is a readily displaceable leaving group; a compound of Formula (VII) wherein $R^a$ is a $C_{1-4}$ alkyl group or a phenyl group optionally substituted with a $C_{1-4}$ alkyl group; a compound of Formula (X) wherein $R^a$ is a $C_{1-4}$ alkyl group or a phenyl group optionally substituted with a $C_{1-4}$ alkyl group; and a compound of Formula (XI) wherein $R^1$, $R^2$, $R^3$, $R^4$, X and Z have any of the meanings given hereinbefore.

Compounds of Formula (II) are commercially available or may be prepared from commercially available precursors by standard procedures well known in the art. Typical procedures suitable for the preparation of many of the relevant compounds of Formula (II) and their precursors may be found in the following standard references: Comprehensive Heterocyclic Chemistry (Published by Pergamon, Edited by Katritzky and Rees), 1984, e.g. pages 177-331; Journal of Organic Chemistry, 19, 758-766 (1954); Heterocyclic Compounds (Published by Wiley, Edited by Elderfield), Volume 5; Organic Compounds of Sulphur, Selenium and Tellurium (Published by The Chemical Society, Specialist Reports), Volumes 3, 4 and 5; Warburton et al, Chemical Reviews, 57, 1011-1020 (1957). By way of example, many of the compounds of formula (II) where X is oxygen may be prepared by reacting a correspondingly substituted 2-aminophenol or a salt thereof, with thiophosgene or carbon disulphide, in an inert solvent such as diethyl ether or chloroform, and optionally in the presence of a base, such as potassium carbonate or triethylamine, and/or water. Also by way of example, many of the compounds of formula (II) where X is sulphur may be prepared by the Herz Reaction (Warburton et al, Chemical Reviews, 57, 1011-1020 (1957)) in which appropriately substituted anilines are reacted sequentially with disulphur dichloride and aqueous sodium hydroxide to produce the corresponding 2-mercapto aniline derivative, which is then reacted with carbon disulphide to produce the 2-mercaptobenzthiazole of formula (II). Benzthiazoles of formula (II) may also be prepared from appropriately substituted N-phenylthioureas by oxidation (for example in the presence of molecular bromine) and replacement of the amino group of the resulting 2-aminobenzthiazole with a 2-mercapto group by reaction with a base and carbon disulphide or by diazotisation, reaction with a halide and displacement of the 2-halo group using NaSH or thiourea. N-phenylthioureas are available by reaction of the corresponding anilines with ammonium thiocyanate. Compounds of Formula (II) may also be prepared by reaction of the correspondingly substituted 2-halonitrobenzene by reaction with sodium sulphide, sulphur ($S_8$), and carbon disulphide, or by reaction of the correspondingly substituted phenyl isothiocyanate with sulphur ($S_8$) to produce the corresponding benzthiazole. All of these reactions are well documented in the chemical literature. The choice of the appropriate procedure will depend upon the particular nuclear substitution pattern required and is within the normal skill of the art.

Examples of these and many other procedures for the preparation of the compounds of Formula (II) are provided in the experimental examples. For any given compound of Formula (I) as herein described the appropriate starting materials may be prepared by these or directly analogous procedures. Suitable procedures are also described in the experimental examples for the preparation of other starting materials and intermediates for the various processes described herein, to provide access directly or by analogy to any such starting material or intermediate which is not readily available commercially.

The compounds of formula (I) where $R^1$, $R^2$, $R^3$, $R^4$ and X have the meanings defined above and n is 1 or 2, are prepared by oxidising the correspondingly substituted compound of formula (I) when n is 0, using conventional methods, for example by treatment with a suitable oxidising agent in an inert organic solvent. In general, oxidation of a compound of Formula (I) with one equivalent of a suitable oxidising agent provides the corresponding compound wherein n is 1, and oxidation using two equivalents of the oxidising agent provides the corresponding compound wherein n is 2. Suitable oxidising agents include organic and inorganic peroxides such as peroxy carboxylic acids, or their salts, for example, meta-chloroperbenzoic acid, perbenzoic acid, magnesium monoperoxy-phthalic acid, potassium peroxymono-sulphate or sodium periodate.

Thus, according to a further aspect of the present invention there is provided a process for the preparation of compounds of formula (I) where n is 1 or 2 and $R^1$, $R^2$, $R^3$, $R^4$, X and Z have the meanings defined above which comprises oxidation of the correspondingly substituted compound of formula (I) when n is 0.

The compounds of formula (I) are nematicidal and can be used to control nematodes in crop plants. Therefore, in a further aspect of the invention, there is provided a method for killing or controlling nematodes which comprises applying to the locus of the pests or to a plant susceptible to attack by the pest an effective amount of a compound of formula (I) as defined herein.

The term "controlling" extends to non-lethal effects which result in the prevention of damage to the host plant and the limitation of nematode population increase. These effects may be the result of chemical induced disorientation, immobilisation, or hatch prevention or induction. The chemical treatment may also have deleterious effects on nematode development or reproduction.

The compounds of the invention can be used against both plant- parasitic nematodes and nematodes living freely in the soil. Examples of plant-parasitic nematodes are: ectoparasites, for example *Xiphinema spp.*, *Longidorus spp.* and *Trichodorous spp.*; semi-endoparasites, for example, *Tylenchulus spp.*; migratory endoparasites, for example, *Pratylenchus spp.*, *Radopholus spp.* and *Scutellonema spp.*; sedentary endoparasites, for example, *Heterodera spp.*, *Globodera spp.* and *Meloidogyne spp.*;

and stem and leaf endoparasites, for example, *Ditylenchus spp., Aphelenchoides spp.* and *Hirshmaniella spp.*.

The compounds of formula (I) display nematicidal activity against different types of nematodes including the cyst nematode. The compounds of formula (I) may also be used to combat and control infestations of insect pests such as Lepidoptera, Diptera, Homoptera and Coleoptera (including Diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of Formula (I) include:

*Myzus persicae* (aphid)
*Aphis gossypii* (aphid)
*Aphis fabae* (aphid)
*Megoura viceae* (aphid)
*Aedes aegypti* (mosquito)
*Anopheles spp.* (mosquitos)
*Culex spp.* (mosquitos)
*Dysdercus fasciatus* (capsid)
*Musca domestica* (housefly)
*Pieris brassicae* (white butterfly)
*Plutella maculipennis* (diamond back moth)
*Phaedon cochleariae* (mustard beetle)
*Aonidiella spp.* (scale insects)
*Trialeuroides spp.* (white flies)
*Bemisia tabaci* (white fly)
*Blattella germanica* (cockroach)
*Periplaneta americana* (cockroach)
*Blatta orientalis* (cockroach)
*Spodoptera littoralis* (cotton leafworm)
*Hellothis virescens* (tobacco budworm)
*Chortiocetes terminifera* (locust)
*Diabrotica spp.* (rootworms)
*Agrotis spp.* (cutworms)
*Chilo partellus* (maize stem borer)
*Nilaparvata lugens* (planthopper)
*Nephotettix cincticeps* (leafhopper)
*Panonychus ulmi* (European red mite)
*Panonychus citri* (citrus red mite)
*Tetranychus urticae* (two-spotted spider mite)
*Tetranychus cinnabarinus* (carmine spider mite)
*Phyllcoptruta oleivora* (citrus rust mite)
*Polyphagotarsonemus latus* (broad mite)
*Brevipalpus spp.* (mites)

In order to apply the compound to the locus of the nematode, insect or acarid pest, or to a plant susceptible to attack by the nematode, insect or acarid pest, the compound is usually formulated into a composition which includes in addition to the compound of formula (I) suitable inert diluent or carrier materials, and/or surface active agents. Thus in two further aspects of the invention there is provided a nematicidal, insecticidal or acaricidal composition comprising an effective amount of a compound of formula (I) as defined herein and an inert diluent or carrier material and optionally a surface active agent.

The amount of composition generally applied for the control of nematode pests gives a rate of active ingredient from 0.01 to 10 kg per hectare, preferably from 0.1 to 6 kg per hectare.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonire, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fullers earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated. For agricultural or horticultural purposes, an aqueous preparation containing between 0.0001% and 0.1% by weight of the active ingredient (approximately equivalent to from 5–2000 g/ha) is particularly useful.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 1–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water disperible powder WS) or liquids (flowable concentrate FS, liquid seed treatment LS), or microcapsule suspensions CS for use in seed treatments. The formulations can be applied to the seed by standard techniques and through conventional seed treaters. In use the compositions are applied to the nematodes, to the locus of the nematodes, to the habitat of the nematodes, or to growing plants liable to infestation by the nematodes, by any of the known means of applying pesticidal compositions, for example, by dusting, spraying, or incorporation of granules.

The compounds of the invention may be the sole active ingredient of the composition or they may be admixed with one or more additional active ingredients such as nematicides or agents which modify the behaviour of nematodes such as hatching factors, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulphothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulphan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avermectins or milbemycins, for example such as abamectin, avermectin, and milbemycin;

g) Hormones and pheromones;

h) Organochlorine compounds such as benzene hexachloride, DDT, endosulphan, chlordane or dieldrin;

i) Amidines, such as chlordimeform or amitraz;

j) Fumigant agents;

k) nitromethylenes such as imidacloprid.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylon, cyromazin, methoprene, chlorfluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

Compounds of Formula (I) according to the invention also show fungicidal activity and may be used to control one or more of a variety of plant pathogens. In a further aspect the invention therefore includes a method of combating fungi which comprises applying to a plant, to a seed of a plant or to the locus of the plant or seed a fungicidally effective amount of a compound as herein defined or a composition containing the same. The invention further includes a fungicidal composition comprising a fungicidally effective amount of a compound as herein defined and a fungicidally acceptable carrier or diluent therefor.

Examples of plant pathogens which the compounds or fungicidal compositions of the invention may control, methods by which fungi may be combatted and the form of suitable compositions, including acceptable carriers ad diluents, adjuvants such as wetting, dispersing, emulsifying and suspending agents, and other ingredients, such as fertilisers and other biologically active materials, are described, for instance, in International application No WO 93/08180, the content of which is incorporated herein by reference.

The invention is illustrated by the following Examples in which percentages are by weight and the following abbreviations are used: gc=gas chromatography; nmr=nuclear magnetic resonance; s=singlet; d=doublet; t=triplet; q=quartet; m=multipier; dd=double doublet; ddt=double doublet of triplets, dtd=double triplet of doublets; b or br =broad; g=grammes; mg=milligrammes; $CDCl_3$=deuterochloroform; DMSO=$d_6$-dimethyl sulphoxide; Chemical shifts ($\delta$) are measured in parts per million from tetramethylene silane. $CDCl_3$ was used as solvent unless otherwise stated. $M^+$=molecular ion as determined by mass spectrometry; ir=infra red spectrometry; tlc=thin layer chromatography; (dec)=decomposed on melting.

EXAMPLE 1A

A general procedure for the preparation of 2-mercaptobenzthiazoles (from the corresponding 2-halonitrobenzene) is illustrated by the following preparation of 2-mercaptobenzthiazol-5-yl methyl sulphone (Ref. J.Am. Chem. Soc. (1944) 66, 835).

A solution of sodium sulphide nonahydrate (17.8 g) in water (16 cm$^3$) containing sulphur (4.8 g) was stirred at 75°–80° C. for 0.5 hour under an atmosphere of nitrogen to give a yellow solution. To the solution was added in portions 4-fluoro-3-nitrobenzene methyl sulphone (Fairfield Chemical Co ,5.6 g). The temperature of the mixture gradually rose to 100° C., and the mixture was cooled to 60° C. to complete the addition. Carbon disulphide (5 cm$^3$) was added to the reaction mixture at 60° C. through the condenser and the mixture was heated to reflux for 2 hours after which time the initially orange mixture gave a yellow precipitate. The reaction mixture was cooled, diluted with water (400 cm$^3$), the insoluble material was filtered from the solution, and the filtrate was acidified with acetic acid. The precipitated solid was filtered, washed with water and dried by suction. The solid was extracted with ethyl acetate (600 cm$^3$), the solution washed with water, dried (magnesium sulphate) and evaporated under reduced pressure to give the title product as a yellow solid. mp 242°–244° C.; ir: 3246,1328,1158. cm$^{-1}$ The following compounds were prepared using the method of Example 1A.

(i) 2-Mercapto-5-methoxybenzthiazole: yellow solid mp 198°–200° C. (from 4-methoxy-2-nitrochlorobenzene)

(ii) 2-Mercapto-5-fluorobenzthiazole: yellow solid mp 125° C. (dec) (from 1,4-difluoro-2-nitrobenzene)

(iii) 2-Mercapto-7-chlorobenzthiazole: fawn solid mp 250°–251° C. (dec) (from 1,2-dichloro-3 nitrobenzene)

(iv) 5-Bromo-2-mercaptobenzthiazole: yellow solid mp 186° C.; $M^+$=245 (from 1,4-dibromo-2-nitrobenzene)

(v) 2-Mercapto-5-trifluoromethoxybenzthiazole: colourless solid mp 144° C.; $M^+$=251 (from 2-nitro-4-trifluoromethoxyfluorobenzene)

(vi) 2-Mercapto-5-trifluoromethylthiobenzthiazole: colourless solid mp 138°–140° C.; $M^+$=267 (see Example 7(i) for preparation of starting material)

(vii) 2-Mercapto-5-trifluoromethylsulphinylbenzthiazole ($M^+$=283) and 2-Mercapto-5-trifluoromethylsulphonylbenzthiazole ($M^+$299) from 2-nitro-4-trifluoromethylsulphinylbromobenze and 2-nitro-4-trifluoromethylsulphonylbromobenzene; (see Example 7(iii) for preparation of starting materials)

(viii) 2-mercapto-5-methylbenzthiazole: yellow crystals mp 173°–175° C. (from 4-chloro-3-nitrotoluene)

(ix) 2-mercapto-5-(N,N-dimethylsulphonamido)benzthiazole: mp 220° C. (see Example 7(ii) for preparation of starting material).

EXAMPLE 1B

A general procedure for the preparation of 2-mercaptobenzthiazoles (from the corresponding 2-aminobenzthiazoles) is illustrated by the following preparation of 6-fluoro-2-mercaptobenzthiazole (Ref. J.Het. Chem. (1980) 17 1325).

A solution of 2-amino-6-fluorobenzthiazole (10.0 g) in water (100 cm$^3$) containing sodium hydroxide (50.0 g) was stirred and heated to reflux for 18 hours, cooled to the ambient temperature and filtered. Carbon disulphide (17.5 cm$^3$) was added to the filtrate and the mixture was heated to reflux for 4 hours, cooled to the ambient temperature, diluted with water and neutralised with acetic acid. The fawn solid which precipitated was filtered from solution, washed with water and dried by suction to give the title product, mp above 260° C., $M^+$=185.

The following compounds were prepared using the method of Example 1B.

(i) 2-Mercapto-4-methylbenzthiazole: mp above 260° C.; $M^+$=181; yellow solid (ii) 2-Mercapto-6-methylbenzthiazole: mp 248° C.; $M^+$=181; yellow solid

EXAMPLE 1C

A general procedure (the 'Herz process') for the preparation of 2-mercaptobenzthiazoles from the corresponding 2-mercaptoaniline (and a procedure for preparing the 2-mercaptoaniline from the corresponding aniline) is illustrated by the following preparation of 6-chloro-2-mercaptobenzthiazole.

To a stirred solution of 4-chloroaniline (2.55 g) in acetic acid (5 cm$^3$) was added sulphur monochloride (10 cm$^3$) causing formation of a thick red slurry. The reaction was heated at 60° C. for 4 hours giving a mixture of green solid and a green solution. The mixture was diluted with hexane and the green solid was filtered off. The solid was taken into water and 2M NaOH was added and the mixture heated for 4 hours at 100° C. and then filtered through celite to give a pale pink filtrate. Carbon disulphide (2 cm$^3$) was added to the filtrate and the reaction was heated at reflux for 15 hours. The mixture was cooled and acidlied to pH 1 causing formation of a thick yellow precipitate. Filtration and recrystallisation from ethanol/acetone/water gave 6-chloro-2-mercaptobenzthiazole as a white solid. $^1$H NMR (DMSO): d 7.97 (1H, d), 7.58 ( 1H, dd), 7.41 (1H, d). Mp 251°–253° C. (dec).

The following compounds were prepared using the method of Example IC from the corresponding starting materials.

(i) 2-mercapto-6-methoxybenzthiazole tan solid; $^1$H nmr (DMSO) d: 13.10 (1H, bs), 7.21 (1H, d), 6.95 (1H, bs), 6.88 (1H, dd), 3.89 (3H, s). Mp 199°–200° C.

(ii) 2-mercapto-5-trifluoromethylbenzthiazole. yellow solid; $^1$H nmr (CDCl$_3$, drop of DMSO) d: 13.50 (1H, bs), 7.40–7.60 (3H, m, overlapping aromatic signals). Mp 218°–219° C. (dec), M+=235.

EXAMPLE 1D

This Example illustrates miscellaneous preparative methods for 2-mercaptobenzthiazoles.

(i) 2-mercaptobenzthiazole-5-carboxylic acid.

To a stirred suspension of 4-chloro-3-nitrobenzoic acid (20 g) in DMF (1 cm$^3$) and dichloromethane (100 cm$^3$) was added oxalyl chloride (13 g) in dichloromethane (50 cm$^3$) over 1 hour. The reaction was stirred at 30° C. for 5 hours, after which reaction became homogeneous, and stirred at the ambient temperature for 18 hours. Evaporation under reduced pressure gave a white solid that was triturated with hexane and dried to give 4-chloro-3-nitrobenzoyl chloride as a white solid (21.82 g). $^1$H nmr (CDCl$_3$) d: 8.61 (1H, d), 8.26 (1H, dd), 7.78 (1H, d). Mpt 49°–51° C.

To a stirred solution of 4-chloro-3-nitrobenzoyl chloride (20.5 g) in ethyl acetate (80 cm$^3$) was added a solution of triethylamine (10.1 g) and i-propylalcohol (6 g) in ethylacetate (40 cm$^3$) over 15 mins causing a slight exotherm. The reaction was stirred at the ambient temperature for a further 3.5 hours and then poured into water. The layers were separated and the aqueous layer was extracted with ethyl acetate and the combined ethyl acetate layers were washed with 10% HCl, brine and dried with sodium sulphate. Filtration and evaporation gave iso-propyl 4-chloro-3-nitrobenzoate as a yellow solid (22.5 g). $^1$H nmr (CDCl$_3$) d: 8.49 (1H, d), 8.17 (1H, dd), 7.64 (1H, d), 5.29 (1H, septet), 1.40 (6H, d). Mpt 61°–62° C.

A mixture of iso-propyl 4-chloro-3-nitrobenzoate (15.84 g) and sodium sulphide nonahydrate (47 g) in water (110 cm$^3$) was heated at reflux for 17 hours giving a homogeneous red solution. Carbon disulphide (6 cm$^3$) was added and the reaction was heated under reflux for 4 hours. After cooling the mixture was acidified to pH1 with concentrated HCl causing formation of a tan precipitate. The solid was filtred off and recrystallised from ethanol/acetone/water to give the title product as a tan solid (8.85 g). $^1$H nmr d: 7.54 (1H, d), 7.40 (1H, d), 7.21 (1H, dd). Mpt >300° C.

(ii) 3 Step preparation of 2-mercapto-5,6-methylenedioxybenzthiazole.

Step 1: 2-Amino-5,6-methylenedioxybenzthiazole.

3,4-Methylenedioxyphenylthiourea (1.96 g; Lancaster Chemical Co) in chloroform (6 cm$^3$) was stirred at ambient temperature and a solution of bromine (0.37 cm$^3$) in chloroform (3 cm$^3$) was added in portions. The mixture was cooled using a water bath and after 1 hr. was stored for 64 hr., diluted with water (100 cm$^3$), basified with aqueous 2M sodium hydroxide and extracted with ethyl acetate (2×150 cm$^3$). The combined organic phases were washed with water and dried (magnesium sulphate). The solution was evaporated under reduced pressure to give the required product as a pale pink solid; mp 200° C.; $^1$H NMR (CDCl$_3$): δ7.06 (1H,s); 7.02(1H,s); 5.98(2H,s); 5.0(broad signal, 2H).

Step 2: 2-Chloro-5,6-methylenedioxybenzthiazole

The product from Step 1 (1.7 g) was partially dissolved in dry acetonitrile (50 cm$^3$) and added in portions to a stirred suspension of copper(II) chloride (1.41 g) and tert-butyl nitrite (1.56 cm$^3$) in dry acetonitrile (15 cm$^3$) at 60° C. The mixture was heated for 1 hr., cooled to ambient temperature, poured into water/diethyl ether and acidified with aqueous 2M hydrochloric acid. The aqueous fraction was separated and extracted with diethylether (3×100 cm$^3$) and the combined organic fractions washed with water (3×50 cm$^3$) and dried (magnesium sulphate). The solution was evaporated under reduced pressure to give a brown solid. The solid was fractionated by absorbing it onto silica and eluting with hexane/ethyl acetate (50:1 by volume) to give the required product as a colourless solid, M+=213; $^1$NMR (CDCl$_3$): δ7.36(1H,s): 7.14(1H,s); 6.08(2H,s); mp 131°–2° C.

Step 3: 2-Mercapto-5,6-methylenedioxybenzthiazole

The product from Step 2 (0.67 g) and thiourea (0.26 g) were mixed in ethanol (20 cm$^3$) and stirred and heated to reflux under an atmosphere of nitrogen for 18 hr. The pale yellow solid which precipitated was filtered from the solution at ambient temperature, washed with ethanol and sucked to dryness to give the required product. $^1$H NMR (DMSO): δ7.26(1H,s); 6.80(1H,s); 6.02(2H,s); mp 265° C. (dec); M+=211.

EXAMPLE 2A

A general procedure for the preparation of 2-mercaptobenzoxazoles (from the corresponding 2-aminophenol) is illustrated by the following preparation of 2-mercapto-5-methylbenzoxazole.

To a brown solution of 2-amino-5-methylphenol (5 g) in 2M NaOH (80 cm$^3$) stirring at the ambient temperature was added carbon disulphide and the reaction mixture was stirred for 5 days. The solution was acidified to pH 4 by the addition of concentrated hydrochloric acid, causing formation of a beige precipitate. The precipitate was filtered and dried by suction to give the title product as a free flowing beige powder (4.06 g). $^1$H NMR (DMSO): δ13.9 (1H,br s); 7.5(1H,d); 7.18(1H,d); 7.15(1H,s); 2.49(3H,s) ppm.

The following compounds were prepared using the method of Example 2A (i) 2-mercapto-4-methylbenzoxazole—beige powder. $^1$H NMR (DMSO): δ7.27(1H,d); 6.98–7.18(2H,m).

(ii) 4-hydroxy-2-mercaptobenzoxazole—beige powder. $^1$H NMR (DMSO): δ7.00(1H, t); 6.9(1H,d); 6.7(1H,d).

(iii) 4-amino-2-mercaptobenzoxazole—ginger solid. $^1$H NMR (DMSO): δ1H NMR 12.45(2H, br s); 10.00 (1H,br s); 7.0(1H,t); 6.6–6.75(2H,2xd).

(iv) 2-mercaptobenzoxazole-4-carboxylic acid—beige solid. $^1$H NMR (DMSO): δ7.65–7.85(2H,2xd); 7.30(1H, t).

(v) 5 chloro-2-mercapto benzoxazole—grey solid. $^1$H NMR (DMSO): δ7.60(1H,d); 7.30–7.40(2H,m).

(vi) 2-mercaptobenzoxazole-5-carboxylic acid—beige solid. $^1$H NMR (DMSO): δ7.95(1H,d); 7.78(1H,d); 7.65(1H,d).

(vii) 4,5-benzo-2-mercaptobenzoxazole. $^1$H NMR (DMSO): δ8.35(1H,d); 8.20(1H,d); 8.00(1H,d); 7.88(1H,d); 7.81(1H,t); 7.71(1H,t).

EXAMPLE 2B

This Example gives a general process for the preparation of 2-mercaptobenzoxazoles from the corresponding 2-aminophenol or a salt thereof, as illustrated by the procedure for preparing 2-mercapto-7-nitrobenzoxazole.

Carbon disulphide (0.6 cm$^3$) was added to a solution of potassium hydroxide (0.652 g) in methanol (16.5 cm$^3$) and water (3 cm$^3$). The resulting solution containing potassium methyl xanthate was added to 2-amino-6nitrophenol (1.4 g) and the mixture heated and stirred under reflux for 18 hours. The resulting solution was cooled, acidified to pH 3 with concentrated hydrochloric acid, and the dark orange solid which precipitated was recoved by filtration and dried by suction. This gave 2-mercapto-7-nitrobenzoxazole (1.25 g). M$^+$=196; $^1$H NMR (DMSO): $\delta$7.6(1H,t); 7.75(1H,d); 8.1(1H,d).

The following intermediates were prepared using the method of Example 2B.

(i) 2-mercapto-6-nitrobenzoxazole—yellow/orange solid. M$^+$=196; $^1$H NMR (DMSO): $\delta$7.55(1H,d); 8.35(1H,dd); 8.55(1H,d).

(ii) 2-mercapto-6-methylbenzoxazole—cream solid. $^1$H NMR (CDCl$_3$): $\delta$2.45(3H,s); 7.1(2H,s); 7.2(1H,s).

(iii) methyl 2-mercaptobenzoxazol-6-carboxylate—orange solid. $^1$H NMR (CDCl$_3$): $\delta$3.9(3H,s); 7.2(1H,d); 7.9–8.05(2H,m).

(iv) 5-(ethanesulphonyl)-2-mercaptobenzoxazole—grey/brown solid. M$^+$=243; $^1$H NMR (DMSO): $\delta$1.15(3H,t); 3.35–3.45(2H,q); 7.7(1H,s); 7.8–7.9(2H,m).

(v) 5-cyano-2-mercaptobenzoxazole. M$^+$=176; $^1$H NMR (CDCl$_3$): $\delta$6.9(1H,br s); 7.2–7.5(2H,m).

(vi) 5-amino-2-mercaptobenzoxazole—grey solid. M$^+$=166; $^1$H NMR (DMSO): $\delta$5.2–5.5(1H,br s); 6.5–6.6(2H,m); 7.25(1H,d).

(vii) 2-mercapto-7-methylbenzoxazole-brown solid. M$^+$=165; $^1$H NMR (DMSO): $\delta$2.45(3H,s); 7.1–7.35(3H,m).

(viii) 6-hydroxy-2-mercaptobenzoxazole—brown solid. $^1$H NMR (DMSO) 13.7–13.8(1H,bs); 9.75–10.0(1H,bs); 7.15–7.20(1H,d); 7.0–7.05(1H,d); 6.8–6.9(1H,dd).

EXAMPLE 2C

A general procedure for the preparation of 2-mercaptobenzoxazoles (from the corresponding 2-aminophenol) is illustrated by the following preparation of 2-mercapto-4-nitrobenzoxazole.

Sodium hydroxide (1.2 g) was added to water (3 cm$^3$) and allowed to dissolve before addition of dioxane (45 cm$^3$) and 2-amino-3-nitrophenol (4.5 g). The dark red solution was cooled to 0° C. and thiophosgene (4.5 g in dioxane (15 cm$^3$)) was added and the reaction stirred for 18 hours at the ambient temperature. Water was added to the mixture causing precipitation of an olive green solid which was filtered and dried under vacuum to give the title product (1.15 g). $^1$H nmr (CDCl$_3$): d 8.0 (1H, d), 7.88 (1H, d), 7.4 (1H, t).

The following compound was also made by the method described in Example 2C from 2-amino-4-nitrophenol.

(i) 2-mercapto-5-nitrobenzoxazole $^1$H nmr (CDCl$_3$): d 8.32 (1H, dd), 8.08 (1H, bs), 7.85 (1H, d).

EXAMPLE 3A

This example illustrates the preparation of 1,4-dibromo-1,1,2-trifluorobutane.

A solution of 4-bromo-1,1,2-trifluorobut-1-ene (2.5 g) in dry dichloromethane (25 cm$^3$) at 0° C. was treated with HBr gas for 45 minutes. The reaction mixture was then stirred at 0° C. for 1 hour. The reaction mixture was made alkaline with 5% NaHCO$_3$ solution and extracted twice with dichloromethane. The combined dichloromethane extracts were dried (MgSO$_4$), filtered and concentrated under reduced pressure to give a pale yellow liquid (2.84 g). The material was shown by gc analysis to be greater than 99% pure. $^1$H NMR (CDCl$_3$): $\delta$4.75–5.07(1H,m); 3.42–3.69(2H,m); 2.59–2.15(2H,m).

EXAMPLE 3B

This Example illustrates the two step process for the preparation of 4,4-difluorobut-3-enyl p-tolylsulphonate.

Step 1: 4-bromo-3,4,4-trifluorobutyl p-tolylsulphonate

To a stirred suspension of silver rosylate (1.03 g) in acetonitrile (10 cm$^3$) at the ambient temperature, protected from the light, was added dropwise 1,4-dibromo-1,1,2-trifluorobutane (1 g). The reaction was then heated under reflux for 24 hours after which gc analysis indicated complete consumption of starting material. The reaction mixture was cooled to the ambient temperature and the precipitate was filtered off and washed with ethyl acetate. The filtrate and ethyl acetate washings were combined and washed with water and the aqueous layer extracted with ethyl acetate. The combined ethyl acetate layers were washed with water and brine, dried (MgSO$_4$) and evaporated under reduced pressure to give a brown oil (1.21 g). GC analysis showed this material to be >99% pure. $^1$H NMR (CDCl$_3$): $\delta$7.80(2H,d); 7.38(2H,d); 4.74(1H,m); 4.19(2H,m); 2.46(3H,s); 2.20(2H,m)

Step 2: 4,4-difluorobut-3-enyl p-tolylsulphonate

To a stirred suspension of powdered zinc (1.41 g) and iodine (one grain) in methanol (3 cm$^3$) was added a solution of 4-bromo-3,4,4-difluorobutyl p-tolysulphonate (710 mg) in methanol (2 cm$^3$). The reaction mixture was refluxed for 2½ hours after which gc analysis indicated complete consumption of starting material. The organic phase was pipetted from the zinc suspension and the zinc was washed with 3 portions of ethyl acetate. The combined ethyl acetate portions were washed with 2M hydrochloric acid, dried (MgSO$_4$) and evaporated under reduced pressure to give a brown liquid (470 mg). GC analysis showed this material to be >99% pure. $^1$H NMR (CDCl$_3$): $\delta$7.79(2H,d); 7.38(2H,d); 4.15(1H,m); 4.01(2H,m); 2.46(3H,s); 2.35(2H,m).

EXAMPLE 3C

This Example illustrates the three step preparation of 4-bromo-4,4-difluorobutyl methanesulphonate.

Step 1: 4-Bromo-4,4-difluorobutanoic acid

To a stirred solution of acrylic acid (1.44 g) and acetonitrile (80 cm$^3$) was added sodium dithionite (4.18 g), sodium bicarbonate (2.01 g), water (20 cm$^3$) and finally dibromodifluoromethane (5 cm$^3$). The biphasic mixture was stirred at the ambient temperature with the inorganic salts gradually dissolving. Gc analysis after 4 hrs indicated complete consumption of acrylic acid. The aqueous phase was saturated with solid sodium chloride. The organic phase was separated, dried (MgSO$_4$), filtered and evaporated under reduced pressure to give a pale yellow oil with a small amount of a white solid. This mixture was taken up in ethyl acetate, filtered and evaporated under reduced pressure to give a pale yellow oil (2.54 g). $^1$H NMR (DMSO): δ2.65(2H,m); 2.45(2H, t).

Step 2: 4-Bromo-4,4-difluorobutanol

Under an atmosphere of nitrogen a solution of lithium almuninium hydride in diethylether (5 cm$^3$, 5 mM) was cooled to 0° C. Maintaining this temperature 4-bromo-4,4-difluorobutanoic acid (1 g, 4.9 mM) dissolved in dry diethylether (5 cm$^3$) was added dropwise with stirring. After an hour at 0° C. the reaction mixture was cautiously quenched by the addition of 2M hydrochloric acid. The organic phase was separated, washed with saturated sodium bicarbonate solution, dried over anhydrous magnesium sulphate, filtered and evaporated under reduced pressure to a colourless oil (570 mg). $^1$H NMR (CDCl$_3$): δ3.74(2H,t); 2.40–2.60 (2H,m); 1.82–1.96(2H,m).

Step 3: 4-Bromo-4,4-difluorobutyl methanesulphonate

A stirred solution of 4,bromo-4,4-difluorobutanol (570 mg, 3 mM) in dry diethylether (5 cm$^3$) was cooled to 0° C. Maintaining this temperature, triethylamine (17 cm$^3$, 12.2 mM) was added. After ten minutes methanesulphonyl chloride (0.3 cm$^3$, 3.9 mM) was added and the mixture stirred for a further hour at 0° C. The reaction mixture was poured into 2M hydrochloric acid (2 cm$^3$) and diethylether (20 cm$^3$). The organic phase was separated, washed with saturated brine, then passed through a plug of silica gel eluting with further diethylether. The diethylether fractions were evaporated under reduced pressure to a light yellow oil (705 mg). $^1$H NMR (CDCl$_3$): δ4.32(2H,t); 3.04(3H,s); 2.46–2.64(2H,m); 2.04–2.18(2H,m).

EXAMPLE 4A

A general procedure for the two-step preparation of 2-(4,4-difluorobut-3-enylthio) substituted benzoxazoles and benzthiazoles by reaction of the corresponding 2-mercapto-substituted heterocycle with 1,4-dibromo-3,4,4-trifluorobutane (see Example 3A), followed by dehalogenation of the product obtained thereby, is illustrated by the following preparation of 6-hydroxy-2-(4,4-difluorobut-3-enyl)benzoxazole (Compound No. 54).

Step 1:
6-Hydroxy-2-(4-bromo-3,4,4-trifluorobutylthio)benzoxazole

A mixture of 6-hydroxy-2-mercaptobenzoxazole (Example 2B(viii), 6.0 g, 22.2 mmol), acetone (60 cm$^3$), potassium carbonate (3.87 g, 28.0 mmol) and 6-hydroxy-2-mercaptobenzoxazole (5.08 g, 30.4 mmol) was stirred at room temperature for 48 hours. The reaction mixture was quenched by the addition of 1.4M hydrochloric acid and extracted with diethyl ether. The organic phase was washed with saturated brine, dried over anhydrous magnesium sulphate, filtered and concentrated under reduced pressure to give a red liquid. Chromatograpy on silica gel using 8:2 hexane:ethyl acetate as eluent afforded the product as a white solid (6.51 g). $^1$H NMR (CDCl$_3$): δ7.45(1H,d); 7.0(1H,d); 6.8(1H,dd); 5.65(1H,s); 4.7–5.0(1H 3.25–3.6(2H,m); 2.3–2.6(2H,m). M$^+$=355. m.p. 64.6°–67.6° C.

Step 2:
6-Hydroxy-2-(4,4-difluorobut-3-enylthio)benzoxazole
(Compound No 54)

A mixture of the product of step 1 (5.27 g, 14.7 mmol), Methanol (50 cm$^3$), zinc powder (9.66 g, 147 mmol), zinc iodide (catalytic), and iodine (catalytic) was refluxed for 18 hours. The reaction mixture was filtered and the filtrate partitioned between diethyl ether and 1.4M hydrochloric acid. The organic phase was washed with water, dried over anhydrous magnesium sulphate, filtered and concentrated under reduced pressure to give a brown oil. Chromatography on silica gel using 8:2 hexane:ethylacetate as eluent afforded the product as a white solid (2.13g). $^1$H NMR (CDCl$_3$): δ7.45($^1$H,d); 6.95($^1$H,d); 6.8($^1$H,dd); 6.1($^1$H,s); 4.2–4.4(1H,m); 3.3(2H,t); 2.5(2H,m). M$^+$=257. m.p. 73.6°–75.4° C.

The following compounds according to the invention and the corresponding intermediate compounds were prepared according to the two-step procedure of Example 4A. Where the 2-mercapto benzoxazoles and benzthiazoles are not readily available commercially, they may be prepared by the procedures in Examples 1A-1D and 2A-2C, or by procedures analogous to these.

(i) N,N-diethyl 2-(4,4-Difluorobut-3-enylthio)benzoxazole-5sulphonamide (compound No 75). mp 71°–72° C.; M$^+$=376; $^1$H NMR (CDCl$_3$): 6 1.15(t 1H); 2.6(m 2H); 3.2–3.3(q 4H); 3.35(t 2H); 4.25–4.4(m 1H); 7.55(d 1H) 7.75(dd 1H); 8.05(d 1H).

from N,N-diethyl 2-(4-bromo-3,4,4-trifluorobutylthio)benzoxazole-5-sulphonamide. mp 86.6°–87.6° C.; M$^+$=476 and 474 (Bromine isotopes); $^1$H NMR (CDCl$_3$ ): δ1.15(t 6H); 2.4–2.65(m 2H); 3.25(q 4H); 3.35–3.7(m 2H); 4.75–5.0(m 1H); 7.55(d 1H); 7.8(dd 1H); 8.1(d 1H)

(ii) 7-Fluoro-2-(4,4-difluorobut-3-enylthio)benzoxazole (Compound No 78). M$^+$=259; $^1$H NMR (CDCl$_3$): δ2.58(m 2H); 3.33(t 2H); 4.2–4.4(m 1H); 7.00(t 1H); 7.22(m 1H); 7.40(d 1H).

from 7-Fluoro-2-(4-bromo-3,4,4-trifluorobutylthio)-benzoxazole.

EXAMPLE 4B

A general procedure for the preparation of 2-(4,4-difluorobut-3-enylthio)-substituted benzoxazoles and benzthiazoles by reaction of the corresponding 2-mercapto heterocycle with 4,4-difluorobut-3-enyl p-tolylsulphonate (see Example 3B) is illustrated by the following preparation of 2-(4,4-difluorobut-3-enylthio)-4-nitrobenzoxazole (Compound No. 81)

To a brown stirred suspension of 2-mercapto-4-nitrobenzoxazole (Example 2C, 550 mg) and potassium carbonate (375 mg) in acetone (15 cm$^3$) was added 4,4-difluorobut-3-enyl p-tolylsulphonate (700 mg) and the mixture was heated under reflux for 21 hours. The reaction was quenched by the addition of water, and extracted three times with ethyl acetate. The combined organic layers were washed with water, brine and dried (MgSO$_4$). Filtration and evaporation under reduced pressure gave a brown solid (806 mg). Recrystallisation from ethyl acetate and hexane gave 2-[4,4-difluorobut-3-enylthio]-4-nitrobenzoxazole as a brown crystalline solid (396 mg). GC analysis indicated that the material was >99% pure. $^1$H NMR (CDCl$_3$) δ: 8.14(1H,d);

7.75(1H,d); 7.39(1H,t); 4.34(1H,m); 3.48(2H,t) 2.61(2H,m).

The following compounds were prepared from the corresponding 2-mercapto benzoxazole or 2-mercaptobenzthiazole using the method of Example 4B. Where the 2-mercapto benzoxazoles and benzthiazoles are not readily available commercially, they may be prepared by the procedures in Examples 1A–1D and 2A–2C, or by procedures analogous to these.

(i) 2-(4,4-difluorobut-3-enylthio)-4-methylbenzoxazole (Compound No. 79). $^1$H NMR (CDCl$_3$): $\delta$7.28(1H,m); 7.11(2H,m); 4.32(1H,m); 3.32(2H,t); 2.55(2H,m); (oil).

(ii) 4,5-benzo-2-(4,4-difluorobut-3-enylthio)benzoxazole (Compound No. 142). $^1$H NMR (CDCl$_3$): $\delta$8.45(1H,d); 7.96(1H,d); 7.74(1H,d); 7.64(2H,m); 7.52(1H,t); 4.38(1H, m); 3.41(2H,t); 2.62(2H,q); (oil).

(iii) 2-(4,4-difluorobut-3-enylthio)-4-hydroxybenzoxazole (Compound No. 82). $^1$H NMR (CDCl$_3$): $\delta$7.15(1H,t); 7.02(1H,d); 6.83(1H,d); 6.66(1H,s); 4.29(1H,m); 3.31(2H,t); 2.55(2H,q); (oil).

(iv) 4-amino-2-(4,4-difluorobut-3-enylthio)benzoxazole (Compound No. 80). $^1$H NMR (CDCl$_3$): $\delta$7.05(1H,t); 6.85(1H,d); 6.58 (1H,d); 4.31(1H,m); 3.31(2H,t); 2.43(2H,q); (oil).

(v) 2-(4,4-difluorobut-3-enylthio)-5-methylbenzoxazole (Compound No. 41). $^1$H NMR (CDCl$_3$): $\delta$7.38(1H,s); 7.30(1H,d); 7.03(1H,d); 4.30(1H,m); 3.32(2H,t); 2.69(2H,q); 2.45(3H,s); (oil).

(vi) 5-chloro-2-(4,4-difluorobut-3-enylthio)benzoxazole (Compound No. 89). $^1$H NMR (CDCl$_3$): $\delta$7.58(1H,dd); 7.36(1H,d); 7.22(1H,dd); 4.31(1H,m); 3.33(2H, t); 2.56(q); (oil).

(vii) 2-(4,4-difluorobut-3-enylthio)-5-nitrobenzoxazole (Compound No 143). $^1$H NMR (CDCl$_3$): $\delta$8.48(1H,d); 8.23(1H,dd); 7.54(1H,d); 4.31(1H,m); 3.38(2H,t); 2.59(2H,q); (yellow solid).

(viii) 2-(4,4-Difluorobut-3-enylthio)benzoxazole (Compound No. 2). M$^+$=241; $^1$H NMR (CDCl$_3$): $\delta$2.5–2.6 (m 2H), 3.3–3.4 (t 2H), 4.2–4.4 (m 1H), 7.2–7.35 (m 2H), 7.45 (dd 1H), 7.6 (dd 1H).

(ix) Methyl 2-(4,4-difluorobut-3-enylthio)benzoxazole-6-carboxylate (Compound No. 10). M$^+$=299; $^1$H NMR (CDCl$_3$): $\delta$2.5–2.6 (m 2H), 3.35 (t 2H), 3.95 (s 3H), 4.2–4.4 (m 1H), 7.65 (d 1H), 8.05 (dd 1H), 8.15 (d 1H); (oil).

(x) 2-(4,4-Difluorobut-3-enylthio)-6-methylbenzoxazole (Compound No. 48). M$^+$=255; $^1$H NMR (CDCl$_3$): $\delta$2.45 (s 3H), 2.5–2.6 (m 2H), 3.25–3.35 (t 2H), 4.2–4.5 (m 1H), 7.1 (br d 1H), 7.25 (d 1H), 7.5 (d 1H); (oil).

(xi) 2-(4,4-Difluorobut-3-enylthio)-6-nitrobenzoxazole (Compound No. 5). M$^+$=286; $^1$H NMR (CDCl$_3$): $\delta$2.55–2.65 (m 2H), 3.35–3.45 (t 2H), 4.25–4.40 (m 1H), 7.65 (d 1H), 8.25 (dd 1H), 8.35 (d 1H); (oil).

(xii) 5-Cyano-2-(4,4-difluorobut-3-enylthio)benzoxazole (Compound No. 90). mp 72°–74° C.; M$^+$=266; $^1$H NMR (CDCl$_3$): $\delta$2.55–2.65 (m 2M), 3.3–3.4 (t 2H), 4.2–4.4 (m 1H), 7.5–7.6 (m 2H), 7.9 (br s 1H).

(xiii) 2-(4,4-Difluorobut-3-enylthio)-5-phenylbenzoxazole (Compound No 26) mp 41°–42.4° C.; M$^+$=317; $^1$NMR (CDCl$_3$): $\delta$2.5–2.65 (m 2H), 3.3–3.4 (t 2H), 4.25–4.45 (m 1H), 7.3–7.5 (m 5H), 7.6 (d 2H), 7.8 (s 1H).

(xiv) 2-(4,4-Difluorobut-3-enylthio)benzoxazol-5-yl ethyl sulphone. (Compound No 73). M$^+$=333; $^1$H NMR (CDCl$_3$): $\delta$1.25 (t 3H), 2.55–2.65 (m 2H), 3.1–3.2 (q 2H), 3.35–3.45 (t 2H), 4.25–4.45 (m 1H), 7.6 (d 1H), 7.85 (dd 1H), 8.15 (d 1H); (oil).

(xv) 2-(4,4-difluorobut-3-enylthio)benzthiazol-5-yl methyl sulphone (compound No 74). ir 1760 cm$^{-1}$; M$^+$=335; $^1$H NMR (CDCl$_3$): $\delta$2.58(m,2H); 3.12(s,3H); 3.45(t,2H); 4.3(m, 1H); 7.86(dd,1H); 7.95(d,1H); 8.42(d,2H).

(xvi) 2-(4,4-Difluorobut-3-enylthio)-6-fluorobenzthiazole (Compound No 15). ir 1750 cm$^{-1}$; M$^+$=275; $^1$H NMR (CDCl$_3$): $\delta$2.50(m 2H); 3.35(t 2H); 4.25(m 1H); 7.10(m 1H); 7.40(dd 1H); 7.75(dd 1H); (oil).

(xvii) 5-Bromo-2-(4,4-difluorobut-3-enylthio)benzthiazole (Compound No 61). ir 1750 cm$^{-1}$; M$^+$337; $^1$H NMR (CDCl$_3$): $\delta$2.55(m 2H); 3.40(t 2H); 4.30(m 1H); 7.42(dd 1H); 7.60(d 1H); 8.02(dd 1H); (oil).

(xviii) 2-(4,4-Difluorobut-3-enylthio)-4-methylbenzthiazole (Compound No 16); M$^+$=271; $^1$H NMR (CDCl$_3$): $\delta$2.55(m 2H); 2.68(s 3H); 3.40(t 2H); 4.32(m 1H); 7.2(m 2H); 7.60(dd 1H); (oil).

(xix) 2-(4,4-Difluorobut-3-enylthio)-6-methylbenzthiazole (Compound No 7). M$^+$=271; $^1$H NMR (CDCl$_3$): $\delta$2.48(s 3H); 2.55(m 2H); 3.35(t 2H); 4.3(double triplet of doublets 1H); 7.20(dd 1H); 7.55(s 1H); 7.75(d 1H); (oil).

(xx) 2-(4,4-Difluorobut-3-enylthio)-5-methoxybenzthiazole (Compound No 71). ir(film) 1752 cm$^{-1}$; M$^+$=287; $^1$H NMR (CDCl$_3$): $\delta$ 2.54(m 2H); 3.38(t 2H); 3.88(s 3H); 4.32(double triplet of doublets 1H); 6.95(dd 1H); 7.40(d 1H); 7.60(d 1H); (oil).

(xxi) 2-(4,4-Difluorobut-3-enylthio)-5-fluorobenzthiazole (Compound No 69). ir (film) 1750 cm$^{-1}$; M$^+$=275; $^1$H NMR (CDCl$_3$): $\delta$2.55(m 2H); 3.40(t 2H); 4.3(double triplet of doublets 1H); 7.08(triplet of doublets 1H); 7.56(dd 1H); 7.68(dd 1H); (oil).

(xxii) 2-(4,4-Difluorobut-3-enylthio)-7-chlorobenzthiazole (Compound No 77). ir (film) 1750 cm$^{-1}$; M$^+$=291; $^1$H NMR (CDCl$_3$): $\delta$2.55(m 2H); 3.40(t 2H); 4.3(double triplet of doublets 1H); 7.28(d 1H); 7.36(t 1H); 7.77(d 1H).

(xxiii) 2-(4,4-Difluorobut-3-enylthio)-5-N,N-dimethylsulphonamidobenzthiazole (Compound No 76). mp 60° C.; M$^+$=364; $^1$H NMR (CDCl$_3$): $\delta$ 2.65(m 2H); 2.8(bs 6H); 3.50(t 2H); 4.4(double triplet of doublets 1H); 7.75(dd 1H); 8.00(d 1H); 8.30(d 1H).

(xxiv) 2-(4,4-Difluorobut-3-enylthio)-5-trifluoromethylthiobenzthiazole (Compound No 137); M$^+$=357; $^1$NMR (CDCl$_3$): $\delta$2.55 (m 2H); 3.4(t 2H); 4.3(double triplet of doublets 1H); 7.75(dd 1H); 7.80(d 1H); 8.15(d 1H); (oil).

(xxv) 2-(4,4-difluorobut-3-enylthio)-6-ethoxybenzthiazole (Compound No. 56). $^1$H NMR (CDCl$_3$): $\delta$7.74(1H,d); 7.24(1H,d); 7.00(1H,dd); 4.30(1H,dtd); 4.08 (2H,q); 3.36(2H, t); 2.53(2H, bq); (oil).

(xxvi) 5-chloro-2-(4,4-difluorobut-3-enylthio)benzthiazole (Compound No. 63). $^1$H NMR (CDCl$_3$): $\delta$7.87(1H,d); 7.66(1H,d); 7.28(1H,dd); 4.32(1H,dtd); 3.40(2H,t); 2.55(bq); (oil).

(xxvii) 2-(4,4-difluorobut-3-enylthio)-5-methylbenzthiazole (Compound No. 22). $^1$H NMR (CDCl$_3$): $\delta$7.68(1H,bs); 7.62(1H,d); 7.14(1H, bd); 4.32(1H,dtd); 3.38(2H,t); 2.54(2H, bq); 2.48(3H,s); (oil).

(xxviii) 2-(4,4-difluorobut-3-enylthio)-6-nitrobenzthiazole (Compound No. 52). $^1$H NMR (CDCl$_3$): $\delta$8.69(1H,d); 8.33(1H,dd); 7.92(1H,d); 4.33(1H, dtd); 3.47(2H, t); 2.59(2H, bq).

(xxix) 2-(4,4-difluorobut-3-enylthio)-5-trifluoromethylbenzthiazole (Compound No. 62). $^1$H NMR (CDCl$_3$): $\delta$8.12(1H bs); 7.86(1H,d); 7.55(1H,dd); 4.33(1H, dtd); 3.43(2H,t); 2.57(2H, bq); (oil).

(xxx) 2-(4,4-difluorobut-3-enylthio)-6-methoxybenzthiazole (Compound No. 58). $^1$H NMR (CDCl$_3$): δ7.75(1H,d); 7.23(1H,d); 7.02(1H,dd); 4.32(1H,dtd); 3.88(3H,s); 3.38(2H,t); 2.52(2H bq); (oil)

(xxxi) 6-chloro-2-(4,4-difluorobut-3-enyl-thio)benzthiazole (Compound No. 46). $^1$H NMR (CDCl$_3$): δ7.78(1H,d); 7.75(1H,d); 7.38(1H,dd); 4.32(1H,dtd); 3.41(2H,t); 2.56(2H, bq); (oil).

(xxxii) 6-fluoro-2-(4,4-difluorobut-3-en-ylthio)benzoxazole (Compound No. 47). $^1$H NMR (CDCl$_3$): δ7.53(1H,m); 7.18(1H,m); 7.05(1H,m); 4.23–4.44(1H,m); 3.33(2H,t); 2.58(2H,m); M+=259.

(xxxiii) 2-(4,4-Difluorobut-3-enylthio)-5,6-methylenedioxybenzthiazole (Compound No 128), colourless solid; mp 74°–5° C.; M+301; $^1$H NMR (CDCl$_3$): δ7.30(1H,s); 7.12(1H,s); 6.04(2H,s);4.3(1H,dtd); 3.44(2H,t); 2.52(2H,m).

(xxxiv) 2-(4,4-difluorobut-3-enylthio)-5-trifluoromethanesulphonylbenzthiazole (Compound No. 133); $^1$H NMR (CDCl$_3$): δ8.50(1H,d); 8.02(1H,d); 7.90(1H,dd); 4.3(1H,dtd); 3.45(2H,t); 2.58(2H,m);M+=389.

(xxxv) 2-(4,4-difluorobut-3-enylthio)-5-trifluoromethanesulphinylbenzthiazole (Compound No. 138); $^1$H NMR (CDCl$_3$): δ8.26(1H,s); 8.00(1H,d); 7.72(1H,d); 4.3(1H,dtd); 3.45(2H,t); 2.58(2H,m).

(xxxvi) 2-(4,4-difluorobut-3-enylthio)-5-trifluoromethoxybenzthiazole (Compound No. 96); $^1$H NMR (CDCl$_3$): δ7.75(2H,m); 7.20(1H,dd); 4.3(1H,dtd); 3.40(2H,t); 2.55(2H,m); M+341.

(xxxvii) 2-(4,4-difluorobut-3-enylthio)-7-methylbenzoxazole (Compound No. 17). M+=255; $^1$H NMR (CDCl$_3$): δ2.4–2.65(5H,m); 3.3–3.4(2H,t); 4.15–4.4(1H,m); 7.0–7.1(1H,d); 7.15–7.25(1H,t); 7.45(1H,d); (oil).

(xxxviii) 5-amino-2-(4,4-difluorobut-3-enylthio)-benzoxazole (Compound No. 103). M+=256

(xxxix) 2-(4,4-difluorobut-3-enylthio)-7-nitrobenzoxazole (Compound No. 114). M+=286; $^1$H NMR (CDCl$_3$): δ2.55–2.65(2H,m); 3.35–3.45(2H,t); 4.25–4.45(1H,m); 7.4(1H,t); 7.9(1H,d); 8.1(1H,d)

EXAMPLE 4C

The preparation of compounds according to the invention by reaction of a 2-mercapto substituted heterocycle with 4-bromo-4,4-difluorobutyl methanesulphonate (see Example 3C), followed by dehydrobromination of the resultant 2-(4-bromo-3,4-difluorobutylthio)-substituted intermediate, is illustrated by the following two-step preparation of 6-methoxy-2-(4,4-difluorobut-3-enylthio)benzoxazole (Compound No 57).

Step 1: 6-methoxy-2-(4-bromo-4,4-difluorobutylthio)-benzoxazole. A mixture of 6-methoxy-2-mercaptobenzoxazole (1.77 g, 9.8 mmoles), 4-bromo-4,4-difluorobutyl methanesulphonate (2.4 g, 9 mmoles), potassium carbonate (5 g, 36.2 mmoles) and acetone (60 cm$^3$) was stirred at the ambient temperature for 18 hours. The precipitate which formed was removed by filtration and the filtrate evaporated under reduced pressure to give a brown oil which was purified by chromatography on silica gel, eluted with a 1:4 mixture of ethyl acetate and hexane, to give the title intermediate product as a light yellow oil. $^1$H NMR (CDCl$_3$): δ7.48(d,1H); 7.00(d,1H); 6.90(dd,1H); 3.85(s,3H); 3.38(t,2H); 2.50–2.68(m,2H).

Step 2: 6-methoxy-2-(4,4-difluorobut-3-enylthio)benzoxazole (Compound No 57). To a stirred solution of the product from Step 1 (1 g, 2.84 mmoles) in dry toluene at 60° C. was added 1,8-diazabicyclo[5.4.0]undec-7-ene (DBU, 0.45 cm$^3$, 3mmoles) After 4 hours further DBU (0.45 cm$^3$, 3 mmoles) was added and heating continued for a further 3 hours. The reaction mixture was then allowed to cool and stand for 17 hours. The mixture was washed with 2M hydrochloric acid (20 cm$^3$) and the organic phase was separated. The aqueous phase was extracted with ethyl acetate (25 cm$^3$). The combined organic phases were washed with water (20 cm$^3$) and brine (20 cm$^3$) and dried over anhydrous magnesium sulphate, filtered and evaporated under reduced pressure to give the title product as a brown oil which was purified to a light yellow oil by column chromatography on silica gel, eluting with a 1:4 mixture of ethyl acetate and hexane. M+=271. $^1$H NMR (CDCl$_3$): δ2.48–2.6(m 2H); 3.32(t 2H); 3.84(s 3H); 4.22–4.38(m 1H); 6.88(dd 1H); 6.98(d 1H); 7.46(d 1H).

Compound No 57 may also be prepared by reaction of 6-methoxy-2-mercaptobenzoxazole and 4,4-difluorobut-3-enyl p-tolyl-sulphonate according to the method of Example 4B.

EXAMPLE 4D

The preparation of compounds according to the invention by Wittig condensation of a 2-(3-oxopropylthio)-substituted benzoxazole or benzthiazole with dibromodifluoromethane in the presence of triphenylphosphine is illustrated by the following 3-step preparation of 2-(4,4-difluorobut-3-enylthio)benzthiazole (Compound No 1).

Step 1: Preparation of 2-(2-(1,3-Dioxolan-2-yl)-benzthiazole

Potassium carbonate (3.8 g) was added to a stirred solution of 2-mercaptobenzthiazole (4.6 g) in acetone (50 cm$^3$) at room temperature. 2-(2-Bromoethyl)-1,3-dioxolane (5 g) was added to the mixture and the reaction then heated under reflux for 3 hours.

The reaction mixture was poured into water and extracted with diethyl ether. The organic phase was dried with magnesium sulphate and evaporated under reduced pressure to leave a brown oil. The crude product was subjected to column chromatography using silica gel and ethyl acetate (15% by volume) in hexane as eluent to give 2-(2-(1,3-dioxolan-2-yl)ethylthio)benzthiazole as a clear yellow oil. $^1$H NMR (CDCl$_3$): δ7.78(2H,d); 7.75(2H,d); 7.41(1H,t); 7.29(1H,t); 5.08(1H,t); 4.00(2H,m 3.90(2H,m); 3.47(2H,t); 2.24(2H,m); M+=267, 100.

Step 2: Preparation of 2-(3-Oxopropylthio)benzthiazole

Aqueous 10% hydrochloric acid (50 cm$^3$) was added to a solution of 2-(2-(1,3-dioxolan-2-yl)-ethyithio)benzthiazole (5.3 g) in tetrahydrofuran (50 cm$^3$). After stirring at the ambient temperature for 6 hours the reaction mixture was left to stand for 48 hours during which time a white precipitate formed. The solid was collected by filtration, and a portion (2 g) dissolved in 2M sodium hydroxide solution and extracted with diethyl ether. The organic phase was dried with magnesium sulphate and evaporated under reduced pressure to give the crude 2-(3-oxopropylthio)-benzthiazole as a gummy yellow solid. This material was used without further purification in step 3. $^1$H NMR (CDCl$_3$): δ9.85 (1H,s); 7.86 (2H,d); 7.78 (2H,d); 3.62 (2H,t); 3.12 (2H,t). Additional signals were observed at δ11.73 and δ7.50–7.00 but not assigned.

Step 3: Preparation of 2-(4,4-difluorobut-3-enylthio)benzthiazole (Compound No 1)

A dry reaction flask was purged with nitrogen and charged with a solution of crude 2-(3-oxopropylthio)-benzthiazole (0.5 g) and dibromodifluoromethane (0.941 g) in dry dimethylacetamide (15 cm$^3$). After cooling to 0° C., triphenylphosphine (1.1 g) was added to the stirred solution, and the mixture stirred at 0° C. for 30 minutes before being allowed to warm to room temperature. Zinc dust (0.291 g) was added in portions and the reaction warmed to 90° C. for 2 hours, then allowed to cool to, and stand at, room temperature for 4 days.

The reaction mixture was filtered using High-Flo and the residue and filter aid rinsed with ethyl acetate. The filtrate and washings were combined and washed with water. Drying and evaporation of the organic phase gave an oily solid residue.

The crude reaction mixture was subjected to column chromatography using silica gel and tert-butylmethylether (10% by volume) in hexane as eluent. Fractions containing the desired product were combined and evaporated under reduced pressure and the residue chromatographed using silica gel and ethyl acetate (2% by volume) in hexane as eluent to give the title product as a clear colourless liquid. $^1$H NMR (CDCl$_3$): δ7.88(1H,d); 7.78(1H,d); 7.44(1H,t); 7.31(1H,t); 4.34(1H,m); 3.40(2H, t); 2.56(2H, q). M$^+$=257, 167.

EXAMPLE 4E

A procedure suitable for the preparation of compounds according to the invention carrying a —CO$_2$H substituent on the benzoxazole or benzthiazole ring is illustrated by the following procedure for the preparation of 2-(4,4-difluorobut-3-enylthio)benzoxazole-5-carboxylic acid (Compound No 94).

To a stirred solution of 2-mercaptobenzoxazole-5-carboxylic acid (525 mg) and 4,4-difluorobut-3-enyl p-tolylsulphonate (703 mg) in tetrahydrofuran (15 cm$^3$) at the ambient temperature was added triethylamine (539 mg). The mixture was heated at the reflux temperature for 2.5 hours, stood at the ambient temperature for 18 hours and then heated at the reflux temperature for a further 5 hours. The mixture was poured into ethyl acetate and water and the phases separated. The aqueous phase was extracted twice with ethyl acetate and the combined organic layers were washed with water and dried over anhydrous magnesium sulphate. After filtration, the solvent was evaporated under reduced pressure to give a brown oil containing some solid material. Purification by chromatography on silica gel eluted with a 1:1 mixture of ethyl acetate and hexane gave the title product as a white solid. $^1$H NMR (DMSO): δ8.61(1H,bs); 8.07(1H,dd); 7.85(1H,d); 4.32(1H,m); 3.43(2H,t); 2.58(2H,bq).

The following compounds were prepared from the corresponding starting 2-mercapto-substituted heterocyclic carboxylic acid by the procedure of Example 4E.

(i) 2-(4,4-difluorobut-3-enylthio)benzoxazole-4-carboxylic acid (Compound No 97). $^1$H NMR (DMSO): δ8.10(1H,d); 7.69(1H,d); 7.42(1H,t); 4.32(1H,m); 3.40(2H,t); 2.60(2H,bq).

(ii) 2-(4,4-difluorobut-3-enylthio)benzthiazole-5-carboxylic acid (Compound No 68). $^1$H NMR (DMSO): δ8.61(1H,bs); 8.07(1H,dd); 7.85(1H,d); 4.32(1H,m); 3.43(2H,t); 2.58(2H,bq).

EXAMPLE 4F

A procedure suitable for the preparation of amino substituted compounds according to the invention is illustrated by the following 3-step procedure for the preparation of 6-amino-2-(4,4-difluorobut-3-enylthio)-benzoxazole (Compound No 6).

Step 1: Preparation of 2-(3-bromo-3,4,4-trifluorobutylthio)-6-nitrobenzoxazole. 2-Mercapto-6-nitrobenzoxazole (J. Org. Chem. 1–9, 758–66 (1954)) (5.44 g) was added to a solution of 1,4-dibromo-1,1,2trifluorobutane (6 g) in acetone (60 cm$^3$) containing potassium carbonate (4.6 g) and the mixture was stirred at ambient temperature for 48 hours and then at the reflux temperature for 6 hours. Inorganic solids were removed from the cooled reaction mass by filtration through a plug of High-Flo filter aid, which was washed with more acetone. The combined flitrates were concentrated under reduced pressure to give 9.63 g of a dark oil. This was triturated with dichloromethane and the insoluble portion discarded. The dichloromethane-soluble material (7.44 g) was chromatographed on silica gel, eluting with 10% ethyl acetate in hexane. This gave 5.43 g of a yellow oil which solidified on standing to give a solid of mp 53.8°–55.2° C. M$^+$=386 and 384 (Bromine isotopes); $^1$H NMR (CDCl$_3$): δ2.4–2.8(m 2H); 3.35–3.75(m 2H); 4.75–5.05(m 1H); 7.7(d 1H) 8.3(dd 1H); 8.4(d 1H).

Step 2: Preparation of 6-amino-2-(3-bromo-3,4,4-trifluorobutylthio)benzoxazole The product from Step 1 (3.65 g) was suspended in isopropanol (60 cm$^3$) and water (30 cm$^3$). Concentrated hydrochloric acid (3 drops) was added and the mixture was stirred with an air-driven stirrer until most of the starting material had dissolved before iron powder (7.3 g) was added and the whole mixture was warmed to 80° C. with continued stirring for 9.5 hours, until analysis by gc showed all of the starting material had reacted. The reaction mixture was cooled and filtered through a plug of High-Flo filter aid to remove inorganic material. Ethyl acetate and water were added and the product extracted into the ethyl acetate. This layer was separated and washed with more water, then saturated brine. The organic layer was dried over anhydrous magnesium sulphate and concentrated under reduced pressure to give a brown oil (3.18 g) which was subjected to chromatography on silica gel, eluting with 20% ethyl acetate in hexane. This provided 2.74 g of an orange oil: M$^+$=354; $^1$H NMR (CDCl$_3$): δ2.35–2.65(m 2H); 3.25–3.65(m 2H); 3.85(bs 2H); 4.75–5.05(m 1H); 6.6–6.65(dd 1H); 6.8(d 1H); 7.4(d 1H).

Step 3: Preparation of 6-amino-2-(4,4-difluorobut-3-enylthio)benzoxazole (Compound No 6). The product from Step 2 (2.5 g) was dissolved in tetrahydrofuran and zinc powder (4.5 g), zinc iodide (catalytic) and iodine (catalytic) were added. The mixture was refluxed for 12 hours at which time analysis by gc showed little consumption of starting material. Additional zinc (0.5 g) and catalysts were added and heating continued for 5 hours. At this stage, gc showed approximately conversion to product. Heating was continued for a further 16 hours, when gc showed that all the starting material had been consumed. The reaction mixture was cooled and filtered through a plug of High-Flo filter aid to remove inorganic material. The solids were washed with diethyl ether and the combined flitrates were washed with aqueous 1.4M hydrochloric acid and saturated brine. The organic layer was dried over anhydrous magnesium sulphate and concentrated by evaporation under reduced pressure to give 1.25 g of an orange oil. This material was subjected to chromatography on silica gel, eluting with 20% ethyl acetate in hexane and gave a pale orange oil (977 mg) which solidified on standing. mp 47.6°–49.8° C.; M+ =256; $^1$H NMR (CDCl$_3$): δ2.45–2.55(m 2H); 3.2–3.3(t 2H); 3.7–3.85(bs 2H); 4.2–4.4(m 1H); 6.65(dd 1H); 6.75(d 1H); 7.35(d 1H).

EXAMPLE 5

The following procedures illustrate procedures suitable for the preparation of compounds according to the invention in which the sulphur atom of the 2-substituent on the benzoxazole or benzthiazole ring of the corresponding unoxidised compound (prepared according to the procedures of Examples 4A-4F and 6) is oxidised to sulphoxide (sulphinyl) or sulphone (sulphonyl). In general, the use of one equivalent of oxidising agent leads predominantly to the formation of the corresponding sulphoxide product and two equivalents lead to the formation of the sulphone. Mixtures of the oxidised products are frequently obtained however, and these may be readily separated by standard techniques such as column chromatography.

(i) Preparation of 2-(4,4-Difluorobut-3-enylsulphinyl)benzoxazole (Compound No 9) and 2-(4,4-Difluorobut-3-enylsulphonyl)benzoxazole (Compound No 14)

2-(4,4-Difluorobut-3-enylthio)benzoxazole (Compound No 2, Example 4B(viii) 800 mg) in tert-butanol (20 cm$^3$) and water (12 cm $^3$) was treated with magnesium monoperoxyphthalic acid hexahydrate (1.64 g) and the mixture stirred at the ambient temperature for 16 hours. Gc showed some remaining starting material, and a further 350 mg of oxidant was added and the mixture stood for 60 hours. The reaction was quenched by the addition of saturated aqueous sodium carbonate and the product was extracted into ethyl acetate. The organic layer was washed with water and dried over anhydrous magnesium sulphate. Evaporation of the solvent under reduced pressure gave a mobile yellow oil (737 mg) which was subjected to chromatography on silica gel, eluting with 20% ethyl acetate in hexane, to give the sulphoxide (Compound A, 457 mg) and the corresponding sulphone (Compound B, 93 mg).

A: 2-(4,4-Difluorobut-3-enylsulphinyl)benzoxazole, yellow oil of poor chemical stability. $^1$H NMR (CDCl$_3$): δ2.45–2.75(m 2H); 3.35–3.55(m 2H); 4.2–4.4(m 1H); 7.4–7.55(m 2H); 7.65(dd 1H); 7.85(dd 1H).

B: 2-(4,4-Difluorobut-3-enylsulphonyl)benzoxazole, yellow oil; $^1$H NMR (CDCl$_3$): δ2.55–2.75(m 2H); 3.55–3.65(t 2H); 4.2–4.4(m 1H); 7.5–7.65(m 2H); 7.7(d 1H); 7.95(d 1H).

(ii) Preparation of 2-(4,4-difluorobut-3-enylsulphinyl)benzthiazole (Compound No 12).

2-(4,4-difluorobut-3-enylthio)benzthiazole (Compound No 1, Example 4D, 0.30 g) in dichloromethane (3 cm$^3$) was stirred at 0° C. and treated portionwise with meta-chloroperbenzoic acid (0.336 g of 50% reagent) and allowed to attain ambient temperature over 18 hr. The reaction mixture was diluted with diethyl ether, washed with dilute aqueous sodium hydrogen carbonate, water and dried (magnesium sulphate). The solvent was evaporated under reduced pressure to give a solid which was fractionated by eluting through a bed of silica using hexane/ethyl acetate 2:1 by volume to give the required product as a colourless solid, mp 67°–68° C.; M+ =274; ir 1750,1228 cm $^{-1}$; $^1$H NMR (CDCl$_3$): δ2.45(m 1H); 2.68(m 1H); 3.30(m 2H); 4.3(dtd 1H); 7.55(m 2H); 8.03(d 1H); 8.08(d 1H).

The following compounds were prepared according to the general method of Example 5(ii). Where mixtures of products were obtained, separation was by column chromatography.

(iii) 4,4-difluorobut-3-enyl 2-(4,4-difluorobut-3-enylsulphinyl)benzthiazole-5-carboxylate (A) (Compound No 92) and 4,4-difluorobut-3-enyl 2-(4,4-difluorobut-3-enylsulphonyl)benzthiazole-5-carboxylate (B) (Compound No 93) from 4,4-difluorobut-3-enyl 2-(4,4-difluorobut-3-enylthio)benzthiazole-5-carboxylate (Compound No 64, Example 6(xxiv)).

(A) colourless solid, mp 68°–70° C. (dec); M+ =407; $^1$H NMR (CDCl$_3$): δ2.50(m 2H); 2.80(m 4H); 3.30(m 2H); 4.20–4.35(m 4H); 8.08(d 1H); 8.17(dd 1H); 8.74(d 1H).

(B) colourless solid mp 69°–70° C.; M+ =423; $^1$H NMR (CDCl$_3$): δ2.50(m 2H); δ250(m 2H); 2.65(m 2H); 3.63(t 2H); 4.2–4.4(m 2H); 4.40(t 2H); 8.10(d 1H); 8.28(dd 1H); 8.88(d 1H).

(iv) 5-Bromo-2-(4,4-difluorobut-3-enylsulphinyl)benzthiazole (A) (Compound No 87) and 5-Bromo-2-(4,4-difluorobut-3enylsulphonyl)benzthiazole (B) (Compound No 88) from 5-Bromo-2-(4,4-difluorobut-3-enylthio)benzthiazole (Compound No 61, Example 4B(xviii))

A: colourless solid mp 107° C.; M+351; $^1$H NMR (CDCl$_3$): δ2 45(m 1H); 2.70(m 1H); 3.3(m 2H); 4.3(dtd 1H); 7.6(d 1H); 7.90(d 1H); 8.25(d 1H).

B: colourless solid mp 118° C.; M+ =367; $^1$H NMR (CDCl$_3$): δ2.60(m 2H); 3.6(t 2H); 4.3(dtd 1H); 7.7(dd 1H); 7.90(d 1H); 8.40(d 1H).

(v) 5-fluoro-2-(4,4-difluorobut-3-enylsulphinyl)benzthiazole (Compound No 95) from 5-fluoro-2-(4,4-difluorobut-3-enylthio)benzthiazole (Compound No 69, Example 4B(xxi));

colourless solid mp 84° C.; M+ =291; $^1$H NMR (CDCl$_3$): δ2.40(m 1H); 2.70(m 1H); 3.3(m 2H); 4.3(dtd 1H); 7.3(m 1H); 7.75(dd 1H); 7.95(dd 1H).

(vi) 5-(trifluoromethylthio)-2-(4,4-difluorobut-3-enylsulphinyl)benzthiazole (A) (Compound No 150) and 5-(trifluoromethylthio)-2-(4,4-difluorobut-3-enylsulphonyl)benzthiazole (B) (Compound No 151) from 5-(trifluoromethylthio)-2-(1,1-difluorobut-3-enylthio)-benzthiazole (Compound No 137, Example 4B(xxiv))

A: colourless solid mp 91°–93° C.; M+ =373; $^1$H NMR (CDCl$_3$): δ2.40(m 1H); 2.70(m 1H); 3.3(m 2H); 4.3(dtd 1H); 7.75(m 1H); 8.08(d 1H); 8.40(s 1H).

B: colourless solid mp 102°–104° C.; M+ =389; $^1$H NMR (CDCl$_3$): δ2.65(m 2H); 3.6(t 2H); 4.3(dtd 1H); 7.85(d 1H); 8.10(d 1H); 8.52(s 1H).

(vii) 6-nitro-2-(4,4-difluorobut-3-enylsulphinyl)benzthiazole (Compound No 160) from 6-nitro-2-(4,4-difluorobut-3-enylthio)benzthiazole (Compound No 52, Example 4B(xxviii)); $^1$H NMR (CDCl$_3$): δ9.00(1H d); 8.45(1H,dd); 8.20(1H,d); 4.3(1H,dtd); 3.35(2H,m); 2.7(1H,m); 2.42(1H,m)

(viii) 6-nitro-2-(4,4-difluorobut-3-enylsulphonyl)-benzthiazole (Compound No 161) from 6-nitro-2-(4,4-difluorobut-3-enylthio)benzthiazole (Compound No 52, Example 4B(xxviii)); $^1$H NMR (CDCl$_3$): δ9.00(1H,d); 8.50(1H,dd); 8.35(1H,d); 4.3(1H,dtd); 3.65(2H,t); 2.6(2H,m).

EXAMPLE 6

Procedures suitable for the preparation of compounds according to the invention by transformation or further reaction of the substituents of other compounds according to the invention are illustrated by the preparation of the following compounds:

(i) Preparation of 2-(4,4-difluorobut-3-enylthio)-4-methoxybenzoxazole (Compound No. 102).

To a stirred solution of 2-(4,4-difluorobut-3-enylthio)-4-hydroxy benzoxazole (Compound No. 82, Example 4B(iii), 504mg) in acetone (10 cm$^3$) was added iodomethane (278 mg) and potassium carbonate (270 mg). The reaction mixture was stirred at the ambient temperature for 5½ hours, then allowed to stand at the ambient temperature for 18 hours. Gc analysis indicated complete consumption of starting material. The reaction mixture was poured into ethyl acetate and and water, the layers separated and the aqueous phase extracted twice with ethyl acetate. The combined organic layers were washed with water, brine, dried (MgSO$_4$) and evaporated under reduced pressure to a yellow oil. Purification by silica-gel chromatography using 5% ethyl acetate in hexane as the eluent gave 2-(4,4-difluorobut-3-enylthio)-4-methoxy-benzoxazole as a colourless oil (290 mg). $^1$H NMR (CDCl$_3$) δ7.19(1H,t); 7.08(1H,d); 6.78(1H,d); 4.30(1H,ddt); 3.39(1H,t); 2.55(q).

The following three compounds were made by the method in example 6 (i) although they required heating to reflux to assure complete reaction.

(ii) 4-(4,4-difluorobut-3-enyloxy)-2-(4,4-difluorobut-3-enylthio)benzoxazole (Compound No. 101). $^1$H NMR (CDCl$_3$): δ7.16(1H,t); 7.09(1H,d); 6.78(1H,d); 4.40(2H,m); 4.33(2H,t); 3.35(2H,t); 2.54(4H,m); (oil).

(iii) 4-(2-fluoroethoxy)-2-(4,4-difluorobut-3-enylthio)benzoxazole (Compound No. 83). $^1$H NMR (CDCl$_3$): δ8 7.15(2H,m); 6.83(1H,d); 4.84(2H,td); 4.63(2H,d); 4.32(1H,ddt); 3.35(2H,t); 2.56(2H,q); (oil).

(iv) 4-(1-oxopropyloxy)-2-(4,4-difluorobut-3-enylthio)benzoxazole (Compound No. 100). $^1$H NMR (CDCl$_3$): δ7.34(1H,d); 7.23(1H,t); 7.04(1H,d); 4.30(1H,ddt); 3.31(2H,t); 2.62(2H,q); 2.55(2H,q); 1.32(3H,t); (oil).

(v) Preparation of 4-(1-oxopropylamino)-2-(4,4-difluorobut-3enylthio)benzoxazole (Compound No. 98).

To a stirred solution of 4-amino-2-(4,4-difluorobut-3-enylthio)benzoxazole (Compound No 80, Example 4B(iv), 255 mg) in dichloromethane (2 cm$^3$) and propionyl chloride (102 mg) at the ambient temperature was added dropwise triethylamine (120 mg) and the reaction stirred for 3½ hours, after which gc analysis indicated complete consumption of starting material. The reaction mixture was poured into ethyl acetate and water and the phases separated. The aqueous layer was extracted twice with ethyl acetate and the combined organic layers washed with water and brine and then dried (MgSO$_4$). Filtration and evaporation under reduced pressure gave a brown oil. Purification by silica gel chromatography using 30% t-butyl methyl ether in hexane as the eluent gave 4-(1-oxopropylamino)-2-(4,4-difluorobut-3-enylthio)benzoxazole as a pale yellow oil (124 mg). $^1$H NMR (DMSO): δ8.28(1H,d); 7.97(1H, b); 7.24(1H,t); 7.16(1H,d); 4.32(1H, ddt); 3.33(2H,t); 2.55(4H,m); 1.29(3H,t).

(vi) 4-(Methanesulphonamido)-2-(4,4-difluorobut-3-enylthio)benzoxazole (Compound No. 99).

To a stirred solution of 4-amino-2-(4,4-difluorobut-3-enylthio)benzoxaxole (Compound No 80, Example 4B(iv), 259 mg) and pyridine (80 mg) in dry toluene (5 cm$^3$) at the ambient temperature was added methanesulphonyl chloride (122 mg). The reaction was stirred for 6 hours and left to stand for 18 hours, after which gc analysis indicated complete reaction. The reaction mixture was poured into ethyl acetate and 2M hydrochloric acid and the layers separated. The ethyl acetate layer was washed with 2M hydrochloric acid, water and dried (MgSO$_4$). Filtration and evaporation under reduced pressure gave a brown liquid. Purification by silica gel chromatography gave 4-(methanesulphanamido)-2-(4,4-difluorobut-3-enylthio)benzoxazole as a brown solid (133mg). $^1$H NMR (CDCl$_3$) δ7.44(1H,d); 7.24(2H,m); 7.14(1H, bs); 4.32(1H, ddt); 3.32(2H,t); 2.56(1H,q).

(vii) Preparation of N-benzyl-2-(4,4-difluorobut-3-enylthio)benzoxazole-4-carboxamide (Compound No. 144).

A solution of p-toluenesulphonyl chloride (267 mg), pyridine (111 mg), and 2-(4,4-difluorobut-3-enylthio)-benzoxazole-4-carboxylic acid (Compound No. 97, Example 4E(i), 400mg) in dichloromethane (2 cm$^3$) was stirred at the ambient temperature for 4 hours and left to stand for 18 hours. Benzylamine (150 mg) was added and the reaction was heated at reflux for 1 hour. The reaction was poured into ether and water, the phases separated and the aqueous layer extracted twice with ether. The ether layer was dried to give a brown oil, purification using silica gel chromatography using 20% ethyl acetate in hexane gave a yellow solid (151 mg). $^1$H NMR (CDCl$_3$): δ9.23(1H, bt); 8.19(1H,d); 7.57(1H,d); 7.28–7.45(6H,m); 4.74(1H,d); 4.08(1H,ddt); 3.18(2H,t); 2.39(2H, bq).

(viii) N-benzyl-2-(4,4-difluorobut-3-enylthio)benzoxazole-5-carboxamide (Compound No. 158) was prepared according to the method of example 6 (vii) from 2-(4,4-difluorobut-3-enylthio)benzoxazole-4-carboxylic acid (Compound No. 94, Example 4E). $^1$H NMR (CDCl$_3$): δ8.00(1H,d); 7.77(1H,dd); 7.47(1H,d); 7.30–7.40 (5H,m); 6.42(1H bt); 4.78(1H,d); 4.31(1H, ddt); 3.32(2H, t); 2.57(2H bq).

(ix) Preparation of methyl 2-(4,4-difluorobut-3-enylthio)benzoxazole-5- carboxylate (Compound No. 146).

To a stirred solution of 2-(4,4-difluorobut-3-enylthio)-benzoxazole-5-carboxylic acid (400 mg) in dimethylformamide (5 cm$^3$) was added sodium hydrogen carbonate (224 mg) and methyl iodide (284 mg). The reaction mixture was stirred at the ambient temperature for 1 hour. The reaction mixture was filtered through Highflo to remove solid material and the filtrate evaporated to give a yellow oil. This oil was taken up in ether and washed with water. The ether was dried (MgSO$_4$) and evaporated to give a yellow oil when crystallised on standing. Recrystallisation from hexane gave methyl 2-(4,4-difluorobut-3-enylthio)benzoxazole-5-carboxylate as a white solid (31 mg). $^1$H NMR (CDCl$_3$): δ8.29(1H,d); 8.03(1H,dd); 7.48(1H,d); 4.32(1H,ddt); 3.94(3H,s); 3.36(2H,t); 2.58(2H bq).

(x) Preparation of 4,4-difluorobut-3-enyl 2-(4,4-difluorobut-3-enylthio)benzoxazole-5-carboxylate (Compound No. 118).

To a stirred solution of 4,4-difluorobut-3-enyl p-toluenesulphonate (870 mg) in acetontrile (10 cm$^3$) at the ambient temperature was added potassium iodide (550 mg) and the reaction mixture was heated at 80° C. for ½ hour during which time a precipitate formed. A solution of 2-(4,4-difluorobut-3-enylthio)benzoxazole-5-carboxylic acid (301 mg) and ethyldiisopropylamine (567 mg) in acetonitrile (5 cm$^3$) was added to the reaction mixture and heating at 80° C. was continued for 4 hours after which time gc analysis indicated complete consumption of starting materials. The reaction mixture was allowed to cool and then poured into ethyl acetate and water. The phases were separated and the aqueous layer extracted twice with ethyl acetate. The combined organic layers were washed with water, brine and dried (MgSO$_4$). Filtration and evaporation under reduced pressure gave a brown oil. Purification by silica gel chromatography using 4% ethyl acetate in hexane as the eluent gave a pale yellow oil (134 mg). $^1$H NMR (CDCl$_3$): δ8.29(1H,d); 8.01(1H,dd); 7.48(1H,d); 4.35(2H, t); 4.30(2H,m); 3.37(2H,t); 2.58(2H,q); 2.48(2H,q).

(xi) Preparation of 6-Acetoxy-2-(4,4-difluorobut-3-enylthio)benzoxazole (Compound No 55).

2-(4,4-Difluorobut-3-enylthio)-6-hydroxybenzoxazole (Compound No 54, Example 4A, 600 mg) was added to acetic anhydride (4 cm$^3$) and the mixture heated at 50° C. for 4.5 hours. The reaction was allowed to cool overnight. Excess acetic anhydride was removed by evaporation under reduced pressure and the residual oil was triturated with water. The solid which crystallised was collected by filtration and washed with water. This crude product was further purified by chromatography on silica gel, eluting with 10% ethyl acetate in hexane. The colourless oil obtained solidified on standing to give a white solid (570 mg) mp 48.6°–50.4° C.; M$^+$=299; $^1$H NMR (CDCl$_3$): δ2.35(s 3H); 2.5–2.6(m 2H); 3.3(t 2H); 4.2–4.4(m 1H); 7.0(dd 1H); 7.25(d 1H); 7.60(d 1H).

(xii) Preparation of 2-(4,4-Difluorobut-3-enylthio)-6-methanesulphonyloxybenzoxazole (Compound No 60).

2-(4,4-Difluoro-but-3-enylthio)-6-hydroxybenzoxazole (Compound No 54, Example 4A, 600 mg) was dissolved in dry dichloromethane (6 cm$^3$) and placed under an atmosphere of nitrogen. The mixture was cooled in an ice-water bath and triethylamine (354 mg) and methanesulphonyl chloride (334 mg) were added. The cold mixture was stirred for 45 minutes and then allowed to warm to room temperature for 4 hours. 1.4M aqueous HCl and more dichloromethane was added and the product was extracted into dichloromethane. The organic layer was washed with saturated brine and dried over magnesium sulphate. Concentration by evaporation under reduced pressure gave a white solid (760 mg); mp 87°–89° C.; M$^+$=335; $^1$H NMR (CDCl$_3$): δ2.5–2.6 (m 2H), 3.15 (s 3H), 3.3–3.4 (t 2H), 4.25–4.4 (m 1H), 7.25 (dd 1H), 7.45 (d 1H), 7.6 (d 1H).

(xiii) Preparation of 2-(4,4-Difluorobut-3-enylthio)-6-(prop-2-enyloxy)benzoxazole (Compound No 147).

2-(4,4-Difluorobut-3-enylthio)-6-hydroxybenzoxazole (Compound No 54, Example 4A, 300 mg) was dissolved in dimethyl formamide (DMF, 7 cm$^3$) and potassium carbonate (241 mg) and allyl bromide (197 mg) were added. The mixture was warmed at 50° C. for 4 hours, when tlc showed that the reaction was complete. The reaction was left to stand at room temperature for 70 hours then worked up by addition of excess aqueous hydrochloric acid and extraction into diethyl ether. The ethereal layer was washed with water and dried over anhydrous magnesium sulphate. Concentration by evaporation under reduced pressure gave an orange oil (315 mg); M$^+$=297; $^1$H NMR (CDCl$_3$): δ2.5–2.6(m 2H); 3.3(t 2H); 4.2–4.4(m 1H); 4.55(d 2H); 5.3(d 1H): 5.4–5.45(d 1H); 6.0–6.15(m 1H); 6.9(dd 1H); 7.0(d 1H); 7.45(d 1H).

The following two compounds were prepared from 2-(4,4-difluorobut-3-enylthio)-6-hydroxybenzoxazole by alkylation in a procedure similar to that of Example 6(xiii):

(xiv) 6-(3,3-Dichloroprop-2-enyloxy)-2-(4,4-difluorobut-3-enylthio)benzoxazole (Compound No 105). M$^+$=365; $^1$H NMR (CDCl$_3$): δ2.5–2.6(m 2H); 3.3(t 2H); 4.2–4.4(m 1H); 4.65(d 2H); 6.15(t 1H); 6.85(dd 1H); 7.0(d 1H); 7.5(d 1H); (oil).

(xv) 6-(2-Chloroprop-2-enyloxy)-2-(4,4-Difluorobut-3enylthio)benzoxazole (Compound No 104). M$^+$=331; $^1$H NMR (CDCl$_3$): δ2.5–2.6(m 2H); 3.3(t 2H); 4.2–4.4(m 1H); 4.6(s 2H); 5.45(s 1H); 5.55(s 1H); 6.95(dd 1H); 7.05(d 1H); 7.5(d 1H); (oil).

(xvi) Preparation of 2-(4,4-Difluorobut-3-enylthio)-benzoxazole-6carboxylic acid (Compound No 84).

Methyl 2-(4,4-difluorobut-3-enylthio)benzoxazole-6-carboxylate (Compound No 10, Example 4B(ix), 600 mg) was dissolved in tetrahydrofuran (4 cm ) and water (4 cm ) and treated with lithium hydroxide monohydrate (88 mg). The mixture was stirred at the ambient temperature for 6 hours. Tlc showed that some starting material was still present, so a further amount of lithium hydroxide monohydrate (88 mg) was added and stirring continued for 16 hours. The reaction mixture was diluted with water and extracted with diethyl ether. These extracts were discarded. The aqueous solution was acidified using 1.4M hydrochloric acid to pH 4 and the product was extracted using diethyl ether. The ether layer was dried over anhydrous magnesium sulphate and concentrated under reduced pressure to give a cream solid (820 mg). This material was triturated in dichloromethane, the insoluble material being discarded. Evaporation of the dichloromethane solution under reduced pressure gave the product (317 mg) as a cream solid; mp 115.8°–118.4° C.; M$^+$=285; $^1$H NMR (CDCl$_3$): δ2.5–2.65 (m 2H), 3.3–3.4 (t 2H), 4.2–4.4 (m 1H), 2–5 (br 1H), 7.65 (d 1H), 8.1–8.15 (dd 1H), 8.2 (d 1H).

(xvii) Preparation of N-Ethyl-N-methyl 2-(4,4-Difluoro-but-3-enylthio)-benzoxazole-6-carboxamide (Compound No 109).

Methyl ethylamine (503 mg) was dissolved in 1,2-dichloroethane (15 cm$^3$) and trimethylaluminium (4.26 cm of a 2M solution in hexane) was added. The initially cloudy solution was stirred at room temperature for 45 minutes, by which time it had become clear. Methyl 2-(4,4-difluorobut- 3-enylthio)benzoxazole-6-carboxylate (Compound No 10, Example 4B(ix), 425 mg) in 1,2-dichloroethane (7.5 cm$^3$) was added to this solution and the mixture heated at 50° C. for 18 hours. Excess aluminium reagent was then hydrolysed by addition of water and dichloromethane was used to extract the product. The organic layer was washed with saturated brine and dried over anhydrous magnesium sulphate. Evaporation of the solvent under reduced pressure gave a brown oil (361 mg) which was subjected to chromatography on silica gel, eluting with 35% ethyl acetate in hexane. The product (205 mg) was obtained as a colourless oil. M$^+$=326; $^1$H NMR (CDCl$_3$): δ1.1–1.3(m 3H); 2.5–2.65(m 2H); 2.9–3.1(m 3H); 3.35(t 2H); 3.4–3.65(m 2H); 4.2–4.4(m 1H); 7.3–7.4(dd 1H); 7.5(d 1H); 7.6(d 1H).

(xviii) Preparation of 6-Cyano-2-(4,4-difluorobut-3-enylthio)benzoxazole (Compound No 107) and 2-(4,4-

Difluorobut-3-enylthio)benzoxazole-6-carboxamide (Compound No 108)

Ammonium chloride (389 mg) was suspended in 1,2-dichloroethane (10 cm$^3$) and trimethylaluminium (3.6 cm$^3$ of a 2M solution in hexane) was added. The initially cloudy solution was stirred at the ambient temperature for 50 minutes, by which time it had become clear. Methyl 2-(4,4-difluorobut-3-enylthio)benzoxazole-6-carboxylate (Compound No 10, Example 4B(ix), 363 mg) in 1,2-dichloroethane (10 cm$^3$) was added to this solution and the mixture heated at 50° C. for 18 hours. Excess aluminium reagent was then hydrolysed by addition of water and dichloromethane was used to extract the product. The organic layer was washed with saturated ammonium chloride solution and dried over anhydrous magnesium sulphate. Evaporation of the solvent under reduced pressure gave an off-white solid (306 mg) which was subjected to chromatography on silica gel, eluting first with 20% ethyl acetate in hexane and then neat ethyl acetate. The benzoxazole-containing products obtained from this column were:

6-cyano-2-(4,4-difluorobut-3-enylthio)benzoxazole (Compound No 107, 56 mg), a colourless oil, M+ =266; $^1$H NMR (CDCl$_3$): δ2.5-2.65 (m 2H) 3.3-3.4 (t 2H), 4.2-4.4 (m 1H), 7.6-7.7 (m 2H), 7.75 (s 1H); and 2-(4,4-Difluoro-but-3-enylthio)benzoxazole-6-carboxamide (Compound No. 108). mp 126°-128.4° C.; M+ =284; $^1$H NMR (CDCl$_3$): δ2.55-2.65 (m 2H), 3.3-3.4 (t 2H), 4.2-4.4 (m 1H), 5.6-6.0 (br s 2H), 7.6 (d 1H), 7.75 (dd 1H), 7.95 (d 1H).

(xix) Preparation of 6-Acetylamino-2-(4,4-difluorobut-3-enylthio)benzoxazole (Compound No 49)

6-Amino-2-(4,4-difluorobut-3-enylthio)benzoxazole (Compound No 6, Example 4F, 180 mg) was stirred in acetic anhydride (3.5 cm$^3$) at 50° C. for 8 hours. The reaction mixture was allowed to cool and stood for 16 hours. Excess acetic anhydride was removed by evaporation at reduced pressure, including co-evaporations with dichloromethane to remove the last traces. The residue (202 mg) was subjected to chromatograpy on silica gel, eluting with 40% ethyl acetate in hexane. The product was obtained as a cream solid; mp 87.6°-88.8° C.; M+ =298; $^1$H NMR (CDCl$_3$): δ2.35 (s 3H), 2.65-2.75 (m 2H), 3.4-3.5 (t 2H), 4.4-4.55 (m 1H), 7.25 (dd 1H), 7.55 (br s 1H), 7.6-7.65 (d 1H), 8.2 (d 1H).

(xx) Preparation of N-[2-(4,4-Difluorobut-3-enylthio)benzoxazol-6yl]formamide (Compound No 85)

6-Amino-2-(4,4-difluorobut-3-enylthio)benzoxazole (Compound No 6, Example 4F, 213 mg) in dichloromethane (5 cm$^3$) was treated with trimethylacetic formic anhydride and stirred at the ambient for 4.5 hours. Evaporation of the solvent and excess mixed anhydride under reduced pressure gave an off-white solid (315 mg). This was subjected to chromatography on silica gel, eluting with 35% ethyl acetate in hexane. The product (210 mg) was obtained as a white solid; mp 104.6°-106° C.; M+ =284; $^1$H NMR (CDCl$_3$): δ2.6-2.7 (m 2H), 3.25-3.35 (m 2H), 4.2-4.4 (m 1H), 7.0-7.15 (dd 1H), 7.2-7.6 (m 2H), 8.1-8.4 (m 1H), 8.65 (m 1H).

(xxi) Preparation of 6-[N,N-di-(methanesulphonyl)amino]-2-(4,4-difluorobut-3-enylthio)benzoxazole (Compound No 53)

6-Amino-2-(4,4-difluorobut-3-enylthio)benzoxazole (Compound No 6, Example 4F, 180 mg) in dichloromethane (3.5 cm$^3$) was treated with triethylamine (106 mg) and methanesulphonyl chloride (100 mg) and stirred at the ambient temperature for 6 hours. The product was extracted into dichloromethane and the organic layer washed with dilute aqueous hyrochloric acid and water, before drying over anhydrous magnesium sulphate. Evaporation of solvent under reduced pressure gave a cream solid (280 mg). This was subjected to chromatography on silica gel, eluting with 20% ethyl acetate in hexane. The product (230 mg) was obtained as a white solid; mp 127.6°-130.4° C.; M+ =412; $^1$H NMR (CDCl$_3$): δ2.5-2.65 (m 2H), 3.3-3.41 (t 2H), 3.45 (s 6H), 4.2-4.4 (m 1H), 7.3 (dd 1H), 7.5 (d 1H), 7.65 (d 1H).

(xxii) Preparation of 6-Chloro-2-(4,4-difluorobut-3-enylthio)benzoxazole (Compound No 45)

Cupric chloride (126 mg) was dissolved in acetonitrile (6 cm$^3$) and the orange solution cooled in an ice-water bath. Tert-butyl nitrite (161 mg) was added and then 6-amino-2-(4,4-difluorobut-3-enylthio)benzoxazole (compound no 6, example 4f, 200 mg) in acetonitrile (4 cm$^3$) was added dropwise over a period of five minutes. The mixture was stirred in the ice-bath for 45 minutes then allowed to warm to room temperature and stirred for a further 3.5 hours. The reaction mixture was poured into dilute aqueous hydrochloric acid and the product was extracted into diethyl ether. The organic layer was washed with saturated brine and dried over magnesium sulphate. Evaporation of solvent under reduced pressure gave a dark brown gum (236 mg). This was subjected to chromatography on silica gel, eluting with 5% ethyl acetate in hexane. The product (87 mg) was obtained as a pale yellow oil; M+ =275; $^1$H NMR (CDCl$_3$): δ2.5-2.6 (m 2H), 3.35 (t 2H), 4.2-4.4 (m 1H), 7.3 (dd 1H), 7.45 (d 1H), 7.5 (d 1H);

(xxiii) Preparation of 6-Amino-2-(4,4-difluorobut-3-enylthio)benzthiazole (Compound No 148).

2-(4,4-difluorobut-3-enylthio)-6-nitrobenzthiazole (Compound No 52, Example 4B(xxviii), 2.8 g) was dissolved in propan-2-ol (50 cm$^3$) containing water (12 cm$^3$), concentrated hydrochloric acid (four drops) and reduced iron powder (5.0 g, Aldrich Chemical Co.). The mixture was stirred and heated to reflux for 1.5 hr., filtered through a bed of silica, cooled to ambient temperature and neutralised with aqueous sodium bicarbonate. The solution was evaporated under reduced pressure, redissolved in diethyl ether, dried (magnesium sulphate) and evaporated to give the required product as a a brown oil which partially solidified on cooling.

M+ =272; $^1$H NMR (CDCl$_3$): δ2.50(m 2H); 3 32(t 2H); 3.75 (broad signal 2H); 4.3(dtd 1H); 6.75(dd 1H); 7.00(d 1H); 7.65(d 1H).

(xxiv) Preparation of 4,4-difluorobut-3-enyl 2-(4,4-difluorobut-3-enylthio)benzthiazole-5-carboxylate (Compound No 64).

This compound may be prepared from 2-(4,4-difluorobut-3-enylthio)benzthiazole-5-carboxylic acid (Compound No 68, Example 4E(ii)) using the method of Example 6(x). $^1$H NMR (CDCl$_3$):δ2.55(m 4H); 3.45(t 2H); 4.2-4.4(m 4H); 7.80(d 1H); 7.98(dd 1H); 8.50(d 1H).

(xxv) Preparation of N-[2-(4,4-difluorobut-3-enylthio)benzthiazol-6-yl]-benzamide (Compound No 134).

6-Amino-2-(4,4-difluorobut-3-enylthio)benzthiazole (Compound No 148, Example 6(xxiii), 0.30 g) in dry dichloromethane (2 cm$^3$) containing benzoyl chloride (0.17 g) and triethylamine (0.12 g) were stirred for 3hr., diluted with water and extracted with ethyl acetate (3×10 cm$^3$). The combined organic phases were washed with brine (3×20 cm$^3$), dried (magnesium sulphate) and evaporated under reduced pressure. The residue was eluted through a bed of silica using a mixture of hexane and ethyl acetate in a volume ratio varied from 4:1 to 1:1 to give the required product as a colourless solid, mp 124°–125° C.; M+ =376; $^1$H NMR (CDCl$_3$): δ2.55(m 2H); 3.4(t 2H); 4.3(dtd 1H); 7.40(dd 1H); 7.50(m 3H); 7.90(d 12H); 7.95(broad signal 1H); 8.15(d 1H); 8.50(d 1H)

(xxvi) Preparation of N-[2-(4,4-difluorobut-3-enylthio)benzthiazol-6yl]-propionamide (Compound No 50).

This compound was prepared according to the method of Example 6(xxv) from Compound No 148, and propionyl chloride, using pyridine as the base. Colourless solid mp 100°–101° C.; M+ =328; $^1$H NMR (CDCl$_3$): δ1.20(m 3H); 2.25–2.50(m 4H); 3.3(t 2H); 4.25(dtd 1H); 7.20(s 1H); 7.70(d 1H); 8.3(broad signal 1H).

(xxvii) Preparation of N-[2-(4,4-difluorobut-3-enylthio)benzthiazol-6-yl]-methanesulphonamide (Compound No 51).

6-Amino-2-(4,4-difluorobut-3-enylthio)benzthiazole (Compound No 148, Example 6(xxiii), 0.56 g) was stirred at ambient temperature in dry toluene (5 cm$^3$) containing dry pyridine (0.16 g) and treated with methanesulphonyl chloride (0.23 g) in toluene (5 cm$^3$). On complete addition the mixture was stirred for 3 hr., stored for 18 hr, diluted with ethyl acetate, washed with dilute aqueous hydrochloric acid, water and the organic phase dried (magnesium sulphate). The solvent was removed under reduced pressure and the oil obtained fractionated by eluting through a column of silica with hexane/ethyl acetate (2;1) by volume to give the the required product as an orange brown solid,mp 79.5°–81.0° C.; M+ =350; ir 3200,1756,1326 cm$^{-1}$; $^1$H NMR (CDCl$_3$): δ2.55(q 2H); 3.05(s 3H); 3.40(t 2H); 4.30(dtd 1H); 6.7 (broad signal 1H); 7.23(dd 1H); 7.77(d 1H); 7.83(d 1H).

(xxviii) Preparation of 2-(4,4-difluorobut-3-enylthio)-benzthiazole-5-carboxamide (Compound No 65).

2-(4,4-difluorobut-3-enylthio)benzthiazole-5-carboxylic acid (Compound No 68, Example 4E(ii), 0.72 g) in dry dichloromethane (15 cm$^3$) at 0° C. was stirred and treated with dry triethylamine (0.35 cm$^3$). Ethyl chloroformate (0.25 cm$^3$) was added dropwise, and the mixture kept at ambient temperature for 2 hr. Ammonia gas was then bubbled into the solution until in excess. The reaction mixture was stirred for 1 hr. and aqueous ammonia added. The reaction was extracted with dichloromethane (3×100 cm$^3$), washed with water, dilute aqueous hydrochloric acid, water and dried (magnesium sulphate). The solvent was evaporated under reduced pressure and the solid obtained was fractionated by eluting through a bed of silica using hexane/ethyl acetate (1:1 by volume) to give the required product as a colourless solid,mp 119°–120° C.; M+ =300; ir 3322,3148,1750,1670,1546,1418 cm$^{-1}$; $^1$H NMR (CDCl$_3$): δ2.55(m 2H); 3.40(t 2H); 4.3(dtd 1H); 6.0(broad signal 2H); 7.82(m 2H); 8.25(s 1H).

The following two compounds were prepared by a procedure similar to that of Example 6(xxviii):

(xxix) N,N-Dimethyl 2-(4,4-difluorobut-3-enylthio)-benzthiazol-5-carboxamide (Compound No 67); colourless oil, M+ =328, ir 1754,1640 cm$^{-1}$; $^1$H NMR (CDCl$_3$): δ2.55(m 2H); 3.1(two broad signals 6H); 3.43(t 2H); 4.3(dtd 1H); 7.38(dd 1H); 7.80(d 1H); 7.90(d 1H).

(xxx) N-1-Propyl 2-(4,4-difluorobut-3-enylthio)benzthiazol-5-carboxamide (Compound No 66); colourless solid mp 72°–73° C.; M+ =342; ir 3296 1752 1634 cm$^{-1}$; $^1$H NMR (CDCl$_3$): δ1.0(t 3H); 1.68(q 2H); 2.55(m 2H); 3.45(m 4H); 4.30(dtd 1H); 7.78(m 2H); 8.18(d 1H).

(xxxi) Preparation of 5-Cyano-2-(4,4-difluorobut-3-enylthio)benzthiazole (Compound No 91).

2-(4,4-difluorobut-3-enylthio)benzthiazol-5-carboxamide (Compound No 65, Example 6(xxviii), 0.32 g) in dry dichloromethane (13 cm$^3$) was stirred and treated at ambient temperature with pyridine (dry, 1 cm$^3$) and methanesulphonyl chloride (0.25 cm$^3$). The mixture was stored for 4 days to complete the reaction, diluted with water, extracted into dichloromethane and the organic phase washed with dilute hydrochloric acid, water and dried (magnesium sulphate). The solvent was evaporated under reduced pressure and the oil obtained fractionated by eluting through a bed of silica using hexane/ethyl acetate (20:1 by volume) to give the required product as a colourless solid mp 39.5°–40.5° C.; M+ =282; ir 2232 1750 cm$^{-1}$; $^1$H NMR (CDCl$_3$): δ2.55(m 2H); 3.45(t 2H); 4.30(dtd 1H); 7.55(dd 1H); 7.85(d 1H); 8.15(d 1H).

(xxxii) Preparation of 2-(4,4-Difluorobut-3-enylthio)-6-methylthiobenzthiazole (Compound No 86)

6-Amino-2-(4,4-difluorobut-3-enylthio)benzthiazole (Compound No 148, Example 6(xxiii), 0.544 g) in dry dichloromethane (10 cm$^3$) containing dimethyldisulphide (0.94 g) was treated dropwise at 0° C. with tert-butyl nitrite (0.227 g) in dichloromethane (3 cm$^3$). The reaction was allowed to reach ambient temperature and stored for 2 days to completely react. The reaction solution was evaporated under reduced pressure onto silica, added to a bed of silica and eluted with hexane/ethyl acetate (50:1 by volume) to give the required product as a colourless oil. M+ =303; ir 1750 cm$^{-1}$; $^1$H NMR (CDCl$_3$): δ2.55(m 5H); 3.38(t 2H); 4.30(dtd 1H); 7.35(dd 1H); 7.64(d 1H); 7.75(d 1H).

(xxxiii) Preparation of methyl 2-(4,4-difluorobut-3-enylthio)benzoxazole-4-carboxylate (Compound No 152).

This compound may be prepared from 2-(4,4-difluorobut-3-enylthio)benzoxazole-4-carboxylic acid (Compound No 97, Example 4E(i)) using the method of Example 6(x). $^1$H NMR (CDCl$_3$): δ7.95(1H,d); 7.63(1H,d); 7.30(1H,d); 4.32(1H,ddt); 4.00(3H,s); 3.40(2H,t); 2.59(2H,q).

(xxxiv) Preparation of 2-fluoroethyl 2-(4,4-difluorobut-3-enylthio)benzoxazole-5-carboxylate (Compound No 153).

This compound may be prepared from 2-(4,4-difluorobut-3-enylthio)benzoxazole-5-carboxylic acid (Compound No 94, Example 4E) using the method of Example 6(ix). $^1$H NMR (CDCl$_3$): δ8.34(1H,bs); 8.06(1H,dd); 7.49(1H,d); 4.80–4.90(1H,m); 4.60–4.70(2H,m); 4.50–4.58(1H,m); 4.32(1H,dtd); 3.36(2H,t); 2.59(2H,bq).

(xxxv) Preparation of 2-(4,4-difluorobut-3-enylthio)-6-iodobenzthiazole (Compound No 141).

6-Amino-2-(4,4-difluorobut-3-enylthio)benzthiazole (Compound No 148, Example 6(xxiii), 0.5 g) in dry acetonitrile (10 cm$^3$) was added dropwise to a stirred mixture of copper(I) iodide (0.5 g) and tert-butyl nitrite (1.85 g) in dry acetonitrile (10 cm$^3$) at 0° C. under an atmosphere of nitrogen. After 2 hr. the mixture was allowed to reach ambient temperature and was stirred for a further 18 hr., poured into water acidified with dilute hydrochloric acid and extracted into ethyl acetate (3×20 cm$^3$). The combined organic phase was washed with water, brine, dried (magnesium sulphate) and evaporated under reduced pressure. The residual product was fractionated by eluting through a column of silica using hexane/ethyl acetate (19:1 by volume) to give the required product as a light brown oil. M+=383; ¹H NMR (CDCl₃): δ8.10(1H,d); 7.60(1H,d); 7.65(1H,dd); 4.3(1H,dtd); 3.4(2H,t); 2.55(2H,m)

(xxxvi) 2-(4,4-Difluorobut-3-enylthio)-6-ethynylbenzthiazole (Compound No 155).

2-(4,4-difluorobut-3-enylthio)-6-iodobenzthiazole (Compound No 141, Example 6(xxxv), 0.1 g) was dissolved in N,N-dimethyl formamide (1 cm³) containing trimethylsilylacetylene (0.025 g), copper(I) iodide (0.005 g), triethylamine (0.5 g) and bis(triphenylphosphine)palladium(II) chloride (0.009 g). The mixture was stirred under an atmosphere of nitrogen at ambient temperature for 2 hr., stored for 18 hr., poured into water and extracted into diethylether. The organic phase was washed with water (5×30 cm³), dried (magnesium sulphate) and evaporated under reduced pressure to give an oil containing 2-(4,4-Difluorobut-3-enylthio)-6-(trimethylsilylethynyl)benzthiazole (M+=353). A portion of the oil (0.021 g) was dissolved in tetrahydrofuran (1 cm³) and the stirred solution treated at ambient temperature with a solution of tetrabutylammonium fluoride in terahydrofuran (0.06 cm³ of 1.0M solution, Aldrich Chemical Co). The reaction was stirred for 2 hr., diluted with water, extracted with ethyl acetate and evaporated under reduced pressure to give an oil which was fractionated using preparative thin layer chromatography (silica; hexane/ethyl acetate 9:1 by volume) to give the required product as an oil. M+=281; ¹H NMR (CDCl₃): δ7.88(1H s); 7.78(1H,d); 7.52(1H,d); 4.3(1H,dtd); 3.40(2H,t); 3.12(1H,s); 2.56(2H,q).

The following four compounds were prepared from 2-(4,4-difluorobut-3-enylthio)-6-hydroxybenzoxazole by alkylation in a procedure similar to that of Example 6(xiii):

(xxxvii) 2-(4,4-difluorobut-3-enylthio)-6-(2-fluoroethoxy)-benzoxazole (Compound No. 110). M+=303; ¹H NMR (CDCl₃): δ2.5–2.6(2H,m); 3.25–3.35(2H,t); 4.15–4.40(3H,m); 4.7–4.9(2H,dt); 6.9(1H,dd); 7.0(1H,d); 7.45(1H,d); (oil).

(xxxviii) 2-(4,4-difluorobut-3-enylthio)-6-propoxybenzoxazole (Compound No. 111). M+=299; ¹H NMR (CDCl₃): δ1.05(3H t); 1.75–1.9(2H,m); 2.5–2.6(2H,m); 3.3(2H,t); 3.95(2H,t); 4.2–4.4(1H,m); 6.9(1H,dd); 7.0(1H,d); 7.45(1H,d); (oil).

(xxxix) 2-(4,4-difluorobut-3-enylthio)-6-(but-2-yloxy)-benzoxazole (Compound No. 112). M+=313; ¹H NMR (CDCl₃): δ0.95(3H t); 13(3H d); 1.6–1.85(2H,m); 2.5–2.6(2H,m); 3.3(2H,t); 4.2–4.4(2H,m); 6.85(1H,dd); 7.0(1H,d); 7.45(1H,d); (oil).

(xi) 2-(4,4-difluorobut-3-enylthio)-6-(ethoxycarbonylmethoxy)benzoxazole (Compound No. 106). M+=343; ¹H NMR (CDCl₃): δ8.13(3H,t); 2.5–2.6(2H,m); 3.3(2H,t); 4.2–4.4(3H,m); 4.65(2H,s); 6.9(1H,dd); 7.0(1H,d); 7.5(1H,d); (oil).

EXAMPLE 7

This Example illustrates the preparation of miscellaneous starting materials of use in the preparation of compounds according to the invention and intermediates therefor.

(i) 4-Step preparation of 4-trifluoromethylthio-2-nitrochlorobenzene (starting material for Example 1A(vi).

Step 1: 4-trifluoromethylthioacetanilide

Acetic anhydride (5.9 cm³) was added dropwise to 4-aminophenyl trifluoromethyl sulphide (10.0 g) in acetic acid (18 cm³) to give a solid suspension. The mixture was poured into ice/water and the solid was filtered, washed with water dichloromethane, then dried by suction to give the required product; mp 188° C.; M+=235; ¹H NMR (CDCl₃): δ2.15(s 3H); 7.55(d 2H); 7.70(d 2H); 9.50(broad signal 1H).

Step 2: 2-nitro-4-trifluoromethylthioacetanilide

4-Trifluoromethylthioacetanilide (12.2 g) was stirred in dichloromethane (200 cm³) and treated dropwise with fuming nitric acid (10.5cm³). The solution was stirred for 2 hr., stored for 18 hr. at ambient temperature, poured into ice/water and neutralised using aqueous sodium hydrogen carbonate. The organic phase was separated, washed with water, dried (magnesium sulphate) and evaporated under reduced pressure to give the required product as a yellow solid; mp 106° C.; M+=280; ¹H NMR (CDCl₃): δ2.35(s 3H); 7.90(dd 1H); 8.55(d 1H); 8.95(d 1H).

Step 3: 2-nitro-4-trifluoromethylthioaniline

2-Nitro-4-trifluoromethylthioacetanilide (10.5 g) in ethanol (200 cm³) containing potassium hydroxide (2.2 g) was heated to reflux with stirring for 0.25 hr., cooled to ambient temperature and poured into water. The solid which precipitated was filtered from solution, washed with water and sucked to dryness to give the required product, mp 86° C.; M+=238; ¹H NMR (CDCl₃): δ6.45(broad signal 2H); 6.90(d 1H); 7.60(dd 1H); 8.50(d 1H).

Step 4: Preparation of 4-trifluoromethylthio-2-nitrochlorobenzene

2-Nitro-4-trifluoromethylthioaniline (0.5 g) in dry acetonitrile (3 cm³) was added over 0.5 hr. with stirring to copper (II) chloride (0.34 g) and tert-butyl nitrite (0.32 g) in dry acetonitrile (5 cm³) at 60° C. After 1 hr. the reaction was cooled to ambient temperature, poured into water, acidified with hydrochloric acid and extracted with ethyl acetate. The organic phase was washed with water (3×50 cm³) dried (magnesium sulphate) and evaporated under reduced pressure to give the required product as an oil; M+=257; ¹H NMR (CDCl₃): δ7.65(d 1H); 7.80(dd 1H); 8.20(d 1H).

(ii) Preparation of N,N-Dimethyl 4-chloro-3-nitrobenzenesulphonamide (starting material for Example 1A(ix).

4-Chloro-3-nitrobenzenesulphonyl chloride (3.0 g) in toluene (20 cm³) was treated with dimethylamine (1.1 g) in water (10 cm³) and stirred for 2 hr. The reaction was stored for 18 hr., poured into water, extracted with ethyl acetate (3×20 cm³), and the combined organic phase washed with brine (3×20 cm³), dried (magnesium sulphate) and evaporated under reduced pressure to give the title product as a yellow solid, mp 88° C.; M+=274; ¹H NMR (CDCl₃): δ2.90(s 6H); 7.90(d 1H); 8.10(dd 1H); 8.40(d 1H).

(iii) Two step preparation of 2-nitro-4-trifluoromethylsulphinylbromobenzene (a) and 2-nitro-4-trifluoromethylsulphonylbromobenzene (b) (starting materials for example 1a(vii)).

Step 1: 4-Bromotrifluoromethylsulphinylbenzene and 4-bromotrifluoromethylsulphonylbenzene 4-Bromotrifluoromethylthiobenzene (5.0 g) in dichloromethane (50 cm³) was stirred at 0° C. and treated portionwise with meta-chloroperbenzoic acid (6.7 g of 50% reagent) and allowed to attain ambient temperature over 18 hr. The mixture was washed with aqueous sodium hydrogen carbonate, water, dried (magnesium sulphate) and evaporated under reduced pressure to give a mixture of the sulphoxide and sulphone (ratio 3:1) which was used in the next stage:

Step 2: The mixture from Step 1 (5.4 g) was dissolved in concentrated sulphuric acid (20 cm$^3$) at ambient temperature and the stirred solution treated portionwise with potassium nitrate (2.02 g). The reaction was stirred for 3 hr., poured into ice/water, extracted with ethyl acetate and the organic phase washed with water, dried (magnesium sulphate) and evaporated under reduced pressure. The residual product was eluted through a column of silica using hexane/ethyl acetate (9:1 by volume) to give a mixture of the required products. M+(A) (M-NO)=287; (B) (M-NO) 305. An alternative synthesis of (B) is given in J. Org. Chem. (1960) 25 60.

EXAMPLE 8

The activity of the compounds of formula (I) was determined using a variety of pests. The pests were treated with a liquid composition containing 500 parts per million (ppm) by weight of the compound unless otherwise stated. The compositions were made by dissolving the compound in acetone and diluting the solutions with water containing 0.01% by weight of a wetting agent sold under the trade name "SYNPERONIC" NX until the liquid composition contained the required concentration of the compound. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the medium and the pests with the compositions. The mortality of the pests was then assessed at periods usually varying from one to three days after the treatment.

The results of the tests are presented in Table II for each of the compounds at the rate in parts per million given in the second column. The results indicate a grading of mortality designated as A, B or C wherein A indicates less than 50% mortality, B indicates 50–79% mortality and C indicates 80–100% mortality (figures indicate knockdown control for test MDb);—indicates that either the compound was not tested or no meaningful result was obtained.

Information regarding the pest species, the support medium or food, and the type and duration of the test is given in Table II. The pest species is designated by a letter code.

TABLE II

| COMPOUND | RATE OF APPLICATION (ppm) | SPECIES | | | | | | |
|---|---|---|---|---|---|---|---|---|
| | | TU | MPa | MDa | MDb | HV | SE | DB |
| | | | | | (see Table III) | | | |
| 1 | 500 | C | A | A | A | C | A | C |
| 2 | 500 | C | C | A | A | A | A | A |
| 5 | 500 | C | C | A | A | C | B | C |
| 6 | 500 | C | C | A | B | A | A | C |
| 7 | 500 | C | C | A | A | C | B | — |
| 10 | 500 | C | C | A | A | B | A | — |
| 15 | 500 | C | C | A | B | A | A | A |
| 16 | 500 | C | B | A | A | A | A | — |
| 22 | 500 | C | C | A | B | C | C | A |
| 47 | 500 | C | C | A | A | B | A | B |
| 48 | 500 | C | C | — | A | C | A | C |
| 49 | 500 | C | A | — | A | A | A | B |
| 50 | 500 | C | C | A | A | A | A | — |
| 51 | 500 | C | C | — | A | A | A | C |
| 52 | 500 | C | C | A | A | C | A | C |
| 53 | 500 | C | C | — | A | C | A | C |
| 54 | 500 | C | C | A | A | A | A | A |
| 55 | 500 | C | C | A | A | A | A | B |
| 56 | 500 | C | C | A | B | C | A | A |
| 57 | 500 | C | C | A | A | C | A | B |
| 58 | 500 | C | C | A | A | A | A | A |
| 60 | 500 | C | C | A | A | B | C | — |
| 61 | 500 | C | C | A | A | C | C | — |
| 62 | 500 | C | C | A | B | C | B | B |
| 63 | 500 | C | C | A | B | C | A | C |
| 64 | 500 | C | C | — | A | C | A | C |
| 67 | 500 | C | C | — | A | C | A | C |
| 68 | 500 | C | C | A | A | C | B | A |
| 69 | 500 | C | A | A | A | C | B | C |
| 71 | 500 | C | C | A | A | C | C | — |
| 73 | 500 | C | C | A | A | B | A | — |
| 74 | 500 | C | C | A | A | A | A | C |
| 75 | 500 | A | C | A | C | A | A | A |
| 76 | 500 | C | C | — | A | C | A | C |
| 77 | 500 | C | C | A | A | A | B | C |
| 78 | 500 | B | C | — | — | C | A | C |
| 79 | 500 | C | C | A | A | A | A | A |
| 81 | 500 | C | C | A | A | B | B | — |
| 82 | 500 | C | C | A | A | A | C | — |
| 83 | 500 | A | C | A | A | C | B | B |
| 86 | 500 | C | B | — | A | C | A | C |
| 101 | 500 | C | C | A | A | B | C | — |

TABLE III

| CODE LETTERS | TEST SPECIES | SUPPORT MEDIUM/FOOD | TYPE OF TEST | DURATION (days) |
|---|---|---|---|---|
| TU | *Tetranychus urticae* (spider mite) | French bean leaf | Contact | 3 |
| MPa | *Myzus persicae* (green peach aphid) | Chinese Cabbage leaf | Contact | 3 |
| MDa | *Musca domestica* (houseflies - adults) | Cotton wool/sugar | Knockdown | 15 mins |
| MDb | *Musca domestica* (houseflies - adults) | Cotton wool/sugar | Contact | 2 |
| HV | *Heliothis virescens* (Tobacco budworm - larva) | Soya leaf | Residual | 5 |
| SE | *Spodoptera exigua* (lesser armyworm - larva) | Cotton leaf | Residual | 5 |
| DB | *Diabrotica balteata* (banded cucumber beetle - larva) | Filter paper/maize seed | Residual | 2 |

"Contact" test indicates that both pests and medium were treated. "Residual" indicates that the medium was treated before infestation with the pests and "in vitro" indicates that the pest was suspended in an aqueous medium containing the treatment.

EXAMPLE 9

This Example further illustrates the insecticidal activity of compounds of Formula (I) according to the invention.

In Table IV, further results are given for the activity of test compounds against four species at various rates of application. The test procedures and details for tests TU (*Tetranychus urticae*, contact), MPa *Myzus persicae*, contact) and DB (*Diabrotica balteata*, contact) are as described in Example 8 and Table III. Application rates are shown in the table heading for each test type. The test procedure for Test MPb (*Myzus persicae*, systemic) was as follows:

Upward systemicity of the test compounds was evaluated against the peach potato aphid, *Myzus persicae* by soil drenching 2–3 week old radish plants (cv. Cherrybelle) at 10 ppm. Plants with 1st true leaves approximately 2×1 cm were used. The cotyledons, growing point and 1 true leaf were removed. The soil was covered with a clear lid. 12–18 mature aphids were added to each plant 1 day before treatment. On the treatment day each pot was placed in a 250 ml plastic pot with a fluon band to prevent aphid escape. Each pot was treated with 10 ml of chemical solution (prepared in 1% ethanol and acetone (1:1) and 0.01% Synperonic NP8-ICI Chemicals & Polymers). Each treatment was replicated 3 times. The treated plants were transferred to a constant environment room at 20° C., 60% relative humidity and a 16 hour photoperiod. The mortality was assessed at 3 and 5 days after treatment (DAT).

Results in Table IV are expressed as % Control observed. —indicates that either the compound was not tested or no meaningful result was obtained.

TABLE IV

| COMPOUND NO. | SPECIES | | | |
|---|---|---|---|---|
| | TU (25 ppm) | MPa (27 ppm) | DB (25 ppm) | MPb (10 ppm) |
| 1 | 89 | — | 97 | 36 |
| 2 | — | 94 | — | 33 |
| 5 | — | — | 90 | 24 |
| 15 | — | 65 | — | 12 |
| 22 | 83 | 100 | — | 46 |
| 26 | — | — | — | 9 |
| 45 | — | — | — | 24 |
| 47 | 85 | 40 | — | 1 |
| 52 | 69 | 100 | 10 | 7 |
| 56 | 100 | 94 | — | 0 |
| 57 | — | 100 | — | 67 |
| 58 | 78 | 95 | — | 21 |
| 62 | — | 100 | — | 5 |
| 63 | 96 | 100 | 100 | 10 |
| 64 | — | — | — | 100 |
| 65 | — | — | — | 36 |
| 69 | — | — | 97 | — |
| 74 | — | 100 | 70 | — |
| 77 | — | — | 70 | — |
| 78 | — | 38 | 97 | — |
| 85 | — | — | — | 25 |
| 90 | — | — | — | 68 |
| 91 | — | — | — | 33 |
| 92 | — | — | — | 100 |
| 93 | — | — | — | 100 |

EXAMPLE 10

This Example illustrates the nematicidal properties of the compounds of Formula (I) according to the invention.

Three tests were established to demonstrate nematicidal efficacy.

Test A: In vitro test.

In vitro activity against the root knot nematode, *Meloidogyne incognita* was evaluated by treatment of a suspension of freshly-hatched (0–24 hours old) juveniles of *M.incognita* with a liquid composition containing the test chemical at test rates of 1.65–0.02 ppm. To prepare the compositions, the test chemicals were diluted to double the rate required in 1% ethanol and acetone (1:1) and 99% deionised water. 0.5 cm$^3$ of chemical solution was added to 0.5 cm of nematode suspension ($\delta$200 nematodes/cm$^3$) in a glass vial. Each treatment was replicated twice. The vials were capped and left for 72 hours in a Constant Temperature room at 23° C. in the dark. The numbers of dead and alive nematodes were then counted under a stereomicroscope and the number of dead nematodes is expressed in Table V as a percentage of the total nematode count (% Dead).

Test B: Soil drench test.

Activity against the root knot nematode, *Meloidogyne incognita*, was evaluated by applying the candidate nematicide as a drench solution to 2 week old cucumber plants (cultivar Telegraph) and infesting the soil with nematodes. 10 cm of a solution comprising the test compound, dissolved in a 1% solvent solution (50:50 acetone and ethanol), and 0.05% SYNPERONIC NP8 (ICI Chemicals & Polymers) in distilled water was added to each plant such that the final soil concentration was 2 ppm. Each treatment was replicated twice. The cucumber plants were inoculated 48 hours after treatment with a 2 cm$^3$ suspension of freshly hatched juveniles at a concentration of 350 nematodes per cm. The test was maintained at 25° C. with a 16 hour photoperiod for 9 days. The roots of each plant were assessed for percentage root-knot reduction relative to an untreated, infested control and the results are recorded in Table V as Z knot reduction compared to the control.

Test C: Foliar application test.

Downward systemicity of test chemicals was evaluated by spraying 4–6" high tomato plants (cultivar Moneymaker) to incipient run-off with a chemical solution at 1000 ppm. Soil contamination was prevented by wrapping plastic film around the base of the stem and over the soil. The chemical solution (diluted in 5% ethanol and acetone (1:1) and 5% sucrose) was sprayed onto the plants (5cm$^3$/plant) at 15 p.s.i. (103.4 kPa) with a hand operated sprayer. Each treatment was replicated three times. 48 hours after treatment each plant was inoculated with 700 freshly-hatched (0–24 hours old) juveniles of *Meloidogyne incognita* (root knot nematode). Plants were maintained in a constant environment at 25° C. for 21 days and watered from the base of the pot. Root-knot reduction relative to an untreated, infested control was then assessed and the results are recorded in Table V as % knot reduction compared to the control.

TABLE V

| COMPOUND NO | TEST A (% Dead) 1.65 ppm | TEST B (% Knot reduction) 2.0 ppm | TEST C (% Knot reduction) 1000 ppm |
| --- | --- | --- | --- |
| 1 | 94.7 | 87.3 | 72.7 |
| 2 | 96.7 | 100 | 4.7 |
| 5 | 98.1 | 90.1 | — |
| 6 | 92.5 | 0.3 | — |
| 7 | 99 | 0 | — |
| 10 | 93.5 | — | — |
| 12 | 94.1 | — | — |
| 15 | 93.5 | 99.6 | — |
| 16 | 62.2 | 67.2 | — |
| 22 | 100 | 95.5 | 51.9 |
| 26 | 94.3 | — | — |
| 45 | 97.3 | 0 | — |
| 46 | 94.4 | 94.9 | — |
| 47 | 97.2 | 100 | 27.8 |
| 48 | 96.6 | 64.2 | — |
| 49 | 96 | 72.3 | — |
| 50 | 95.6 | 77.5 | — |
| 52 | 94.2 | 95.4 | 85.9 |
| 56 | 96.3 | 67.4 | — |
| 57 | 93.3 | 98.9 | 54.5 |
| 58 | 93.1 | 84.3 | — |
| 59 | 93 | 0.2 | — |
| 60 | 96.3 | 81.7 | — |
| 61 | 98 | 0 | — |
| 62 | 91.4 | 95.2 | — |
| 63 | 91.7 | 96 | — |
| 64 | 94.8 | 99.7 | — |
| 66 | 99 | 0 | — |
| 68 | 9.3 | 73.7 | — |
| 69 | 93.5 | — | — |
| 71 | 96.6 | 99.5 | — |
| 73 | 70.9 | 98.3 | — |
| 74 | 82.7 | 0 | — |
| 76 | 91.3 | 0 | — |
| 77 | 97.7 | 0.3 | — |
| 78 | 95.3 | 0.3 | — |
| 79 | 94.9 | 0 | — |
| 80 | 94.3 | 0.3 | — |
| 81 | 95.9 | 0 | — |

TABLE V-continued

| COMPOUND NO | TEST A (% Dead) 1.65 ppm | TEST B (% Knot reduction) 2.0 ppm | TEST C (% Knot reduction) 1000 ppm |
| --- | --- | --- | --- |
| 82 | 83 | 0 | — |
| 83 | 95.6 | 0.3 | — |
| 84 | 2.5 | 83.3 | — |
| 85 | 98.6 | — | — |
| 86 | 94.9 | 57.2 | — |
| 87 | 95.0 | — | — |
| 90 | 94.7 | — | — |
| 91 | 98.3 | — | — |
| 92 | 98.4 | 100 | — |
| 93 | 6.9 | 99.6 | — |
| 95 | 98.3 | 97.5 | — |
| 96 | 96.3 | — | — |
| 98 | 90.2 | 0 | — |
| 101 | 76.2 | 0 | — |
| 107 | 94.7 | 100 | — |
| 134 | 96.8 | 51.1 | — |
| 137 | 99.4 | — | — |
| 143 | 92.5 | 100 | — |
| 150 | 97.3 | 98.8 | — |

EXAMPLE 11

The spectrum of nematicidal activity of compounds of Formula (I) according to the invention was investigated in contact assays. Greatest activity was seen against endoparasitic species such as the root-knot nematode *Meloidogyne incognita*, the potato cyst nematode *Globodera rostochiensis*, the sugarbeet cyst nematode *Heterodera schachtii* and the reniform nematode *Rotylenchulus reniformis*. Activity was evident, but to a lesser extent, against migratory species such as *Aphelenchoides spp* and *Ditylenchus spp*. This indicates that compounds according to the invention have the potential for broad spectrum control of nematode species representative of different habitats and feeding habits.

The following examples demonstrate formulations suitable for applying the compounds of the present invention. The amount of ingredient is expressed in parts by weight or grams per liter as indicated. * indicates a trademark.

EXAMPLE 12

This example demonstrates granules suitable for soil application. The granules can be made be standard techniques such as impregnation, coating, extrusion or agglomeration.

|  |  | % w/w |
| --- | --- | --- |
| Impregnated granule: | Active ingredient | 5 |
|  | Wood Rosin | 2.5 |
|  | Gypsum granules (20–40 mesh) | 92.5 |
| Coated granule: | Active ingredient | 0.5 |
|  | 'Solvesso'* 200 | 0.4 |
|  | Calcium carbonate granules (30–60 mesh) | 99.1 |
| Slow release granule: | Active ingredient | 10 |
|  | Polyvinylacetate/vinyl chloride copolymer latex | 5 |
|  | Attapulgus granules | 85 |

EXAMPLE 13

This example demonstrates formulations for use as a spray. The compounds can be formulated as wettable powders, water dispersible granules, suspension concentrates, emulsifiable concentrates, emulsions or microcapsule suspensions for application diluted in water.

| | | g/l |
|---|---|---|
| Emulsifiable concentrate: | Active ingredient | 250 |
| | Calcium dodecyl-benzene sulphonate | 50 |
| | Nonyl phenol ethoxylate | 50 |
| | Alkylbenzene solvent | to 1 liter |
| | | % w/w |
| Wettable powder: | Liquid active ingredient | 40 |
| | lignosulphonate dispersant | 5 |
| | silica | 25 |
| | sodium lauryl sulphate | 3 |
| | china clay (kaolin) | 27 |
| Microcapsule suspension: | Liquid active ingredient | 250 |
| | toluene diisocyanate | 10 |
| | polymethylene polyphenyl isocyanate | 20 |
| | nonyl phenol ethoxylate | 6 |
| | lignosulphonate dispersant | 15 |
| | zanthan gum | 1 |
| | bentonite | 10 |
| | biocide 'Proxel'* | 0.1 |
| | sodium carbonate | 5 |
| | water | to 1 liter |

The microcapsule suspensions can be used as a spray, soil drench or as an intermediate to prepare slow release granules for application to the soil.

| | | g/l |
|---|---|---|
| Suspension concentrate: | Solid active ingredient | 400 |
| | lignosulphonate dispersant | 50 |
| | sodium lauryl sulphate | 30 |
| | xanthan gum | 1 |
| | biocide 'Proxel'* | 0.1 |
| | bentonite | 10 |
| | water | to 1 liter |

EXAMPLE 14

This example demonstrates formulations suitable for use as seed treatments in conventional application machinery.

| | | % w/w |
|---|---|---|
| Dry seed treatment: | Active ingredient | 20 |
| | dodecyl benzene | 3 |
| | Rubine Toner (dyestuff) | 2.7 |
| | Talc | 53.3 |
| | Silica | to 100% |

The suspension concentrate and microcapsule suspension of Example 5 can be used as flowable concentrates for seed treatment.

EXAMPLE 15

This example demonstrates the formulation of the compounds for electrostatic spraying.

| | g/l |
|---|---|
| Active ingredient | 200 |
| N-methylpyrrollidone | 50 |
| Soyabean oil | 120 |
| 'Solvesso'* 200 | to 1 liter |

EXAMPLE 16

This Example illustrates the fungicidal properties of the compounds of Formula (I) according to the invention.

The test compounds were formulated either by bead milling with aqueous Dispersol T or as a solution in acetone or acetone/ethanol. They were then diluted to 100 ppm in water, and 2.5 cm³ aliquots were placed in Petri dishes. These were further diluted to 25 ppm (active ingredient) with Potato Dextrose Agar.

The dishes were inoculated with the fungal pathogens shown in Table V, using either spore suspensions or mycelial plugs. These were then incubated at an appropriate temperature (19°–25° C.) and growth assessments made after 2 days as a percentage of the level of disease present on the untreated control medium. The results are expressed in Table VI as a POCO (Percentage of Control) value calculated according to the formula given below and rounded to the nearest figure on the following standard scale: 0, 1, 3, 5, 10, 15, 20, 30, 60, 90.

$$POCO = \frac{\text{disease level on treated medium}}{\text{disease level on untreated control}}$$

TABLE V

| | Test Organisms |
|---|---|
| Abbreviations | Latin Name |
| Ch | *Pseudocercosporella herpotrichoides* |
| Sn | *Septoria nodorum* |
| Bc | *Botrytis cinerea* |
| Po | *Pyricularia oryzae* |
| Tc | *Thanatephorus cucumeris* |
| Au | *Aureobasidium pullulans* |

TABLE VI

| Compound No | Ch | Sn | Bc | Po | Tc | Au |
|---|---|---|---|---|---|---|
| 1 | 90 | 90 | 90 | 3 | 90 | 90 |
| 2 | 3 | 50 | 3 | 3 | 50 | 50 |
| 22 | 3 | 50 | 15 | 3 | 90 | 90 |
| 46 | 0 | 50 | 50 | 3 | 50 | 50 |
| 57 | 3 | 15 | 3 | 3 | 50 | 50 |
| 58 | 3 | 50 | 15 | 3 | 90 | 15 |

CHEMICAL FORMULA
(IN DESCRIPTION)

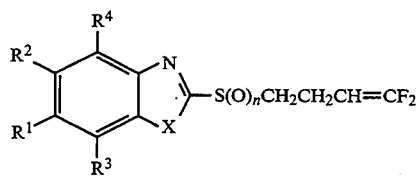

(I)

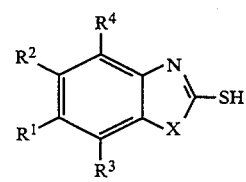

(II)

-continued

CHEMICAL FORMULA
(IN DESCRIPTION)

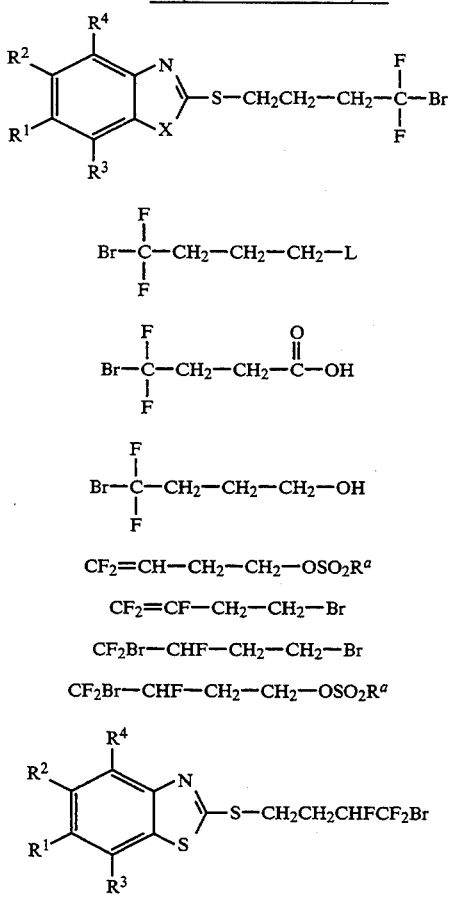

$CF_2=CH-CH_2-CH_2-OSO_2R^a$ (VII)

$CF_2=CF-CH_2-CH_2-Br$ (VIII)

$CF_2Br-CHF-CH_2-CH_2-Br$ (IX)

$CF_2Br-CHF-CH_2-CH_2-OSO_2R^a$ (X)

(XI)

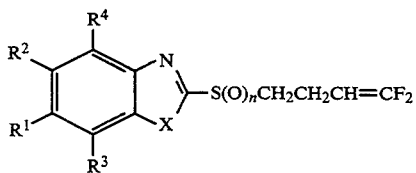

We claim:
1. A compound of Formula (I)

(I)

wherein:
x is oxygen or sulphur;
n is 0, 1 or 2;
$R^1$, $R^2$, $R^3$, and $R^4$ are independently selected from hydrogen, alkyl, alkenyl, alkynyl, cycloalkyl, alkylcycloalkyl, optionally substituted aryl, optionally substituted arylalkyl, optionally substituted aryloxy, optionally substituted arylalkoxy, alkoxy, alkenyloxy, alkynyloxy, hydroxyalkyl, alkoxyalkyl, alkylthio, alkenylthio, alkynylthio, haloalkyl, haloalkenyl, haloalkynyl, haloalkoxy, haloalkenyloxy, haloalkynyloxy, haloalkylthio, haloalkenylthio, haloalkynylthio, halogen, hydroxy, cyano, nitro, $-NR^5R^6$, $-NR^7COR^8$, $-NR^9SO_2R^{10}$, $-N(SO_2-R^{11})(SO_2-R^{12})$ $-COR^{13}$, $-CONR^{14}R^{15}$, $-COOR^{16}$, $-OCOR^{17}$, $-OSO_2R^{18}$, $-SO_2NR^{19}R^{20}$, $-SO_2R^{21}$, $-SOR^{22}$, $-CSNR^{23}R^{24}$, $-SiR^{25}R^{26}R^{27}$, $-OCH_2CO_2R^{28}$, $-OCH_2CH_2CO_2R^{29}$, $-CONR^{30}SO_2R^{31}$ and $-SO_2Z$; or an adjacent pair of $R^1$, $R^2$, $R^3$ and $R^4$ when taken together form a fused 5- or 6-membered carbocyclic or heterocyclic ring;
$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, and $R^{31}$ are independently selected from hydrogen, alkyl, alkenyl, alkynyl, haloalkyl, haloalkenyl, haloalkynyl, optionally substituted aryl and optionally substituted arylalkyl; and
Z is halogen.

2. Compound as claimed in claim 1 wherein
X is oxygen or sulphur;
n is 0, 1 or 2;
$R^1$, $R^2$, $R^3$, and $R^4$ are independently selected from hydrogen, $C_{1-6}$ alkyl, $C_{2-6}$ alkenyl, $C_{2-6}$ alkynyl, $C_{3-6}$ cycloalkyl, $C_{4-7}$ alkylcycloalkyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenyl-$C_{1-2}$-alkyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, phenoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, Phenyl-$C_{1-2}$-alkoxy optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, $C_{1-6}$ alkoxy, $C_{2-6}$ alkenyloxy, $C_{2-6}$ alkynyloxy, hydroxy-$C_{1-6}$-alkyl, $C_{2-6}$ alkoxyalkyl, $C_{3-6}$ dialkoxyalkyl, $C_{1-6}$ alkylthio, $C_{2-6}$ alkenylthio, $C_{2-6}$ alkynylthio, $C_{1-6}$ haloalkyl, $C_{2-6}$ haloalkenyl, $C_{2-6}$ haloalkynyl, $C_{1-6}$ haloalkoxy, $C_{2-6}$ haloalkenyloxy, $C_{2-6}$ haloalkynyloxy, $C_{1-6}$ haloalkylthio, $C_{2-6}$ haloalkenylthio, $C_{1-6}$ haloalkynylthio, halogen, hydroxy, cyano, nitro, $-NR^5R^6$, $-NR^7COR^8$, $-NR^9SO_2R^{10}$, $-SO_2NR^{19}R^{20}$, $-SO_2R^{21}$, $-SOR^{22}$, $-CSNR^{23}R^{24}$, $-SiR^{25}R^{26}R^{27}$, $-OCH_2CO_2R^{28}$, $-OCH_2CH_2CO_2R^{29}$, $-NR^{30}SO_2R^{31}$ and $-SO_2Z$; or an adjacent pair of $R^1$, $R^2$, $R^3$ and $R^4$ when taken together form a fused 5- or 6-membered heterocyclic ring containing two oxygen atoms and optionally substituted with one or more halogen or methyl groups, or a 5- or 6-membered carbocyclic ring;
$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$ and $R^{31}$ are independently selected from hydrogen, $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, phenyl optionally substituted by halogen, $C_{1-4}$ alkyl, $C_{1-4}$ alkoxy, $C_{1-4}$ haloalkyl, $C_{1-4}$ haloalkoxy, hydroxy, cyano or nitro, and benzyl optionally substituted by halogen, $C_{1-4}$ alkyl, $C_{1-4}$ alkoxy, $C_{1-4}$ haloalkyl, $C_{1-4}$ haloalkoxy, hydroxy, cyano and nitro; and
Z is fluoro, chloro or bromo.

3. A compound as claimed in claim 1 wherein
X is oxygen or sulphur;
n is 0, 1 or 2;
$R^1$, $R^2$, $R^3$, and $R^4$ are independently selected from hydrogen, $C_{1-4}$ alkyl, $C_{2-6}$ alkenyl, $C_{2-6}$ alkynyl, $C_{3-6}$ cycloalkyl, $C_{4-7}$ alkylcycloalkyl, phenyl optionally substituted by chloro, fluoro, methyl, ethyl, methoxy, trifluoromethoxy, trifluoromethyl or nitro, benzyl optionally substituted by chloro, fluoro, methyl, ethyl, methoxy, trifluoromethoxy, trifluoromethyl or nitro, phenoxy optionally substituted by chloro, fluoro, methyl, trifluoromethyl or alkenyloxy, $C_{2-4}$ alkynyloxy, hydroxy-$C_{1-4}$-alkyl, $C_{2-4}$ alkoxyalkyl, nitro, benzoxy optionally substituted by chloro, fluoro, methyl, trifluoromethyl or nitro, 4-nitrobenzoxy, $C_{1-4}$ alkoxy, $C_{2-6}$ alkenyloxy, $C_{2-4}$ alkynyloxy, hydroxy-$C_{1-4}$-alkyl, $C_{2-4}$ alkoxyalkyl, $C_{3-6}$ dialkoxyalkyl, $C_{1-4}$ alkylthio, $C_{2-6}$ alkenylthio, $C_{2-4}$ alkynylthio, $C_{1-4}$ fluoroalkyl, $C_{1-4}$ chloroalkyl, $C_{2-6}$ fluoroalkenyl, $C_{2-4}$ chloroalkenyl, $C_{1-4}$ fluoroalkoxy, $C_{1-4}$ chloroalkoxy, $C_{2-6}$ fluoroalkenyloxy, $C_{2-4}$ chloroalkenyloxy, $C_{1-4}$ fluoroalkylthio, $C_{1-4}$ chloroalkylthio, $C_{2-6}$ fluoroalkenylthio, $C_{2-4}$ chloroalkenylthio, chloro, fluoro, bromo, iodo, hydroxy, cyano, nitro, amino, —$NHR^5$ where $R^5$ is $C_{1-4}$ alkyl, —$NR^5R^6$ where $R^5$ and $R^6$ are $C_{1-4}$ alkyl, —$NR^7COR^8$ where $R^7$ is hydrogen and $R^8$ is hydrogen or $C_{1-4}$ alkyl, —$NR^9SO_2R^1$ where $R^9$ is hydrogen and $R^{10}$ is $C_{1-4}$ alkyl, —$N(SO_2-R^{11})(SO_2-R^{12})$ where $R^{11}$ and $R^{12}$ are $C_{1-4}$ alkyl, —$COR^{13}$ where $R^{13}$ is hydrogen or $C_{1-4}$ alkyl, —$CONR^{14}R^{15}$ where $R^{14}$ and $R^{15}$ are hydrogen or $C_{1-4}$ alkyl, —$COOR^{16}$ where $R^{16}$ is hydrogen, $C_{1-4}$ alkyl, $C_{1-4}$ haloalkyl or $C_{2-6}$ fluoroalkenyl, —$OCOR^{17}$ where $R^{17}$ is $C_{1-4}$ alkyl, —$OSO_2R^{18}$ where $R^{18}$ is $C_{1-4}$ alkyl, —$SO_2NR^{19}R^{20}$ where $R^{19}$ and $R^{20}$ are hydrogen or $C_{1-4}$ alkyl, —$SO_2R^{21}$ where $R^{21}$ is $C_{1-4}$ alkyl or $C_{1-4}$ haloalkyl, —$SOR^{22}$ where $R^{22}$ is $C_{1-4}$ alkyl or $C_{1-4}$ haloalkyl, —$CSNR^{23}R^{24}$ where $R^{23}$ and $R^{24}$ are hydrogen or $C_{1-4}$ alkyl, —$SiR^{25}R^{26}R^{27}$ where $R^{25}$, $R^{26}$ and $R^{27}$ are $C_{1-4}$ alkyl, —$OCH_2CO_2R^{28}$ where $R^{28}$ is $C_{1-4}$ alkyl, —$CONR^{30}SO_2R^{31}$ where $R^{30}$ is hydrogen and $R^{31}$ is $C_{1-4}$ alkyl and —$SO_2F$; or where $R^1$ and $R^2$ taken together, $R^1$ and $R^3$ taken together or $R^2$ and $R^4$ taken together are —$(CH_2)_3$—, —$(CH_2)_4$—, —CH=CH—CH=CH—, or —O—$CH_2$—O— optionally substituted with one or two halogen atoms.

4. A compound according to claim 1 wherein
X is oxygen or sulphur;
n is 0, 1 or 2;
$R^1$, $R^2$, $R^3$, and $R^4$ are independently selected from hydrogen, ethyl, allyl, but-3-enyl, 3-methylbut-3-enyl, ethynyl, propargyl, cyclopropyl, 1-methylcyclopropyl, phenyl, 4-chlorophenyl, 4-fluorophenyl, 3-trifluoromethylphenyl, 4-trifluoromethylphenyl, 4-methylphenyl, 4-nitrophenyl, benzyl, 4-chlorobenzyl, 4-fluorobenzyl, 3-trifluoromethylbenzyl, 4-trifluoromethylbenzyl, 4-methylbenzyl, 4-nitrobenzyl, phenoxy, 4-chlorophenoxy, 4-fluorophenoxy, 3-trifluoromethylphenoxy, 4-trifluoromethylphenoxy, 4-methylphenoxy, 4-nitrophenoxy, benzoxy, 4-chlorobenzoxy, 4-fluorobenzoxy, 3-trifluoromethylbenzoxy, 4-trifluoromethylbenzoxy, 4-methylbenzoxy 4-nitrobenzoxy, methoxy, ethoxy, iso-propoxy, n-propoxy, sec-butoxy, allyloxy, but-3-enyloxy, 3-methylbut-3-enyloxy, propargyloxy, hydroxymethyl, 2-hydroxyethyl, 3-hydroxypropyl, methoxymethyl, ethoxymethyl, methoxyethyl, dimethoxymethyl, methylthio, ethylthio, allylthio, but-3-enylthio, 3-methylbut-3-enylthio, propargylthio, fluoromethyl, difluoromethyl, trifluoromethyl, 2-fluoroethyl, chloromethyl, dichloromethyl, trichloromethyl, 2,2-difluoroethenyl, 3,4,4-trifluorobut-3-enyl, 4,4-difluorobut-3-enyl, 4,4-difluoro-3-methylbut-3-enyl, 3,3-dichloroprop-2-enyl, 2-chloroprop-2-enyl, fluoromethoxy, difluoromethoxy, trifluoromethoxy, 2-fluoroethoxy, 1,1,2,2-tetrafluoroethoxy, trichloromethoxy, 3,4,4-trifluorobut-3-enyloxy, 4,4-difluorobut-3-enyloxy, 4,4-difluoro-3-methylbut-3-enyloxy, 2-chloroprop-2-enyloxy, 3,3-dichloroprop-2-enyloxy, fluoromethylthio, difluoromethylthio, trifluoromethylthio, 2-fluoroethylthio, trichloromethylthio, 3,4,4-trifluorobut-3-enylthio, 4,4-difluorobut-3-enylthio, 4,4-difluoro-3-methylbut-3-enylthio, 2-chloroprop-2-enylthio, 3,3-dichloroprop-2-enylthio, chloro, fluoro, bromo, iodo, hydroxy, cyano, nitro, amino, methylamino, ethylamino, dimethylamino, diethylamino, formamido, acetamido, propionamido, benzamido, methanesulphonamido, ethanesulphonamido, N,N-di-(methanesulphonyl)amino, N,N-di-(ethanesulphonyl)amino, formyl, acetyl, propionyl, carboxamido, N-methylcarboxamido, N-ethylcarboxamido, N,N-dimethylcarboxamido, N-methyl-N-ethylcarboxamido, N,N-diethylcarboxamido, N-(n-propyl)carboxamido, —COOH, methoxycarbonyl, ethoxycarbonyl, 2-fluoroethoxycarbonyl, 3,4,4-trifluorobut-3-enyloxycarbonyl, 3-methyl-4,4-difluorobut-3-enyloxycarbonyl, 4,4-difluorobut-3-enyloxycarbonyl, methoxycarbonyloxy, ethoxycarbonyloxy, methanesulphonyloxy, ethanesulphonyloxy, —$SO_2NH_2$, N,N-dimethylaminosulphonyl, N,N-diethylaminosulphonyl, methanesulphonyl, ethanesulphonyl, trifluoromethanesulphonyl, methanesulphinyl, ethanesulphinyl, trifluoromethanesulphinyl, —$CSNH_2$, —$CSNH(CH_3)$, —$CSN(CH_3)_2$, trimethylsilyl, —$OCH_2CO_2CH_3$, —$OCH_2CO_2CH_2CH_3$, N-(methanesulphonyl)carboxamido and —$SO_2F$; or where $R^1$ and $R^2$ taken together, $R^1$ and $R^3$ taken together or $R^2$ and $R^4$ taken together are —$(CH_2)_3$—, —$(CH_2)_4$—, —CH=CH—CH=CH—, —O—$CH_2$—O—, —O—CHF—O—, —O—$CF_2$—O—, —O—$CH(CH_3)$—O—, —O—$C(CH_3)_2$—O— or —O—$(CH_2)_2$—O—.

5. A compound as claimed in claim 1 wherein:
X is oxygen or sulphur;
n is 0, 1 or 2;
$R^1$, $R^2$, $R^3$, and $R^4$ are independently selected from hydrogen, $C_{1-4}$ alkyl, $C_{1-4}$ alkoxy, $C_{1-4}$ alkylthio, $C_{1-4}$ fluoroalkyl, $C_{1-4}$ fluoroalkoxy, $C_{2-6}$ fluoroalkenyloxy, $C_{1-4}$ fluoroalkylthio, $C_{2-6}$ fluoroalkenylthio, chloro, fluoro, bromo, iodo, hydroxy, cyano, nitro, —$COOR^{16}$ where $R^{16}$ is hydrogen, $C_{1-4}$ alkyl, $C_{1-4}$ haloalkyl or $C_{2-6}$ fluoroalkenyl —$SO_2R^{21}$ where $R^{21}$ is $C_{1-4}$ alkyl or $C_{1-4}$ haloalkyl, —$SOR^{22}$ where $R^{22}$ is $C_{1-4}$ alkyl or $C_{1-4}$ haloalkyl and —$CSNH_2$; or where $R^1$ and $R^2$ taken together are —O—$(CH_2)_2$—O—.

6. A compound as claimed in claim 1 wherein:
X is oxygen or sulphur;
n is 0, 1 or 2;
$R^1$, $R^2$, $R^3$, and $R^4$ are independently selected from hydrogen, methyl, ethyl, methoxy, ethoxy, iso-propoxy, sec-butoxy, methylthio, ethylthio, fluoromethyl, difluoromethyl, trifluoromethyl, fluoromethoxy, difluoromethoxy, trifluoromethoxy, 2-fluoroethoxy, 1,1,2,2-tetrafluoroethoxy, 3,4,4-trifluorobut-3-enyloxy, 4,4-difluorobut-3-enyloxy, 4,4-difluoro-3-methylbut-3-enyloxy, trifluoromethylthio, 3,4,4-trifluorobut-3-enylthio, 4,4-difluorobut-3-enylthio, 4,4-difluoro-3-methylbut-3-enylthio, chloro, fluoro, bromo, iodo, hydroxy, cyano, nitro, —COOH, methoxycarbonyl, ethoxycarbonyl, 2-fluoroethoxycarbonyl, 3,4,4-trifluorobut-3-enyloxycarbonyl, 3-methyl-4,4- difluorobut-3-enyloxycarbonyl, 4,4-difluorobut-3-enyloxycarbonyl, methanesulphonyl, trifluoromethanesulphonyl, trifluoromethanesulphinyl and —CSNH$_2$; or where R$^1$ and R$^2$ taken together are —O—(CH$_2$)$_2$—O—.

7. A compound as claimed in claim 1 wherein at least two of the groups R$^1$, R$^2$, R$^3$, and R$^4$ are hydrogen.

8. A compound as claimed in claim 1 wherein each of the groups R$^1$, R$^2$, R$^3$ and R$^4$ is hydrogen.

9. A compound of Formula (I) according to claim 1 wherein n is 0.

10. A nematicidal, insecticidal or acaricidal composition comprising a nematicidally, insecticidally or acaricidally effective amount of a compound of formula (I) as claimed in claim 1 and an inert diluent or carrier material.

11. A method for killing or controlling nematode, insect or acarid pests which comprises applying to the locus of the pest or to a plant or seed susceptible to attack by the pest an effective mount of a composition as claimed in claim 10.

12. A fungicidal composition comprising a fungicidally effective amount of a compound as claimed in any claim 1 and a fungicidally acceptable carrier or diluent.

13. A method of combating fungi which comprises applying to a plant, to a seed of a plant or to the locus of the plant or seed a fungicidally effective amount of a composition as claimed in claim 12.

* * * * *